(12) United States Patent
Gianturco et al.

(10) Patent No.: US 6,194,558 B1
(45) Date of Patent: Feb. 27, 2001

(54) DNA ENCODING HUMAN MONOCYTE-MACROPHAGE APOLIPOPROTEIN B RECEPTOR GENE AND PROTEIN

(75) Inventors: Sandra H. Gianturco; William A. Bradley, both of Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/130,242

(22) Filed: Aug. 6, 1998

(51) Int. Cl.⁷ .................................................. C07H 21/04
(52) U.S. Cl. ...................... 536/23.5; 530/350; 435/69.1; 435/252.3; 436/501
(58) Field of Search ........................ 530/350; 536/23.5; 435/252.3, 69.1; 436/501

(56) References Cited

PUBLICATIONS

Bowie, Ju et al., Deciphering the message in protein sequences: tolerance to amino acid substitutions. Science 247(1306–1310) Mar. 1990.*

Wells Ja. Additivity of mutational effects in proteins, Biochemistry 29:37(8509–8517)Sep. 1990.*

Ngo, JT., Computational complexity, protein structure prediction, and the Levinthal paradox. In The Protein Folding Problem and Tertiary Structure Prediction. eds Merz, K., and Le Grand, S., Birkhauser Boston, 1994, pp. 14–16.*

Baker, A. and Cotten, M., Delivery of bacterial artificial chromosomes into mammalian cells with psoralen–inactivated adenovirus carrier. Nucleic Acids Res. 25:10(1950–1956)May 1997.*

Adams, MD and Loftus, BJ.(Jul. 24, 1998) Homo sapiens chromosome 16 BAC clone CIT987SK–A–761H5, Direct Submission, GenBank accession # AC002544. Accessed Oct. 18, 1999., GenBank is referenced as Benson, DA et al. GenBank. Nucleic Acids Res. 25:1(1–6.*

* cited by examiner

Primary Examiner—Elizabeth Kemmerer
Assistant Examiner—Michael Brannock
(74) Attorney, Agent, or Firm—Benjamin Aaron Adler

(57) ABSTRACT

The present invention provides an isolated DNA molecule that codes for a cell-surface binding protein in human monocytes and macrophages. In addition, an amino acid sequence derived from the nucleotide sequence is provided. The newly-identified cell-surface binding protein described herein is instrumental in the apoB-mediated cellular uptake of plasma chylomicrons and remnants and hypertriglyceridemic tryglyceride-rich lipoproteins in an ApoE- and lipoprotein lipase- and heparin sulfate proteoglycan-independent pathway. The present invention also provides evidence that the ligand for the receptor is within the N-terminal region of apoB-48 or B-100 at or near the lipoprotein lipase binding domain and not in a heparin binding domain.

6 Claims, 17 Drawing Sheets

```
           10          20          30          40
AVVWVRETED  EEAEADRTSR  RGWRLQAVAV  GLPDREDAQT 50          60          70          80
GSVAAGIMGG  DVVPHISAAG  RGEALEGALG  QGWDSKEKEE 90         100         110         120
AAAGEHAGGQ  EFGLEGSAEE  EVTGRGSQVE  AFESREGGPW 130         140         150         160
GGRVEAEESA  GAEDSCGLDP  AGSQTARAEG  MGAMVEAGGL 170         180         190         200
LEKWTLLEEE  AVGWQEREQR  EDSEGRCGDY  GPEGEAPRLL

DAEGLMVTG        (SEQ ID NO: 4)
```

Fig. 7

DNA ENCODING HUMAN MONOCYTE-MACROPHAGE APOLIPOPROTEIN B RECEPTOR GENE AND PROTEIN

BACKGROUND OF THE INVENTION

1. Field of the Invention

The present invention relates generally to the fields of molecular biology, cardiovascular medicine and cellular nutrition. More specifically, the present invention relates to DNA encoding the human monocyte-macrophage and placental triglyceride-rich lipoprotein/apolipoprotein B (apoB) receptor gene(s) and protein(s).

2. Description of the Related Art

Hypertriglyceridemia is a common, heterogeneous disorder. When chylomicrons persist in the fasting state, lipid-filled monocyte-macrophage-derived foam cells can accumulate in the spleen, liver, bone marrow, atherosclerotic lesions, and skin (Fredrickson, 1978). Many, but not all, early studies (Carlson, 1972; Brunzell, 1976; Grundy, 1988; Schaefer, 1988; Austin, 1991) indicate elevated plasma triglycerides are a risk factor for coronary heart disease and myocardial infarction, sequelae of atherosclerosis. The possibility that triglyceride-rich lipoproteins (hepatic as well as dietary) are involved in atherosclerosis has been strengthened recently. Both the Procam study and a follow-up of the Helsinki Heart Study implicate elevated triglycerides (and therefore triglyceride-rich lipoproteins) as an important risk factor in atherosclerosis (Assmann, 1992). Havel et al. demonstrated that plasma very low density lipoprotein and intermediate density lipoprotein cholesterol levels correlated with progression of coronary atherosclerosis disease, whereas low density lipoprotein cholesterol level did not (Phillips, 1993). Moreover, very low density lipoprotein-intermediate density lipoprotein particles enter the artery wall and are found in human atherosclerotic plaques (Rapp, 1994). Elevated postprandial chylomicron remnants of $S_f<400$ are significantly higher in subjects with coronary heart disease but with normal fasting lipid levels than in matched control subjects without this disease (Patsch, 1992; Weintraub, 1996). Thus, there is increasing biochemical as well as epidemiologic evidence that the major carriers of plasma triglycerides, very low density lipoproteins and plasma chylomicrons and their remnants, are atherogenic.

Monocytes and macrophages play a key role in atherogenesis, accounting for many lipid-filled "foam cells" in atherosclerotic lesions (Gerrity, 1981; Faggiotto, 1984). Many studies on foam cell formation have focused on uptake of modified and oxidized low density lipoprotein by the macrophage scavenger receptor and putative oxidized low density lipoprotein receptors (van Berkel, 1994). However, monocytes and macrophages also take up intestinally-derived plasma chylomicrons, which contain apoB-48, and hepatically-derived very low density lipoprotein (apoB-100). Zilversmit and colleagues demonstrated extrahepatic uptake of ~40% of chylomicrons in rabbits (Ross, 1977) that was decreased by inhibition of the reticuloendothelial system (Nagata, 1987). Furthermore, studies in marmosets (a primate) and rabbits demonstrated substantial uptake (20–40% of total) of chylomicrons in vivo by accessible, peripheral macrophages, particularly in bone marrow (both animals) and spleen (marmosets) (Hussain, 1989a, 1989b). This would suggest that triglyceride-rich lipoproteins serve as a non-modified, native source of lipid for monocytes' and macrophages' nutrition in the normal state.

Triglyceride-rich lipoproteins are involved in the pathological conversion of monocytes and macrophages into foam cells in humans, a process seen in bone marrow, spleen, etc. in types 1, 3 and 5 hypertriglyceridemia (Fredrickson, 1978). Triglyceride-rich lipoproteins are also involved in formation of monocyte-macrophage-derived foam cells in eruptive xanthomas in untreated hypertriglyceridemic diabetic subjects. These foam cells contained triglyceride-rich lipoprotein core lipids, triglycerides and cholesteryl esters, following chylomicron uptake (Parker, 1970).

Chylomicrons and hypertriglyceridemic-very low density lipoproteins (including β-very low density lipoproteins) are the only known native human lipoproteins, without modification, which directly cause rapid, receptor-mediated macrophage lipid accumulation in vitro, causing macrophages to resemble foam cells histologically (Gianturco, 1982b, 1986a, 1986b, 1988; Brown et al., 1983; Ostlund-Lindqvist, 1983; Bersot, 1986). The lipid that accumulates in macrophages after receptor-mediated uptake of a lipoprotein in vitro reflects the lipid composition of the lipoprotein (Gianturco, 1982b; Brown et al., 1983). Therefore, as seen in vivo, triglyceride is the predominant lipid which accumulates initially in macrophages exposed to hypertriglyceridemic-very low density lipoproteins or chylomicrons, but cholesterol and cholesteryl esters also accumulate even in short term incubations (Gianturco, 1986a). Triglyceride-rich lipoproteins enter the arterial wall in animals (Nordesgaard, 1994) and in man (Rapp, 1994). Since one triglyceride-rich lipoprotein $S_f>100$ contains 5 times or more cholesterol and cholesteryl esters than one low density lipoprotein (Shen, 1978), each triglyceride-rich lipoprotein that enters a monocyte, macrophage or the arterial wall is equivalent to 5 or more low density lipoprotein particles in terms of cholesterol delivery.

A number of plausible mechanisms for the above-described observations exist, many involving apoE. Very low density lipoproteins from hypertriglyceridemic subjects were first shown to be abnormal and potentially atherogenic in studies which showed that very low density lipoproteins from hypertriglyceridemic, but not from normal subjects, deliver cholesterol to cultured fibroblasts via the low density lipoprotein receptor (Gianturco, 1978). The abnormality in hypertriglyceridemic-very low density lipoproteins is primarily in the $S_f>60$ subfraction which, in contrast to normal very low density lipoproteins fraction $S_f>60$, contains extra apoE of an accessible conformation that specifically binds to the low density lipoprotein receptor; apoB of $S_f>60$ particles does not bind to the LDL receptor (Gianturco, 1982a, 1983; Bradley, 1984; Hui, 1984; Krul, 1985; Eisenberg 1988). ApoE also mediates triglyceride-rich lipoprotein binding to other widely-distributed receptors in the low density lipoprotein receptor gene family, such as the low density lipoprotein receptor-related protein/$\alpha_2$-macroglobulin receptor (Beisiegel, 1989; Kowal, 1989) and a very low density lipoprotein receptor expressed primarily in heart, muscle, and adipose (Takahashi, 1992). One of these could account for apoE-mediated very low density lipoprotein uptake observed in monocytes and macrophages (Wang-Iverson, 1985).

In contrast, apoB mediates the binding of low density lipoprotein (Goldstein, 1977), intermediate density lipoproteins ($S_f12$–20), and the predominant very low density lipoprotein in normal subjects, very low density lipoprotein$_3$ ($S_f20$–60) (Bradley, 1984; Krul, 1985), the only very low density lipoprotein subclass from normal subjects that binds to the low density lipoprotein receptor of fibroblasts (Gianturco, 1980a, 1982a, Eisenberg, 1988) or of U937 monocytes (Sacks and Breslow, 1988). The domain of apoB that binds to the low density lipoprotein receptor is in the C-terminal portion not present in apoB-48 (Yang, 1986; Milne, 1989).

Lipolysis of normal very low density lipoprotein $S_f>60$ permits binding of the lipolytic remnant to the low density lipoprotein receptor (Catapano, 1979; Schonfeld, 1979). Lipoprotein lipase secreted by macrophages (Khoo, 1981) hydrolyzes very low density lipoproteins and enhances its cellular uptake (Lindquist, 1983). This facilitation may occur through localization of triglyceride-rich lipoproteins to membrane heparin sulfate proteoglycan (Eisenberg, 1992) and/or through binding to low density lipoprotein receptor-related protein (Beisiegel, 1991).

The substantial and rapid uptake of triglyceride-rich chylomicrons in vivo by bone marrow and spleen macrophages in marmosets and rabbits was not accelerated by infusion of apoE (Hussain, 1989a). This is surprising, since apoE is a necessary ligand for the uptake of large triglyceride-rich lipoproteins by members of the low density lipoprotein receptor gene family. Indeed, infused apoE diverted much of the uptake from the peripheral macrophages to the liver, suggesting that the observed peripheral macrophage chylomicron uptake was not mediated by apoE and that these macrophages have an apoE-independent uptake mechanism. The rate and magnitude of triglyceride-rich chylomicron uptake by bone marrow monocytes and macrophages (20–40% of chylomicrons cleared from the plasma at 20 minutes (Hussain, 1989a)) suggests this uptake is receptor mediated. Rapid, receptor-mediated delivery of intestinally-derived, triglyceride-enriched chylomicrons may be necessary to assure delivery of sufficient energy and fat-soluble vitamins and other essential compounds to sustain hematopoiesis. In addition, and in contrast to inactivation of the ApoE gene, loss of apoB by homologous recombination caused embryonic lethality in the homozygous state. ApoB is normally expressed early in yolk sak visceral endodermal cells for the synthesis of apoB-containing lipoprotein which are apparently necessary for the transport of lipids and lipid-soluble vitamins to embryonic tissues.

Moreover, homologous recombinant ("knockout") mice that completely lack apoE accumulate very low density lipoprotein and chylomicron remnants in their plasma (Plump, 1992; Zhang, 1992). These mice develop atherosclerosis that is accelerated by high fat diets. The lesions are characterized by monocyte-macrophage-derived foam cells, as in human lesions, demonstrating unequivocally that apoE is not necessary for the conversion of monocytes and macrophages into foam cells in vivo (Nakashima, 1994; Reddick, 1994). Taken together, these in vivo studies suggest strongly the existence of an apoE-independent pathway for the uptake of triglyceride-rich lipoproteins by monocytes and macrophages which would result in foam cell formation in hypertriglyceridemia.

In vitro evidence for an apoE- and lipoprotein lipase-independent, apoB-mediated triglyceride-rich lipoprotein receptor pathway in murine macrophages has been reported (Gianturco, 1988). Because of the potential importance of an apoE-independent, receptor-mediated pathway for triglyceride-rich lipoproteins in the formation of foam cells in human pathology, particularly in hypertriglyceridemic subjects, the human monocyte-macrophage receptor from the monocytic cell line THP-1 were characterized and purified and receptor-specific antibodies were produced. Briefly, this unique apoE-and lipoprotein lipase-independent pathway and binding site is in murine macrophages, human monocytes and macrophages, and in the human monocytic cell lines THP-1 and U937, but not in human fibroblasts or hepatoma cell lines or in Chinese hamster ovary (CHO) cells (Gianturco, 1988, 1994a). Further, ligand blotting studies in bovine and porcine aortic endothelial cells also were positive. Thus, endothelial cells specifically bound chylomicrons followed by hydrolysis and uptake of their cholesteryl esters (Fielding, 1978) and very low density lipoproteins from hypertriglyceridemic subjects, but not from normal subjects, delivered cholesterol to cultured endothelial cells (Gianturco, 1980).

Since the apoE-independent and lipoprotein lipase-independent receptor also binds β-very low density lipoproteins, but with lower affinity, it was once referred to as a β-very low density lipoprotein receptor (Goldstein, 1980; Gianturco, 1986a). Subsequent studies, however, demonstrated that uptake of triglyceride-rich lipoproteins independent of apoE was not inhibited by anti-low density lipoprotein receptor antibodies that inhibited the low density lipoprotein receptor-mediated uptake of rabbit β-very low density lipoproteins in the same cells, nor did anti-low density lipoprotein receptor antibodies bind to the candidate receptor (Gianturco, 1988). The apoE-independent receptor differs from the low density lipoprotein receptor family or the scavenger receptor family in many properties including (1) unchanged expression during differentiation, (2) slower intracellular ligand degradation, (3) ligand specificity, (4) apparent molecular weight of the candidate receptors, and (5) cellular distribution.

The prior art is deficient in the lack of the sequence of the DNA encoding for the monocyte-macrophage apoB receptor gene and protein and in the understanding of its expression in the placenta, human coronary, carotid, and aortic macrophage-derived foam cells in atherosclerotic lesions and in other immune tissues including peripheral blood leukocytes, bone marrow, spleen, tonsils and appendix. The present invention fulfills this longstanding need and desire in the art.

SUMMARY OF THE INVENTION

Monocyte-macrophage-derived foam cells accumulate in atherosclerotic lesions and throughout the body in some types of hypertriglyceridemia. Uptake of plasma chylomicrons and hypertriglyceridemic triglyceride-rich lipoproteins by an apoE-independent human monocyte and macrophage receptor, distinct from previously-described lipoprotein receptors, may be involved in foam cell formation in vivo. Two cell-surface membrane binding proteins (MBPs) of ~200 and ~235 kDa, in human monocytes and macrophages and THP-1 monocytes and macrophages, were characterized as the likely receptors. It was determined that both MBPs share a common ~200 kDa ligand binding subunit. This ligand-binding subunit was purified and internal tryptic peptide sequences were obtained. Receptor-specific antipeptide antibodies were generated against a 10-residue unique and unambiguous internal sequence (to which no matches were found in GenBank, Swiss Pro, etc) that binds the active receptor forms MBP200, MBP200R and MBP235. Antibodies against the C-terminal ~47 kDa receptor domain and other domains were produced and shown to bind to all active forms of the receptor. Overlapping partial cDNAs from a λgt10 THP-1 library and from a λgt10 human placental library corresponding to the receptor were obtained and sequenced.

The present invention shows that cell-surface MBP200 and MBP235 are unique monocyte, macrophage, placental and endothelial cell receptors for apoB in plasma chylomicrons and some hypertriglyceridemic-triglyceride-rich lipoproteins and their remnants; other apoB-containing lipoproteins also bind to the receptor with varying, generally much lower, affinities. The present invention also shows that said receptors bind to apoB-48 and to the N-terminal portion of apoB-100 at or near the lipoprotein lipase binding site and not in a heparin-binding domain. Normally, the MBPs may be involved in nutrition of circulating monocytes and accessible, peripheral macrophages, e.g. bone marrow; in lipemic states, the pathway can be overwhelmed and contribute to foam cell formation and endothelial cell dysfunction. Therefore, diminished triglyceride-rich lipoprotein uptake by this receptor, due either to receptor defects or to triglyceride-rich lipoprotein defects leading to altered receptor affinity, may be involved with metabolic abnormalities associated with increased risk for cardiovascular disease, such as modest hypertriglyceridemia and small, dense low density lipoproteins (pattern B) and/or persistence of chylomicron-derived, (i.e., apoB-48-containing) lipoproteins in the fasting state. Diminished activity of the receptor in the placenta could result in fetal abnormalities due to reduced delivery of dietary fat-soluble vitamins (A, E, D) and essential fatty acids and other essential nutrients that are carried in chylomicrons.

To clone the cDNA for MBP200R, PCR with degenerate primers were used and a THP-1 λgt10 cDNA library to produce a 631 bp product (pcr631) (SEQ ID No. 3) which contains three peptide sequences found in amino acid sequence from MBP200R. pcr631 was used to identify several distinct cDNA clones. One clone, THP-1 λ73-3 (SEQ ID No. 9), contains an 1851 bp insert with a 1381 bp open reading frame (ORF) and 470 bp untranslated region including the stop codon, the polyadenylation signal and the poly-A tail. PCR on a 5' stretch human placenta λgt10 cDNA library using antisense primers derived from the 5' end of THP-1 λ73-3 resulted in a 1466 bp clone with an open reading frame that overlapped the open reading frame of THP-1 λ73-3 (pcr1466) (SEQ ID No. 8) resulting in a 3071 bp sequence with a 2601 bp open reading frame. Glutathione-S-transferase fusion proteins were expressed using the pcr631, THP-1 λ73-3, and pcr1466 pGEX constructs. Polyclonal antibodies were produced to each protein domain. Immunoblots demonstrate that the antibodies specifically recognize the GST-fusion products and all receptor activities (MBP200, MBP235 and MBP200R). Additional 5' sequence obtained by PCR of the human placenta λgt10 cDNA library with antisense primers from the 5' end of pcr1466 resulted in a 751 bp clone (pcr751) (SEQ ID No. 7) that contained the Kozak consensus start sequence in a 39 bp untranslated 5' end and the initial ATG start codon. The sequences obtained result in 3773 bases of cDNA sequence (SEQ ID No. 1) with an open reading frame of 3264 bp encoding a 1088 residue protein. Northern analysis of THP-1s, human placenta, bone marrow, peripheral blood leukocytes, spleen, tonsils, appendix, and lymph node reveal a messenger RNA of approximately 3.8 kb, indicating the complete cDNA sequence has been determined. A full-length cDNA was constructed in a pCDNA vector. Chinese hamster ovary (CHO) cells transfected with the vector containing the receptor cDNA, in contrast to the pCDNA vector alone, expressed full receptor activity as determined by rapid, high affinity binding and uptake of fluorescent DiI-labeled trypsinized VLDL and, in stably transfected CHOs, by rapid cellular triglyceride mass accumulation.

One object of the present invention is to provide an isolated DNA molecule encoding a monocyte-macrophage cell-surface binding protein selected from the group consisting of: (a) a DNA molecule comprising a sequence SEQ ID No. 1 and which encodes the monocyte-macrophage cell-surface binding protein (the apoB receptor) (SEQ ID No. 2) or a portion of the monocyte-macrophage cell-surface binding protein; and (b) a DNA molecule differing from the DNA molecule of (a) in codon sequence due to the degeneracy of the genetic code, and which encodes the monocyte-macrophage cell-surface binding protein (SEQ ID No. 2) or a portion of the monocyte-macrophage cell-surface binding protein. Embodiments of this object of the invention include provisions for a vector containing the isolated DNA molecule encoding a monocyte-macrophage cell-surface binding protein and regulatory elements necessary for expression of said isolated DNA molecule in a cell, the vector adapted for expression in a recombinant cell, as well as a host cell containing the vector.

An additional object of the present invention is to provide a vector comprising an isolated DNA for a monocyte-macrophage cell-surface GST fusion binding protein having the sequence SEQ ID No. 2 or portions thereof.

A further object of the present invention is to provide a method of cell-specific delivery of therapeutic compounds to human monocytes, macrophages, other reticuloendothelial cells that express the receptor or embryos comprising the steps of: providing a peptide or antibody(s) having the ability to bind to an isolated monocyte-macrophage cell-surface binding protein having the sequence SEQ ID No. 2, or a portion of said sequence or comprising a related protein of the same gene family; and incorporating the peptide into liposomes containing said therapeutic compound. Yet another method of cell-specific delivery may utilize a receptor-specific antibody or an antibody fragment (Fab) that binds to an isolated monocyte-macrophage cell-surface binding protein having the sequence SEQ ID No. 2, or a portion of the sequence, or comprising a related protein of the same gene family; and incorporating the antibody into liposomes.

Yet another object of the present invention is to provide a method of inhibiting foam cell formation and increased monocyte adhesion to endothelial cells, comprising the step of treating a monocyte-macrophage with an agent which binds an isolated monocyte-macrophage cell-surface receptor protein having the sequence SEQ ID No.2, thereby blocking or inhibiting binding of apoB-containing lipoproteins to the receptor. Gene therapy such as adenoviral delivery of the receptor proteins of the present invention to LDL-receptor deficient subjects is also contemplated.

Another object of the present invention is to provide delivery of the novel sequences disclosed herein, e.g., in an adenoviral vector, to the liver or elsewhere, for the purpose of correcting metabolic defects that cause abnormal accumulation of apoB-containing lipoproteins in the plasma.

Yet another object of the present invention is to provide a method of evaluating an individual at risk for cardiovascular disease, comprising the steps of: (a) extracting a sample of monocytes-macrophages and triglyceride-rich lipoproteins from the plasma of the individual and from a control individual not considered at risk for cardiovascular disease; and (b) comparing the binding affinity ($K_d$) of the apoB receptor of the monocytes-macrophages for triglyceride-rich lipoproteins between the individual at risk and the control individual, whereby a difference in the binding affinity between the individual at risk and the control individual is indicative of an alteration in either or both the apoB cell-surface receptor protein and triglyceride-rich lipoproteins, and the alteration in the apoB cell-surface receptor protein or triglyceride-rich lipoproteins is indicative of dyslipidemias, abnormal postprandial triglyceride metabolism or Pattern B phenotype in the individual at risk.

This objective may also be accomplished by performing a Western blot analysis on proteins of the monocytes-macrophages using an antibody directed towards the protein of SEQ ID No. 2, or fragments thereof, or alternatively performing a Northern blot analysis on RNAs of the monocytes-macrophages using a DNA probe selected from the group consisting of SEQ ID No. 1, SEQ ID No. 3, SEQ ID No. 7, SEQ ID No. 8 and SEQ ID No. 9, or fragments thereof, whereby a difference in the migration or mobility of the proteins and/or RNAs between the individual at risk and the control individual is indicative of an alteration in the apoB cell-surface receptor protein, and the alteration in the apoB cell-surface receptor protein is indicative of dyslipidemias, abnormal postprandial triglyceride metabolism or Pattern B phenotype in the individual at risk.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can be understood in detail, more particular descriptions of the invention may be had by reference to certain embodiments which are illustrated in the appended drawings. These drawings form a part of the specification. It is to be noted, however, that the appended drawings illustrate preferred embodiments of the invention and therefore are not to be considered limiting in their scope.

FIG. 7 shows the amino acid sequence derived from the 631 base pair PCR product. The carboxyterminal sequence (shaded) represents the peptide sequence used to produce the initial degenerate oligonucloeotide primer and is from the same peptide used to develop the anti-peptide antibodies and used for surface labeling of the THP-1 monocytes. The underlined peptides represent sequences found by tryptic peptide mapping and microsequence analysis of MBP200R.

DETAILED DESCRIPTION OF THE INVENTION

Figure 1A:
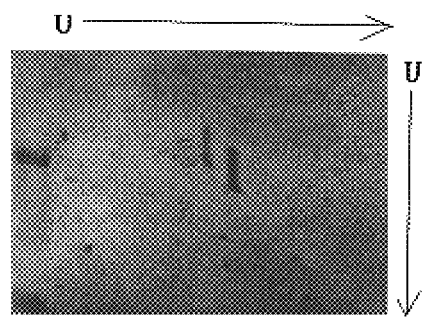
FIG. 1 shows a 2-dimensional SDS-PAGE of MBP200 and MBP235 before and after reduction. Detergent extracts of THP-1 monocytes were electrophoresed in the first dimension in a minigel without reduction. One cm strips containing the MBPs were removed and treated with buffer (panel A) or reductant, 2% 2-mercaptoethanol, (panel B), placed lengthwise on a second 5% slab minigel, electrophoresed and transferred to nitrocellulose for ligand binding analysis. Panel A illustrates that without reduction (U) MBP200 and MBP235 maintain their distinct mobilities (seen on the diagonal), whereas after reduction (R) in the second dimension, both activities now have identical Rfs that are different from their original Rfs. The reduced form of both receptor proteins that retain ligand binding activity was called MBP200R. The single lane on the far left of each 2-D gel contains internal prestained markers, at approximately 200 kDa and 97 kDa.

Two major triglyceride-rich lipoprotein membrane binding activities with apparent molecular weights of approximately 200 and approximately 235 kDa (MBP200 and MBP235) were identified by ligand blotting analysis in both normal human blood-borne monocyte-macrophages and the long term human THP-1 and U937 monocytes and macrophages. MBP200 and MBP235 are cell surface proteins that share a common backbone (MBP200) containing the ligand binding domain. MBP235 is comprised of MBP200 plus one (or more) small subunit(s) of ~35 kDa apparent total mass (as determined by mobilities on SDS-PAGE) that associate(s) noncovalently with MBP200, does not inhibit triglyceride-rich lipoprotein binding, and is immunochemically distinct from the receptor-associated protein (RAP), a 39 kDa protein that modulates ligand binding to low density lipoprotein receptor-related protein and other low density lipoprotein receptor family members (Strickland, 1990).

Amino acid sequence data obtained from tryptic peptides from purified MBP200R, the reduced ligand-binding subunit of the receptor, had no matches in gene and protein databases, indicating that MBP200 is a unique protein. The sequence data was used to produce antipeptide antibodies that were then found to bind solely to the MBP200, MBP235, and MBP200R receptors, thereby confirming that MBP200 is a unique protein. The receptor-specific antibodies also confirmed the structure, chemistry and relationships of MBPs obtained initially by biochemical and ligand blotting analyses.

The specific, apoE-independent binding of plasma chylomicrons and other apoB-containing lipoproteins to this monocyte-macrophage receptor, coupled with in vivo studies, suggests a role of this pathway in the nutrition of circulating monocytes and accessible macrophages, such as in bone marrow in the postprandial state. Moreover, anti-apoB blocking studies indicate this previously-undiscovered human monocyte-macrophage receptor binds triglyceride-rich lipoproteins via apoB. In addition, apoB-48 appears to be sufficient, and neither apoB-100 nor apoE is necessary for binding. This also suggests a new role for apoB-48; i.e., targeting plasma chylomicrons and their remnants to accessible monocytes and macrophages for uptake while still triglyceride-rich, before reaching the triglyceride-depleted, cholesteryl ester- and apoE-enriched remnant that is targeted by apoE to the liver for uptake by hepatic receptors which bind lipoproteins via apoE. A defect in this monocyte-macrophage receptor or in its ligands could result in aberrant triglyceride-rich lipoprotein metabolism (rerouting of chylomicrons for lipolysis and eventual liver uptake) that would lead to delayed chylomicron clearance and abnormal persistance of chylomicron remnants and/or small, dense low density lipoprotein. This condition has been termed Pattern B phenotype.

The Pattern B phenotype is expressed primarily in adults, is associated with increased risk of cardiovascular disease, and is inherited in an autosomal dominant or codominant manner with varying polygenic effects, including lipoprotein lipase deficiency, insulin resistance, apo CIII, and an as-yet, unidentified gene defect(s) (Krauss, 1994). Since candidate mechanisms for this phenotype include altered triglyceride-rich lipoprotein metabolism and clearance, the monocyte-macrophage receptor of the present invention is a candidate gene for one contributing cause of this pattern. The potential role of apo CIII in modulating the binding of triglyceride-rich lipoproteins to this receptor fits with the observation that CIII-enriched triglyceride-rich lipoproteins are found in Pattern B and that transgenic mice that overexpress CIII or CII are hypertriglyceridemic. The apoCs (especially CIII) could interfere with apoE-mediated uptake mechanisms and also mask the apoB domain(s) that bind to MBP200. Identification of genes related to this phenotype allows identification of subjects before the phenotype is expressed. As subjects with this phenotype are extremely responsive to changes in dietary fat (Krauss, 1994), early identification permits dietary intervention so as to delay atherogenic changes.

The experiments leading to the present invention addressed several interactions of triglyceride-rich lipoproteins with monocytes and macrophages and their relation to lipoprotein metabolism and foam cell formation. Such interactions include a) whether MBP200 and MBP235 are chylomicron/apoB-48 receptors; b) the molecular structure and function of MBP200; c) the structure and function of the small subunit(s) in MBP235 (such as chaperone(s)); d) whether MBP200 and MBP235 are restricted to monocytes, macrophages and endothelial cells; e) the receptor binding domains in apoB; and f) whether apoCIII and apoE modulate receptor binding.

The present invention provides a composition of matter comprising isolated DNA molecules encoding overlapping domains of the monocyte-macrophage and placental cell-surface binding protein and the full-length cDNA construct selected from the group consisting of: (a) a DNA molecule comprising a sequence SEQ ID No. 1 and which encodes the full-length cDNA of said monocyte-macrophage cell-surface binding protein (SEQ ID No. 2) or a portion of said monocyte-macrophage cell-surface binding protein domain of the sequence of the monocyte macrophage binding protein; and (b) a DNA molecule differing from the DNA molecule of (a) in codon sequence due to the degeneracy of the genetic code, and which encodes said monocyte-macrophage cell-surface binding protein (SEQ ID No. 2) or a portion of said monocyte-macrophage cell-surface binding protein; an isolated monocyte-macrophage cell-surface binding protein having the sequence SEQ ID No. 2; a method of cell-specific delivery of therapeutic compounds to human monocytes or macrophages, comprising the steps of: providing a peptide or antibody having the ability to bind to an isolated monocyte-macrophage cell-surface binding protein having the sequence SEQ ID No.2, or a portion of said sequence; and incorporating said peptide or antibody into liposomes containing said therapeutic compound or directly linking said peptide or antibody to therapeutic compound; and a method of inhibiting foam cell formation and increased monocyte adhesion to endothelial cells, comprising the step of treating a monocyte-macrophage with an agent which binds an isolated monocyte-macrophage cell-surface binding protein having the sequence SEQ ID No.2.

Further provided are methods of evaluating an individual at risk for cardiovascular disease using the compositions of matter provided herein for examining either the apoB receptor-ligand interaction, or the RNA and/or protein corresponding to apoB in an individual at risk as compared to a control individual, to determine the presence of any abnormalities in the apoB receptor of the individual at risk.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985);

"Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The oligonucleotides herein are selected to be "substantially" complementary to a particular target DNA or RNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene can be used to transform a host using any of the techniques commonly known to those of ordinary skill in the art. One preferred embodiment is the use of a vectors containing coding sequences for purposes of prokaryotic transformation. Prokaryotic hosts may include *E. coli, S. tymphimurium, Serratia marcescens* and *Bacillus subtilis*. Eukaryotic hosts include yeasts such as *Pichia pastoris*, mammalian cells, insect cells and plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

In addition, the invention also includes fragments (e.g., antigenic fragments or enzymatically functional fragments) of the apoB cell-surface receptor protein. As used herein, "fragment," as applied to a polypeptide, will ordinarily be at least 10 residues, more typically at least 20 residues, and preferably at least 30 (e.g., 50) residues in length, but less than the entire, intact sequence. Fragments of the apoB cell-surface receptor protein can be generated by methods known to those skilled in the art, e.g., by enzymatic digestion of naturally occurring or recombinant apoB cell-surface receptor protein, by recombinant DNA techniques using an expression vector that encodes a defined fragment of apoB cell-surface receptor protein, or by chemical synthesis. The ability of a candidate fragment to exhibit a characteristic of apoB cell-surface receptor protein (e.g., binding to an antibody specific for apoB cell-surface receptor protein, or exhibiting partial enzymatic or catalytic activity) can be assessed by methods described herein. Purified fragments of apoB cell-surface receptor protein or antigenic fragments of apoB cell-surface receptor protein can be used to generate antibodies by employing standard protocols known to those skilled in the art.

A standard Northern blot assay can be used to ascertain the relative amounts of apoB cell-surface receptor protein mRNA in a cell or tissue in accordance with conventional Northern hybridization techniques known to those persons of ordinary skill in the art. Alternatively, a standard Southern blot assay may be used to confirm the presence and the copy number of the gene encoding the apoB cell-surface receptor in transgenic systems, in accordance with conventional Southern hybridization techniques known to those of ordinary skill in the art. Both the Northern blot and Southern blot use a hybridization probe, e.g. radiolabelled apoB cell-surface receptor cDNA, either containing the full-length, single stranded DNA having a sequence complementary to SEQ ID No. 1, SEQ ID No. 3, SEQ ID No. 7, SEQ ID No. 8, SEQ ID No. 9 or a fragment of those DNA sequences at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The following examples are given for the purpose of illustrating various embodiments of the invention and are not meant to limit the present invention in any fashion.

EXAMPLE 1
Cells and Cell Extracts

Human monocytes are isolated by adhesion to plastic from peripheral mononuclear cells isolated on a Ficoll-Paque gradient (Boyum, 1968). The adherent cells (90–95% monocytes) are used after isolation or after 1–7 days culture in RPM1–1640 containing 20% autologous serum (Gianturco, 1994).

THP-1 monocyte-macrophages (ATCC) were grown in suspension in RPMI 1640 with 10% fetal bovine serum, 2 mM glutamine, 100 μg streptomycin and 100 units of penicillin/ml and $5 \times 10^{-5}$ M 2-mercaptoethanol. Cells were maintained in tissue culture flasks at 37° C. in a humidified atmosphere of 4% $CO_2$ and 95% air at $\leq 1 \times 10^6$ cells/ml. THP-1 monocytes differentiate into adherent macrophages when treated with $10^{-7}$ M phorbol 12-myristate, 13-acetate (PMA) (Hara, 1987; Gianturco, 1988). For differentiation, cells were seeded ($1.5 \times 10^6$ cells/35 $mm^3$ dish) in complete media; PMA was then added. Adherent cells were used for experiments between 1 and 7 days. Cellular triglycerides, cholesterol, and cholesteryl ester masses (Gianturco, 1986a) were determined as described. Human skin fibroblasts were early passage cells from newborn foreskin and maintained as described (Gianturco et al., 1978, 1980).

$1.5 \times 10^8$ THP-1 monocytes were harvested and washed twice with 50 mL of buffer A (0.15 M NaCl containing 50 U aprotinin/mL, 5 mM benzamidine, and 0.1 mM PMSF) and resuspended in 2 mL of 20 mM Tris, pH 8.0, 50 mM NaCl, 0.1 mM EDTA, containing the protease inhibitor mix of buffer A plus leupeptin and PPACK and solubilized with 1% Triton X-114 for 15 minutes on ice. Aqueous phase extracts were prepared as described (Gianturco et al., 1988, 1994; Ramprasad et al., 1995) by the method of Bordier (1985) and immediately frozen in liquid nitrogen after the addition of glycerol to a final concentration of 10% (v/v). Protein content was estimated by the Bradford method using the Bio-Rad Protein Assay reagent (Bradford, 1976).

EXAMPLE 2
Purification and Microsequencing of the MBP Protein

MBP200R was purified from 75 liters of THP-1 monocytes ($75 \times 10^9$ cells) by a four-step procedure, capitalizing on the unique properties discovered during other purification attempts, such as the relative resistance of MBP200 activity to heat and to reduction. Briefly, the purification scheme used to isolate the protein for microsequencing was: Triton X-114 aqueous-phase extracts were reduced with 2-mercaptoethanol to convert MBP200 and MBP235 to MBP200R and then heated (90–100° C.) for up to 10 minutes and centrifuged, which selectively eliminates ~90% of the contaminating proteins without significant loss of MBP200R ligand binding activity. The supernatant containing MBP200R activity was fractionated on DEAE and then hydroxyapatite, and finally resolved by preparative SDS-PAGE. The electroeluted MBP200R band appeared homogeneous by two-dimensional electrophoresis and silver staining. Starting at the extraction step, this represented approximately a 1200-fold purification, which reflects the difference between purification from pure cells and tissues. If one can obtain sufficient cells and stabilize the desired product, cultured cells are significantly enriched over a tissue source since there is no extracellular material. After transfer to Immobilon, strips containing MBP200R were processed for gas-phase microsequence analysis [City of Hope Microsequencing and Mass Spectrometry Core Facility]. Two independent attempts indicated that the N-terminus was blocked. Therefore, the protein was trypsinized on the membrane (0.1 M ammonium bicarbonate pH 8.0 and 10 pmole trypsin at 37° C. for 24 hours), the peptides eluted and separated by micro-LC-chromatography on a Vydac C18 column (530 μm ID) with a TFA/acetonitrile gradient; peaks were detected by UV monitoring and analyzed by mass spectrometry and microsequencing techniques.

Figure 4:
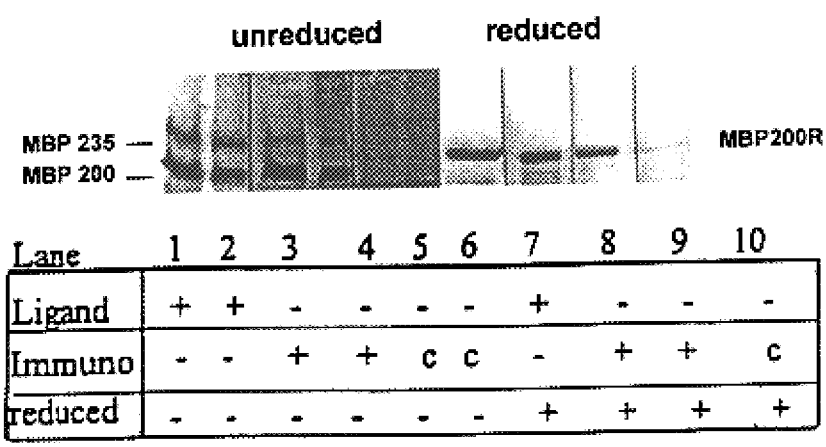
FIG. 4 shows that the ligand binding activity and antipeptide immunoreactivity are coincident before and after reduction of the MBPs, demonstrating that each MBP contains the 10-residue unique sequence obtained by microsequence data from peptides from purified MBP200R. C=preimmune sera at the appropriate concentration as control. Lanes 1–6 contain two levels of the THP-1 detergent extracts: lanes 1, 3 and 5 are a 1:3 and lanes 2, 4 and 6 are 1:5 dilution. Lanes 3, 4 and 8 are at 1:50 and lane 9 is at 1:100 dilution of the antipeptide antibody. Ligand binding activity was visualized by incubation with hypertriglyceridemic-very low density lipoproteins for 2 hours at room temperature and detected with anti-apoB antibodies. Primary antibody binding was then detected with Anti-IgG alkaline phosphatase conjugated antibodies.

Seven peptides contained sufficient mass and were sequenced; the most useful data were from peptide 29, a thirteen residue fragment in which 10 contiguous residues were unambiguously identified: E/L/A,A/L,Q/V/E, A,E,G,L,M,V,T,G,G,R (MH+=1333) (SEQ ID No. 5). Searches of peptide and nucleotide sequence databases revealed this was a unique sequence, as was peptide 18 (V/E,A/L,V,M,G,Q,M (SEQ ID No. 6)), useful for making oligonucleotides because of its 2 methionines. A peptide corresponding to the unambiguous portion of peptide 29 ((C)AEGLMVTGGR; (SEQ ID No. 10)) was synthesized in the peptide core at University of Alabama-Birmingham; the C-terminal arginine was amidated and the cysteine was added for coupling to keyhole limpet hemocyanin (KLH) and used for antibody production in rabbits. The first immunoblots of the first bleed were positive for all three active forms of the receptor (FIG. 4). Immunoreactivity perfectly coincided with ligand blotting activity in the native (MBP200 and MBP235), and upon reduction, tracked the electrophoretic mobility shift along with ligand blotting activity into the reduced form, MBP200R; preimmune antisera did not bind to these proteins, showing the antipeptide antibodies are specific for the MBPs. These data also confirm immunochemically the ligand blot data that showed that MBP235 contains MBP200 and that both are converted into MBP200R upon reduction. Antibodies generated against GST-fusion proteins representing various domains of MBP200R verified these results.

The immunoblotting/ligand blotting experiments were repeated with numerous THP-1 extracts and three different antipeptide antisera and affinity-purified anti-peptide antibodies and compared to extracts of other receptor positive and receptor-negative cells. Consistent with cell binding and ligand blotting studies, extracts of human U937 monocytes, but not human skin fibroblasts or CHO extracts, showed specific antipeptide immunoreactivity that coincided with ligand blotting activity. The antipeptide antibodies show that this unique sequence, AEGLMVTGGR (SEQ ID No. 5), unmatched in GenBank, is indeed from the major ligand binding subunit, MBP200. Thus, a unique protein that has all of the biochemical characteristics necessary for a monocyte and macrophage-specific triglyceride-rich lipoprotein receptor was purified.

EXAMPLE 3
cDNA Cloning and Characterization of MBP200 and MBP235

The protein/peptide microsequence data yielded two useful peptides from which oligonucleotides were generated. Since using highly degenerate oligos for screening cDNA libraries is not a simple task, an alternative PCR approach was sought to produce suitable probes for use in screening (Yokayama, 1993). The contiguous decapeptide sequence (obtained from a tryptic thirteen-residue fragment) was used to design nested, degenerate 17-mer oligonucleotide probes from the carboxyl-terminal end of the peptide and from the overlapping amino-terminal end. Using a THP-1 monocyte λgt10 cDNA library (Clontech) as template DNA, the carboxy-terminal primers were used in the first round of PCR with λ forward and reverse primers; the PCR products were fractionated over Qiagen columns to remove primers and subjected to a second round of PCR with the more amino-terminal degenerate primers and the λ forward and reverse primers. The second round yielded ethidium-bromide stainable products of about 150 base pairs in size. The products were subcloned into a pCRII vector using a TA cloning kit (Invitrogen) and into a pBluescript II vector. Sequencing by the dideoxy chain termination method indicated a clone with a 139 basepair open reading frame containing the decapeptide sequence.

Importantly, the DNA sequencing identified the first three residues of the peptide sequence unambiguously as Leu, Leu, Asp (Leucines were possible choices in the peptide microsequence analysis). This sequence, LLD AEGLMVTGGR (SEQ ID No. 5), correctly fits the mass spectral parent ion, MH+=1333, of the LC-isolated tryptic peptides). Importantly, the DNA sequence placed an Arg immediately before the Leu N-terminal residue of the sequenced peptide, which correctly predicts the trypsin cleavage site used to produce the peptide. Furthermore, that the same peptide sequence was used to produce an antipeptide antibody that correctly and specifically identified the intact MBPs was strongly supportive of the initial PCR results.

Based upon the PCR results, nondegenerate PCR primers were synthesized from the original nested primers and used with the λ primers in a new PCR protocol. PCR products of ~1 kb in size were produced and subcloned into the pCRII vector. pcr631 (SEQ ID No. 3) codes for three of the peptides obtained by microsequence analysis of tryptic peptide from MBP200R and correctly predicts Arg before each. FIG. 7 shows the predicted amino acid sequence derived from the 631 base pair PCR product (SEQ ID No. 4) and the 3 tryptic peptides are underlined.

Standard molecular biology approaches were used to clone and sequence the cDNA of MBP200 (Sambrook, 1989; Ausubel, 1987). Since MBP200 was isolated from THP-1 monocytes, a commercial λgt10 poly dT primed cDNA library from human THP-1 monocyte/macrophages (Clontech; Palo Alto, Calif.) was screened. The cDNA inserts range in size from 0.5–4 kb, with the average size around 1 kb. The amplified libraries contain approximately $1.4 \times 10^6$ independent clones, sufficient to include low abundance mRNAs. The expression libraries were screened by in situ plaque hybridization. The phage were plated on agarose-topped agar plates, and the plaques adsorbed onto duplicate nitrocellulose filters, denatured and probed with labeled oligonucleotides or partial cDNAs.

EXAMPLE 4
Expression of Unique MBPs in THP-1 Cells

Figure 6:
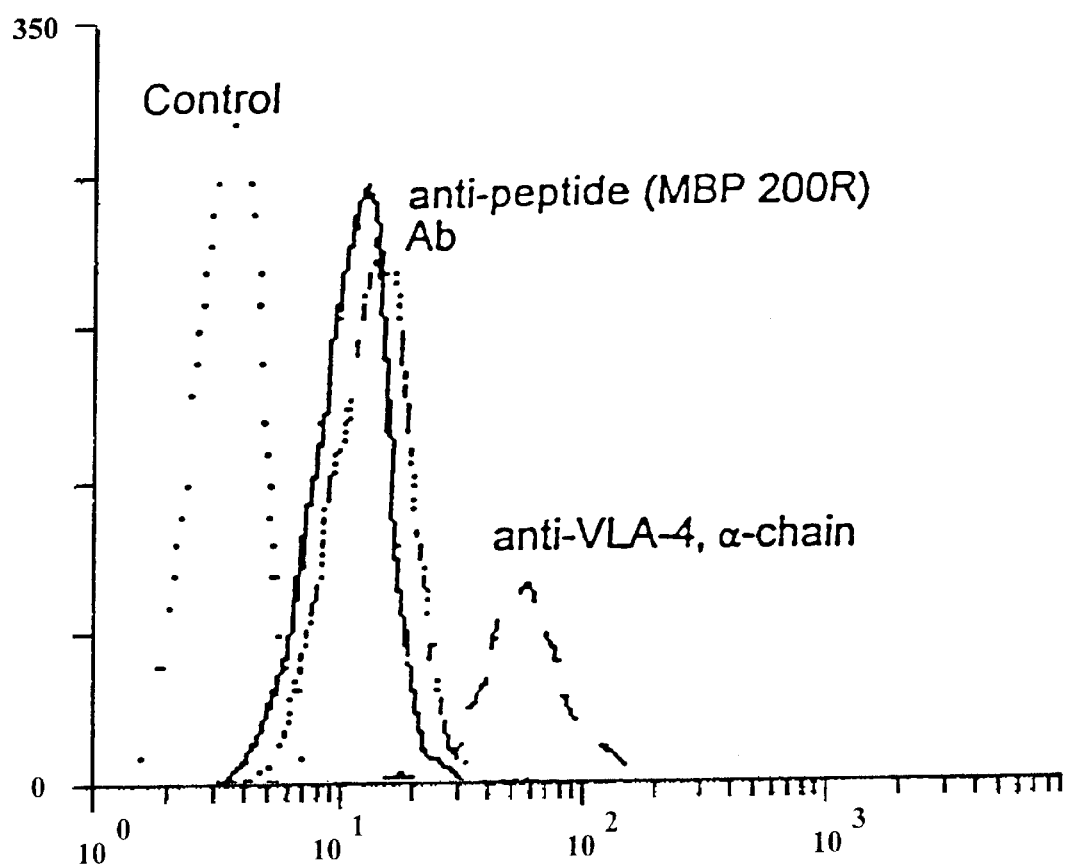
FIG. 6 shows the analysis of THP-1 monocytes by FACS. Antipeptide antibodies are shown to bind to the surface of THP-1 monocytes using two concentrations of the primary antibody. Goat(Fab')$_2$ rabbit anti-IgG (H+L)-FITC only (used as the negative control) and the alpha chain of the monocyte integrin VLA-4 was used as a known positive control.

Thus, the present studies demonstrate, as shown in FIG. 6, that THP-1 monocytes were surface-labeled with the affinity-purified anti-receptor antibody generated against a 10-residue synthetic peptide based on an unambiguous sequence of a tryptic peptide from purified MBP200R. Cell-surface location of this receptor epitope confirms that MBP200 and MBP235 are located on the cell surface, a criterion for a receptor of extracellular ligands.

A unique 631 basepair PCR product (pcr631) (SEQ ID No. 3) was generated, cloned, and sequenced from a λgt10 THP-1 monocyte library using oligonucleotide primers based on the same unambiguous tryptic peptide from MBP200R that was used to generate receptor-specific, antipeptide antibodies. The PCR631 product (SEQ ID No.3) contained an open reading frame (bp3-630) which predicts a unique 209-residue protein sequence (SEQ ID No. 4) that contains three of the tryptic peptides determined by microsequence analysis of purified MBP200R, and contains arginine residues before each of these three peptides, correctly predicting the trypsin cleavage sites in MBP200 needed to generate the microsequenced peptides (see FIG. 7). This is direct evidence that the THP-1 λgt10 library contains MBP200-specific cDNAs. Neither the 209-residue predicted protein sequence nor the determined 631 nucleotide sequence has any identities or close matches in the NCBI nonredundant peptide and nucleotide databases (PDB+ Swiss Prot+PIR+SPUpdate+GPUpdate+GenBank+ EmblUpdate+EMBL), confirming its uniqueness. PCR631 labeled with digoxigenin was used to identify receptor-specific clones from the THP-1 library for sequencing.

Figure 8:
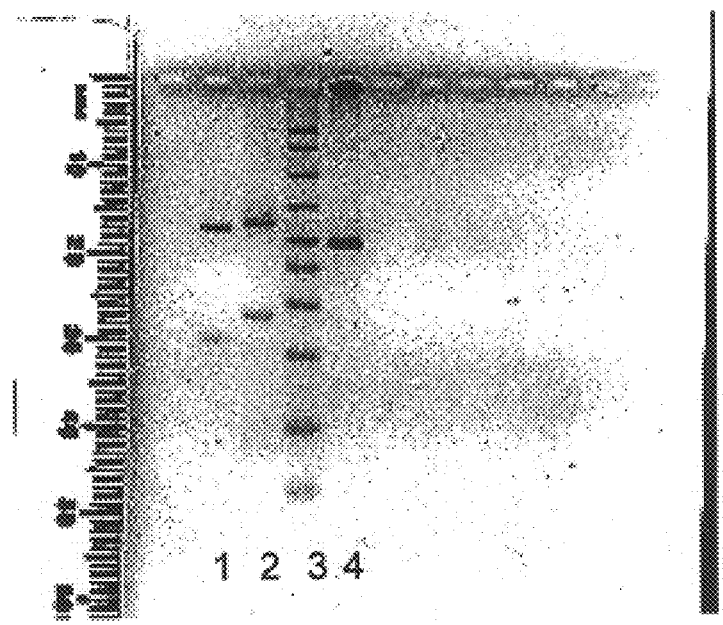
FIG. 8 shows that THP-1 monocytes contain mRNA coding for MBP200R. RT-PCR using primer pairs from the PCR631/MBP200R sequence and MRNA from THP-1 monocytes produced a RT-PCR product of the correct size. The ethidium bromide stained gel (inverse image) of the RT-PCR products is shown. Lane 1: 572 bp product using primers 53–72, sense and 624–604, antisense; Lane 2: Glucose-6-phosphate dehydrogenase (GPDH) control product; Lane 3: MW ladder; Lane 4: second round product generated with internal second antisense primer, 490 bp.
Figure 9:
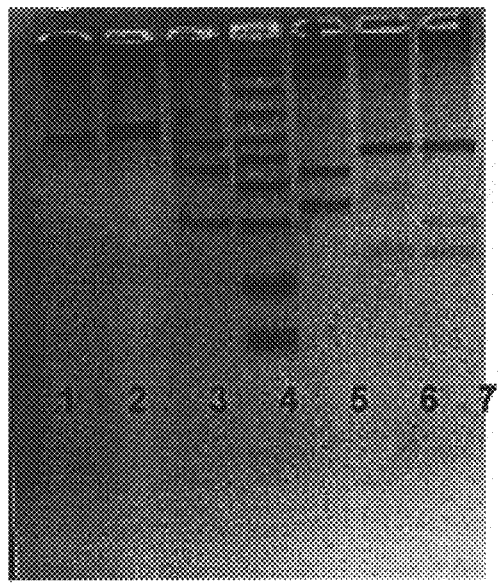
FIG. 9 shows the restriction mapping of the 572 bp RT-PCR product described in FIG. 8 (inverse image). Lane 1: 572 bp product; Lane 2: EcoRI control, no digestion; Lane 3: BamH1; Lane 4: MW ladder 50 bp, 100, 200, 300, 400, 500, 700, 1000, 1500 and 2000 bp; Lane 5: PstI; Lane 6: HindIII; Lane 7: XbaI.

Reverse transcriptase (RT)-PCR demonstrates that THP-1 monocytes contain mRNA coding for MBP200R. RT-PCR using primer pairs derived from the PCR631/MBP200R sequence and mRNA isolated from THP-1 monocytes produced an RT-PCR product of the correct size (FIG. 8, lane 1). Notably, a second round of PCR using an internal antisense primer produced a single, predicted 490 bp product (FIG. 8, lane 4), indicating the THP-1 cells from which MBP200R was purified do indeed express MBP200 mRNA (FIG. 8, digitized negative image of gel photo). Restriction-site mapping verified the sequence of the RT-PCR product, correctly producing the predicted-size fragments for BamHI, HindIII, PstI, and XbaI (FIG. 9, digitized negative scan of gel photo). This further confirms that the sequence of PCR631 (SEQ ID No. 3), which contains coding sequences for three tryptic peptides derived from MBP200R, and RT-PCR product sequences are correct.

The dig-labeled PCR631 probe was used to screen a THP-1 λgt10 library and eight receptor clones were identified (partials, ranging from ~1 to ~3 kb in length) from ~600,000 screened. A 3 kb clone was sequenced (λ73-3). The nucleotide sequence is unique. More 5' probes from this sequence were used to screen a human placenta λgt10 random primed library to obtain the complete cDNA. The sequence was confirmed by sequencing multiple clones.

Figure 18:
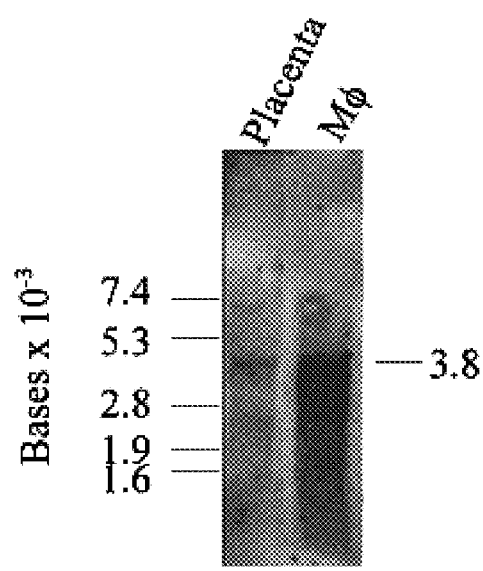
FIG. 18 shows the expression of the 3.8 kb TGRLP/ApoB Receptor mRNA in human placenta and THP-1 monocytes-macrophages.
Figure 19:
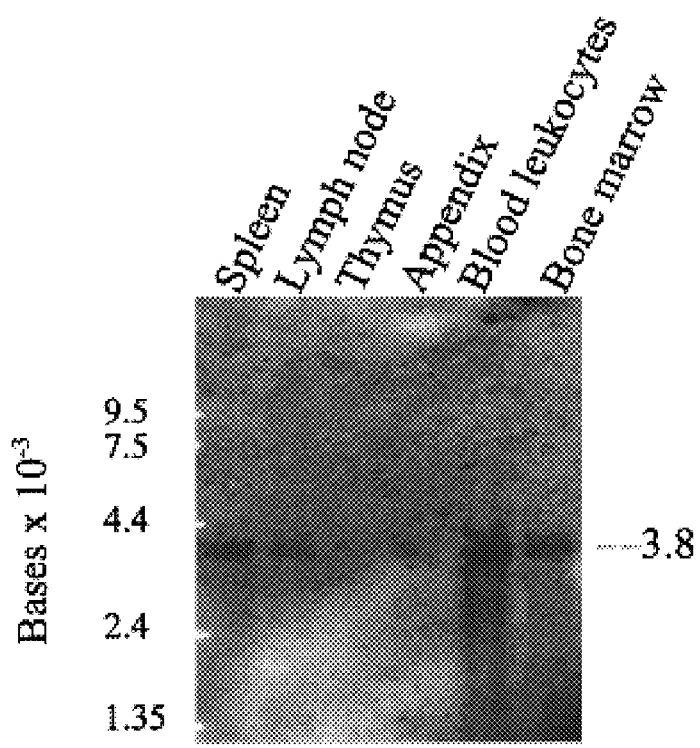
FIG. 19 shows the expression of TGRLP/ApoB Receptor mRNA in human immune tissues, including spleen, lymph node, thymus, appendix, blood leukocytes and bone marrow.
Figure 20:
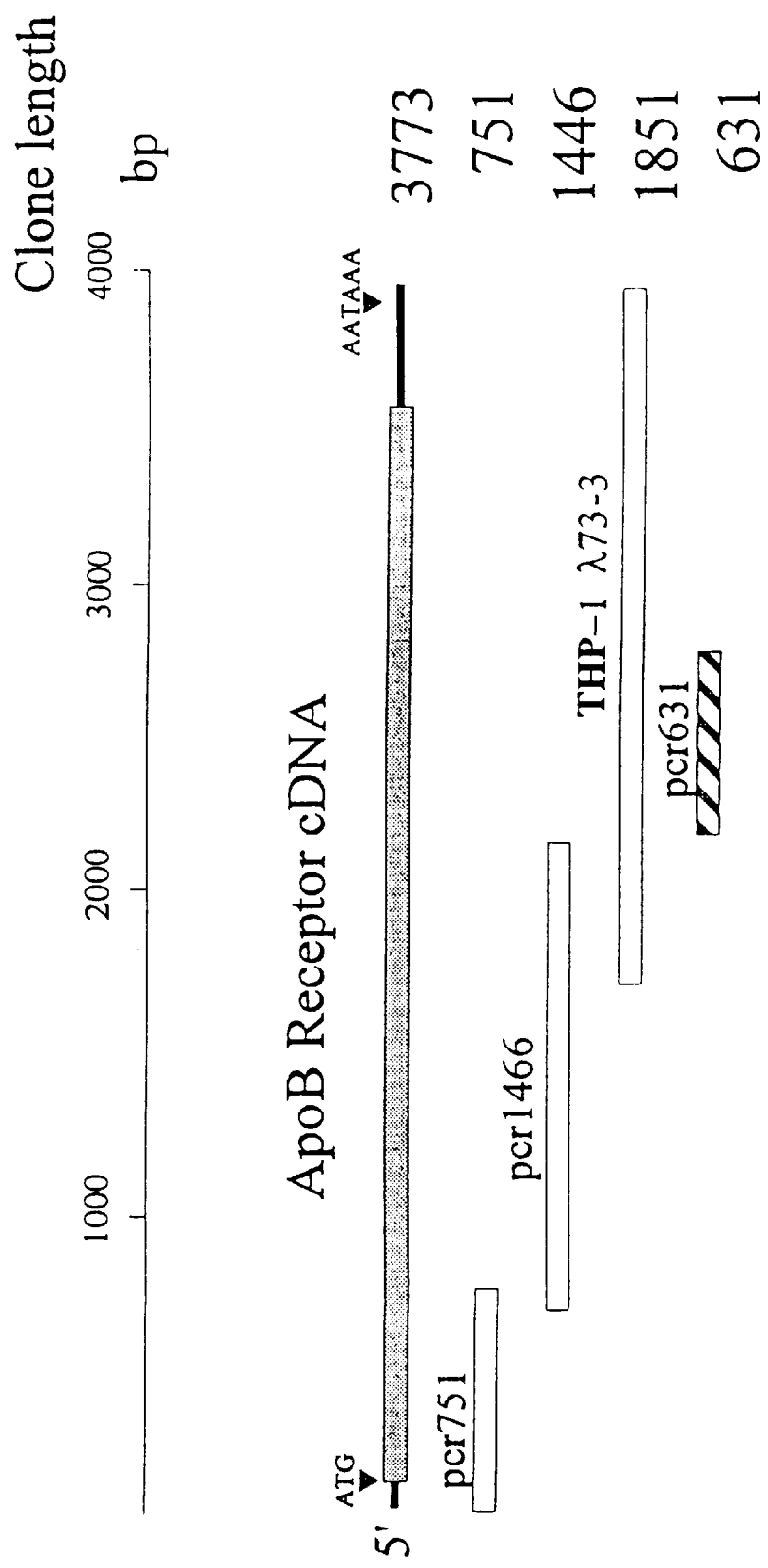
FIG. 20 shows the relative positions of the overlapping clones used to characterize the full-length human TGRLP/ApoB Receptor cDNA.

Reverse transcriptase experiments with PCR631-specific primers and murine P388D1 macrophages, human blood monocytes, human umbilical vein endothelial cells, and U937 monocytes, but not human skin fibroblasts or CHO cells, produced RT-PCR products of the correct size and with the same restriction sites, indicating that monocytic and endothelial cells, but not fibroblasts or CHO cells, contain mRNA for this receptor protein. These primers also produced a PCR product of the same size and with the same restriction enzyme sites from placental polyA mRNA and a λgt10 human placenta library, indicating this receptor mRNA is expressed in human placenta. Northern analysis revealed an mRNA of approximately 3,800 bases in RNA of human THP-1, placenta (FIG. 18), peripheral blood leukocytes, bone marrow, lymph nodes, tonsils, spleen, thymus and appendix (FIG. 19). This is in close agreement with the approximately 3,773 bases of the full-length cDNA construct.

EXAMPLE 5
Isolatation, Characterization and Location of the Gene Encoding MBP200

The isolation, characterization and chromosomal location of the MBP200 gene is determined in the following manner. Initially, the number of MBP200 genes in the human genome are determined. For this, human genomic DNA is digested with various restriction enzymes and probed by Southern blot analyses using various portions of the MBP200 cDNA. From the number of positive hybridizing bands for each digest, one can determine whether there is a single MBP200 gene, or if MBP200 belongs to a multigene family. The chromosomal location of MBP200 is probed by in situ hybridization of metaphase chromosomes. The latter analysis provides information on copy number if different members of the gene family are located on different chromosomes.

A human genomic library is screened by in situ plaque hybridization. Probes from both the 5' and 3' ends of the cDNA are used to ensure the isolation of overlapping genomic clones. Positive clones are isolated, and overlapping clones aligned by restriction endonuclease mapping and Southern blot hybridization. Selected regions of the gene encoding specific cDNA sequences are identified by blot hybridization, subcloned in a plasmid vector, and sequenced to identify individual genes.

Organization of exons and introns in the gene is determined by PCR amplification of human genomic DNA with a series of gene-specific primers, followed by cloning of the PCR products into TA vectors and sequence analysis of the inserts. Comparison of the gene sequence with that of the cDNA would directly establish the intron-exon structure of the gene. There are three introns within the coding sequence. The characterization of the gene from murine genomic libraries provides the basis for analysis of MBP200 function in transgenic and knockout mice. In addition, if MBP200 is a candidate gene for subclass Pattern B phenotype or other dyslipidemias or immune system pathologies, then the isolated MBP200 gene would be highly useful in obtaining probes for more refined linkage analysis as well as identifying putative mutations in the human genome. The gene is located on chromosome 16p11, as determined by FISH.

Small, dense low density lipoprotein (subclass Pattern B) is an independent, genetically determined coronary atherosclerosis disease risk factor (Krauss, 1994). Although the mechanism leading to the subclass Pattern B phenotype is unknown, one potential scenario may involve reduced clearance of chylomicrons by accessible macrophages by this receptor and the conversion of abnormally high levels of chylomicrons into remnants in plasma. The latter would be cleared by hepatocytes which would then down regulate hepatic LDL receptor and exacerbate the delayed remnant removal. The increased total hepatic uptake of chylomicrons remnants would increase the synthesis of apo-B containing particles, and, combined with the down regulation of low density lipoprotein receptor, could, in the presence of slightly elevated triglyceride-rich lipoproteins and cholesterol ester transfer proteins (CETPs), result in the conversion of normal low density lipoproteins to small, dense low density lipoproteins, resulting in the Pattern B phenotype. Since as much as 30% of chylomicrons may be taken up by bone marrow macrophages, alterations in MBP200 and triglyceride-rich lipoprotein uptake by macrophages may be involved directly in the generation of the subclass Pattern B phenotype. Thus, the MBP200 (or the associated 35 kD peptide) may be candidate gene(s) for this phenotype.

EXAMPLE 6
Lipoprotein Purification

Since the receptor-binding domains appear to be in apoB-48, postprandial triglyceride-rich lipoproteins of differing flotation classes were used to identify the domain and effects of particle size on expression. Lipoprotein isolation was as detailed (Gianturco, 1986b) from fresh plasma containing antioxidants and protease inhibitors. Very low density lipoprotein$_1$ ($S_f$100–400), very low density lipoprotein$_2$ ($S_f$60–100), and very low density lipoprotein$_3$ ($S_f$20–60) were isolated from very low density lipoprotein (d<1.006) by cumulative flotation and sterilized as described (Lindgren, 1972; Gianturco, 1986b). Chylomicrons and remnants of $S_f$>400 triglyceride-rich lipoproteins were subfractionated into $S_f$>3200, $S_f$1,100–3,200, and $S_f$400–1100 by cumulative flotation through a discontinuous NaCl gradient (Lindgren, 1972).

To isolate chylomicrons and remnants enriched in apoB-48, normal and hypertriglyceridemic volunteers, after a 12 hour overnight fast, eat within 10 minutes a meal of scrambled eggs, bread, cheese and a milkshake containing 60,000 U of aqueous vitamin A/m$^2$ body surface (Weintraub, 1987). The meal contains 50 g of fat/m$^2$ body surface, and 65% of calories as fat, 20% as carbohydrate, and 15% as protein, with 600 mg cholesterol/1,000 calories and a P/S ratio of 0.3. This meal was (1) well tolerated by all subjects, (2) caused a reproducible postprandial response, (3) gave equivalent gastric emptying rates in normal subjects and in patients, and (4) the vitamin A dose was shown to be well within the capacity of the intestine to absorb it (Weintraub, 1987). Subjects who previously volunteered in an ongoing study using this meal were asked to repeat the fat load and blood was isolated at peak lipemia (as determined previously) to obtain postprandial triglyceride-rich lipoproteins for the isolation of apoB-48-containing particles.

Figure 15:
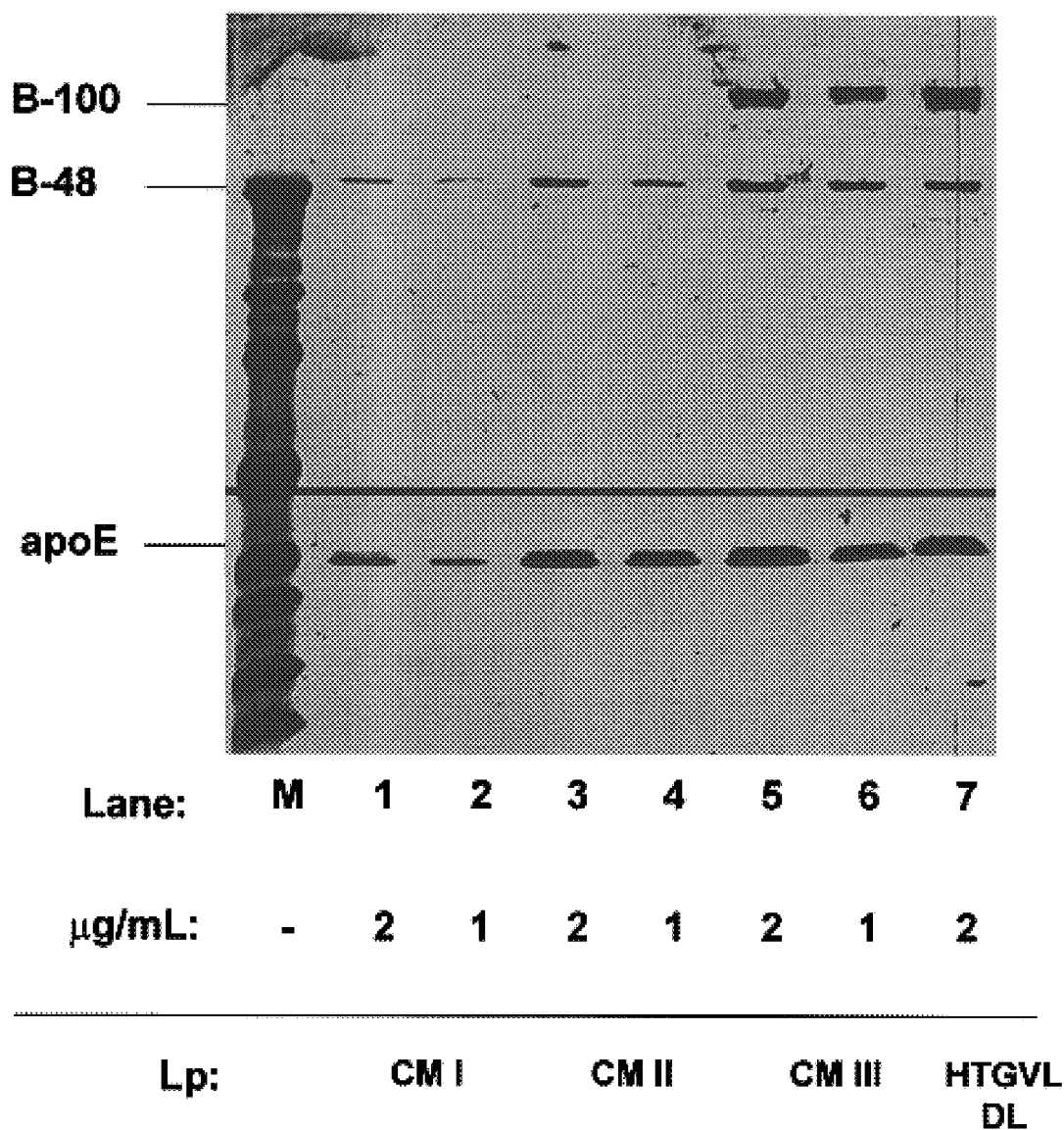
FIG. 15 shows immunoblots that demonstrate that plasma chylomicrons of $S_f$>1100 contain apoB-48 but not apoB-100. Plasma was isolated from a hypertriglyceridemic subject 4 hours after a standardized test fat meal. Total chylomicrons $S_f$>400 were subfractionated through a salt gradient into 3 subclasses: $S_f$>3200 (CM I), $S_f$1100–3200 (CM II), $S_f$400–1100 (CM III). These were electrophoresed at two levels of each (1 and 2 μg total apoprotein/lane) on a 4–20% SDS-PAGE, transferred to nitrocellulose, and probed for apoB (above the line) and apoE (below the line). CM I, lanes 1 and 2; CM II, lanes 3 and 4; and CM III, lanes 5 and 6; and control hypertriglyceridemic VLDL $S_f$100–400, containing apoB-100 and apoB-48 and apoE, in lane 7; lane M=prestained protein molecular weight markers.
Figure 16:
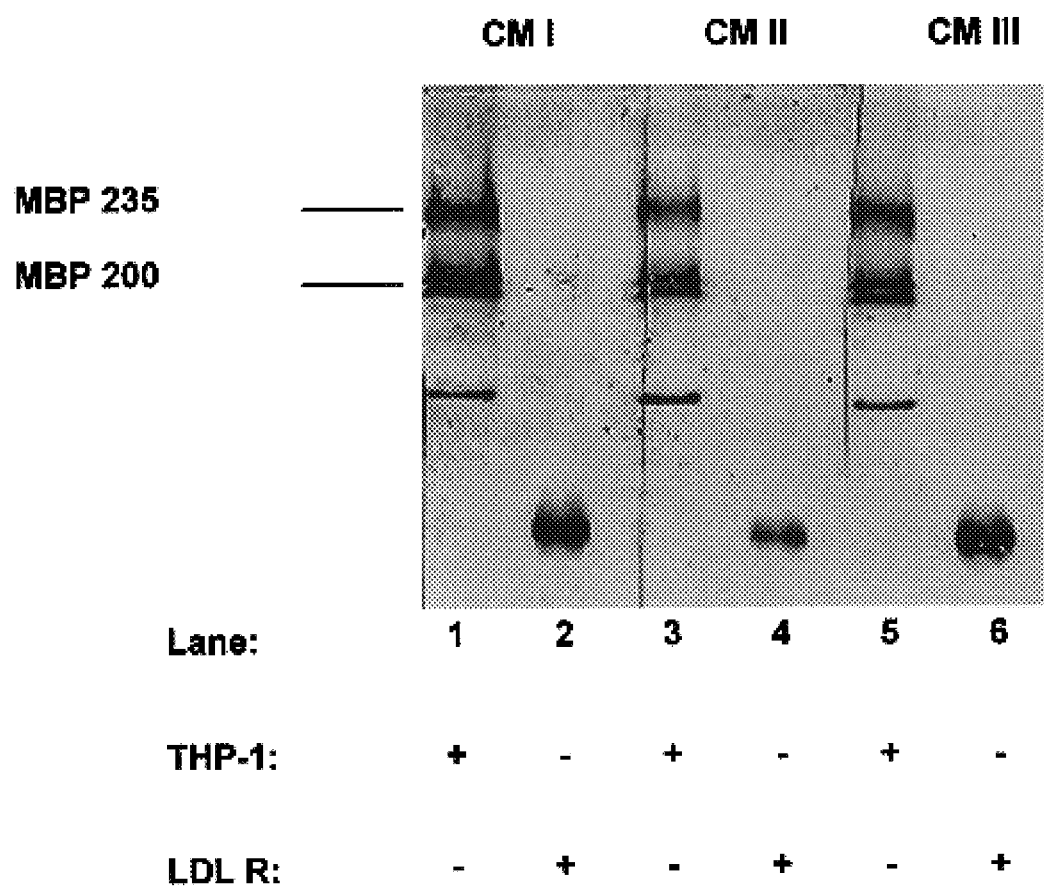
FIG. 16 shows the binding of chylomicron subspecies to MBP200 and MBP235 (odd lanes) or to the partially purified LDL receptor (even lanes). THP-1 monocyte aqueous phase extracts and the partially purified bovine LDL receptor were electrophoresed in alternating lanes, transferred to nitrocellulose, blocked, and incubated with chylomicron subfractions (10 μg/mL). CM I ($S_f$>3200) were incubated with lanes 1, 2; CM II ($S_f$1100–3200) with lanes 3, 4; and CM III ($S_f$400–1100) with lanes 5, 6. Binding was detected with a polyclonal anti-apoB antibody followed by a second antibody linked to alkaline phosphatase. The sharp band in lanes with THP-1 extracts that migrates between MBP200 and the LDL receptor is a nonspecific lipoprotein binding protein apparent in some but not all ligand blots.

Plasma chylomicron remnant fractions of $S_f$>3200 and $S_f$1100–3200 contained apoB-48 as the only apoB species (FIG. 15) and bound to the MBPs with high affinity (FIG. 16). This binding was inhibited by anti-apoB antibodies (FIG. 17), showing that apoB-48 is sufficient to mediate binding to the MBPs and apoB-100 is not necessary. Postprandial triglyceride-rich lipoproteins of different $S_f$s are separated into apoB-48 enriched particles by immunoaffinity chromatography using a monoclonal antibody that binds apoB-100 but not apoB-48 (JI-H) (Havel, 1992) and can be used directly. ApoB-100 particles bind and can then be eluted (Havel, 1992). The purified apoB-100-only (isolated both fasting and postprandially) and apoB-48-enriched subspecies are used in cell binding and ligand blotting studies to show that particles containing apoB-48 primarily, as well as only apoB-100, bind to the receptor. At peak lipemia, there were at least 3 mg protein of triglyceride-rich lipoprotein subfractions/dl in four subjects with normal fasting triglyceride levels. Immunochemical blots demonstrated that apoB-48 comprised 30–50% of the total apoB at peak lipemia. The apoB-48 particles were present in all subclasses, even at 8 hrs postprandially (even in the $S_f$20–60 fraction). There were >6 times more of each subclass in hypertriglyceridemic subjects than in normal subjects. So there are at least 900 µg of each apoB-48 triglyceride-rich lipoprotein subclass from normal subjects from 100 ml of plasma at peak lipemia. Anti-CIII immunoaffinity columns using polyclonal antibodies provided subfractions depleted (unbound fraction) versus enriched (bound) in Apo CIII.

Protein concentrations of the lipoproteins were obtained by a modified Lowry procedure with 0.1% SDS (Lowry et al., 1951; Helenius et al., 1971). Trypsinized-VLDL, reisolated and devoid of immunochemically detectable apoE, was prepared as described (Gianturco et al., 1983, 1986; Bradley et al., 1984). Functional loss of apoE was demonstrated by lack of binding of tryp-VLDL to partially purified bovine LDL receptors on ligand blots (Gianturco et al., 1983, 1988, 1994; Bradley et al, 1984; Gianturco and Bradley, 1986). Although tryp-VLDL is devoid of immunochemically detectable apoE and apoCIII, it retains essentially all immunochemically detectable apoB in fragments of 100 kDa and less as determined by SDS-PAGE (size) and RIA or by SDS-PAGE and quantitative dot blot analysis of parent VLDL and tryp-VLDL (Ramprasad et al., 1995).

EXAMPLE 7
Lipoprotein Modifications, Production of Model Very Low Density Lipoproteins and Lipoprotein Binding Assays Proteolytic degradations (Gianturco, 1986b) were as described. Chemical modifications such as acetylation, reductive methylation, maleylation, succinylation of lysines, cyclohexandione modification of arginine and its reversal were done (Means, 1971; Basu, 1977). Modification of lysine $\epsilon$-$NH_2$ by acetylation or by reductive methylation had no effect on binding to MBP200 or MBP235, but these procedures blocked binding to the LDL receptor and enhanced binding to the scavenger (acetyl LDL) receptor.

ApoB, apoE and apoCs were quantified by SDS-PAGE densitometric methods and for integrity by Western blotting (Gianturco, 1983). Cholesterol, cholesteryl esters, triglycerides, and phospholipids were quantified enzymatically (Boehringer Mannheim kits). Total phosphorus was determined as described (Bartlett, 1959).

Intralipids are subfractionated by cumulative flotation to remove PL-rich (smaller) particles with 2.5% glycerol included to stabilize the large particles (Bradley, 1986). Defined lipids are used to make more physiological very low density lipoprotein models with triglycerides, cholesteryl esters, cholesterol, and specific phospholipids (Miller and Small, 1983). The triglyceride-rich particles are incubated with desired apoproteins/synthetic fragments at room temperature for 2 hours and reisolated by cumulative flotation. Defined model very low density lipoproteins are constructed with and without desired apoproteins, synthetic peptides, and fragments. Native and specific protease-generated apoB fragments are solubilized in 1% octylglucoside to prepare model very low density lipoprotein by the dialysis method, as done successfully with low density lipoprotein-size lipid emulsions and apoB (Ginsburg, 1984). Model studies pinpoint protein components involved in receptor binding and were used to show that apoE is sufficient and apoB is not necessary for binding of large triglyceride-rich lipoproteins to the low density lipoprotein receptor (Bradley, 1986a).

Lipoproteins were iodinated as reported (Bilheimer, 1972; Gianturco, 1986b) and samples were filtered immediately before use. Specific activities ranged from 100–200 cpm/ng protein. Less than 10% of the label was extracted into organic solvent. Lipoprotein binding studies were carried out essentially as described by Goldstein and Brown (1974). THP-1 monocytes were seeded in 6-well tissue culture plates ($1.5 \times 10^6$ cells/well) and phorbol ester ($10^{-7}$ M) was added to induce adherence (Gianturco et al., 1994; Ramprasad et al., 1995). As controls, cultured human skin fibroblasts were subcultured and grown to ~75% confluency (3–4 d after subculture at a 1:4 split ratio) in complete medium [Dulbecco's modified Eagles (DME) containing 10% NuSerum, 2 mM glutamine, 100 μg streptomycin/mL and 100 U penicillin/mL], washed with sterile saline, and preincubated in DME containing 5% LPDS for 36 h to induce the LDL receptor (Gianturco et al., 1982). Cells were then preincubated for 30 min at 4° C. to cool the cells. Cells were then incubated with RPMI-1640 (THP-1 cells) or DME (fibroblasts) containing 10 mM HEPES (pH 7.4), 2 mg BSA/mL, and indicated amounts of $^{125}$I-HTG-VLDL or $^{125}$I-tryp-VLDL alone and in the presence of 200 μg/mL unlabeled VLDL or other potential competitors for 1.5 hours at 4° C. prior to extensive washing with cold buffered saline containing 2 mg BSA/mL (Goldstein et al., 1974) as described (Gianturco et al., 1982, 1983, 1988, 1994, 1986; Ramprasad et al., 1995; Bradley et al., 1984). Cells were dissolved in 0.1 N NaOH prior to the measurements of cell-associated radioactivity and cell protein. Dishes with no cells were used to correct for the amount of nonspecific binding to the plastic wells, as described (Gianturco et al., 1986). Duplicate dishes of cells were incubated with a range of concentrations of each lipoprotein, alone and with excess unlabeled lipoprotein to calculate specific binding at 4° C. (Gianturco, 1982a,b). Triton X-114 solubilization of human monocytes and macrophages plasma membranes were as described (Gianturco, 1988, 1994).

EXAMPLE 8

Antibodies and Antibody Production

Since MBP200 and MBP235 did not biochemically or immunochemically resemble other low density lipoprotein-like receptors or the acetyl low density lipoprotein receptor (they do not cross react with antibodies against the bovine low density lipoprotein receptor or the human low density lipoprotein receptor-related protein), it was necessary to purify the protein. Several tissue sources were examined and the highest activities were found in human monocytes and macrophages, which are a limited source. Thus the human TBP-1 monocyte cell line was used as a source for purification, since it grows continuously in suspension with a doubling time of ~60 hours, has identical binding proteins to human monocytes and macrophages, and has higher activities than the U937 human monocytic line.

After many attempts at ligand-affinity steps with various triglyceride-rich lipoprotein subfractions, both modified and native, a scaled-up two-dimensional electrophoresis procedure to obtain sufficient, partially purified MBP for monoclonal antibody production was used. Briefly, binding activity from plasma membrane preparations made from 2 billion THP-1 monocytes was solubilized with octyl glucoside. Solution phase isoelectric focusing (IEF) (Rotofor apparatus) was performed. The IEF fractions containing binding activity were concentrated and purified by preparative SDS-PAGE and transfered to nitrocellulose or Immobilon. Binding activity was identified by ligand blotting; strips with activity were cut out for implantation in mice. Binding activity of MBP235 was lost after IEF, although MBP200 remained active and was used for monoclonal antibody production. Approximately 2,400 hybridomas and 1,000 single cell clones were screened by two methods: immunochemical blotting and an immunoprecipitation, followed by ligand blotting, to detect loss of MBP200 binding activity. Only IgMs were generated and they had very low affinities for native MBPs. Although they immunoblotted, when coupled to Sepharose, the IgMs failed to bind MBP200 in solution. The fact that only IgMs were produced suggested that the antigen was monocyte-macrophage specific and/or an essential, highly conserved protein.

Polyclonal antisera of high titer specific for apoB (both commercial and laboratory generated) were used (Bradley, 1984). Five polyclonal rabbit antisera to human apoE for RIA and blotting (Bradley, 1984; Gianturco, 1983) were generated and used, as was a mapped monoclonal antibody against apoB. Mab JI-H, which binds to apoB-100 but not to apoB-48, was also used (Havel, 1992).

Sheep anti-human apoB IgG (1001400, Boehringer Mannheim, Indianapolis, Ind.) was purified by affinity chromatography using an LDL-conjugated Sepharose column prepared as described (Schneider et al., 1982). Immunoaffinity purified rabbit anti-sheep IgG conjugated to alkaline phosphatase and sheep gamma globulin were purchased from Jackson Labs (West Grove, Pa.). Rabbit anti-human apoB antibodies were isolated by ammonium sulfate precipitation of serum from rabbits immunized intradermally with human LDL, isolated at d=1.03–1.05 g/mL, and emulsified in adjuvant. The anti-apoB-100 antibodies generated and/or affinity purified were monospecific for apoB and did not recognize apoE, apoCs, or apoHDL. Anti-apoE was generated in rabbits using human apoE purified and was monospecific for apoE. Affinity purified goat anti-apoCIII and anti-apoCII were gifts from Dr. Ronald Krauss and Dr. G. M. Anantharamaiah, respectively.

EXAMPLE 9
Ligand Blotting

The ligand blotting assay was performed essentially as described (Gianturco et al., 1988, 1994; Ramprasad et al., 1995) with minor modifications. Aliquots of the detergent extracts were electrophoresed on 5% polyacrylamide gels containing 0.1% SDS (Laemmli, 1970) under non-reducing conditions in a Bio-Rad minigel apparatus and electrotransferred to nitrocellulose. After blocking for 1 hour with 5% Carnation nonfat dry milk in ligand buffer (50 mM Tris-HCl (pH 8), 90 mM NaCl and 2 mM $CaCl_2$), the blots were rinsed with 0.5% milk in ligand buffer before incubation with lipoproteins in ligand buffer containing 0.05% milk (Gianturco et al., 1988).

For competitive ligand blots, TGRLP were biotinylated as described (O'Shannessy et al., 1984) and dialyzed extensively before use. Biotin-labeled lipoproteins (with and without antisera), IgGs (the 50% $[NH_4]_2\ SO_4$ precipitate of antisera), or other potential competitors were preincubated for 30 minutes at 4° C. and then incubated with the nitrocellulose strips for 1.5–3 hours as indicated. After extensive washing, bound lipoprotein was detected by incubation with streptavidin linked to alkaline phosphatase, followed by substrates BCIP and NBT (Bio-Rad Laboratories, Calif.). In some experiments without antibodies as potential competitors, native, unlabeled TGRLP were used as the ligand, and bound TGRLP was detected with anti-apoB followed by alkaline phosphatase-linked secondary antibody. Ligand blots were scanned on an optical scanner (Hewlett-Packard, Atlanta, Ga.) and binding activity was quantitated using the Image Quant software (Molecular Dynamics densitometer, Sunnyvale, Calif.) as described (Gianturco et al., 1994; Ramprasad et al., 1995).

EXAMPLE 10
Membrane Binding Proteins (MBPs) for Triglyceride-rich Lipoproteins Direct binding studies at 4° C. demonstrate that human monocyte-macrophages, 1–6 days after isolation from blood, and human THP-1 monocytic cells, before and up to 7 days after differentiation with phorbol ester, exhibit a high affinity ($K_d$ 3–6 nM), saturable, specific, apolipoprotein E-independent binding site for the uptake and degradation of certain triglyceride-rich lipoproteins. Trypsinized-very low density lipoprotein (tryp-very low density lipoprotein) was used as the surrogate ligand to test for the apoE-independent triglyceride-rich lipoprotein binding site. This is because tryp-very low density lipoprotein binds to the macrophage specific binding site and MBPs for hypertriglyceridemic-very low density lipoproteins (Gianturco, 1988, 1994), but does not bind to low density lipoprotein receptors or to related receptors either in cells (Gianturco, 1983; Bradley, 1984) or in ligand blots (Brown, 1986) due to the absence of apoE or apoE fragments in tryp-very low density lipoproteins (Gianturco, 1983; Bradley, 1984). Tryp-very low density lipoproteins do not bind to other lipoprotein receptors, such as those in the scavenger receptor pathway (Gianturco et al., 1988, 1994). Notably, tryp-very low density lipoproteins retain essentially all of the parent very low density lipoproteins' immunochemically detectable apoB, in fragments of ~100 kDa and less. Use of ligands with mutually exclusive receptor specificities simplifies the interpretation of comparative and competitive binding studies by reducing the ambiguity seen when hypertriglyceridemic-very low density lipoprotein is used, since hypertriglyceridemic-very low density lipoprotein also binds to the low density lipoprotein receptor via apoE (Gianturco, 1983). Moreover, the absence of apoE in tryp-very low density lipoprotein would reduce the potential binding to other members of the low density lipoprotein receptor gene family that bind via apoE, such as low density lipoprotein receptor-related protein (Beisiegel, 1989; Kowal, 1989; Kowal, 1990) and the related very low density lipoprotein receptor (Takahashi, 1992). Studies were conducted at 4° C. in prechilled, washed cells to preclude secretion of apoE or other confounders, such as lipoprotein lipase, which modulate/mediate lipoprotein binding to the low density lipoprotein receptor family members. In addition, the medium contained no serum components to avoid adding any apoE that could be in lipoprotein-deficient serum (LPDS).

Ligand blots identified two membrane binding proteins of apparent MW of approximately 200 and approximately 235 kDa (MBP200 and MBP235) in both cell types. The MBPs share the same ligand specificity as the cellular site and bind dietary plasma chylomicrons $S_f$>400 from normal subjects, hypertriglyceridemic very low density lipoprotein, and the surrogate ligand trypsinized very low density lipoprotein devoid of apoE (tryp-very low density lipoprotein). The MBPs do not bind with high affinity low density lipoproteins, acetyl low density lipoprotein or normal very low density lipoprotein. Neither lipoprotein lipase nor apoE are required for triglyceride-rich lipoprotein binding to the cells or the isolated MBPs. The cellular binding site and the MBPs are expressed at similar levels at all stages of differentiation, unlike the low density lipoprotein or the acetyl low density lipoprotein receptor. Triglyceride-rich lipoproteins, which bind to the MBPs, induce rapid, saturable cellular triglyceride accumulation in monocytes as well as macrophages; normal very low density lipoprotein does not. In addition, the cell binding site and MBP200 and MBP235 are not affected by the media sterol content, unlike the low density lipoprotein receptor. Taken together, these data indicate that human monocytes and macrophages exhibit a high affinity, saturable, specific, ApoE- and lipoprotein lipase-independent binding site and MBPs for triglyceride-rich lipoproteins which differ in expression, specificity, and molecular size from receptors of the low density lipoprotein receptor gene family or the acetyl low density lipoprotein receptor (Gianturco et al., 1994). The characteristics of MBP200 and MBP235 suggest that they are candidates for the receptor-mediated, apoE-independent uptake of hypertriglyceridemic-very low density lipoprotein and chylomicrons by monocytes and macrophages. Therefore, MBP200 and/or MBP235 may be involved in cellular nutrition or, when overwhelmed, in foam cell formation.

EXAMPLE 11
Triglyceride-rich Lipoprotein Receptors with Unique Properties

Protease and heparinase susceptibility studies demonstrate that (1) these MBP activities have essential protein components, but not heparan sulfate proteoglycan components; (2) the MBPs are located on the cell surface; (3) heparan sulfate proteoglycans do not facilitate triglyceride-rich lipoprotein binding to this specific cellular site (Ramprasad et al., 1995).

To determine protease effects on the high affinity, apoE-independent cell binding sites, THP-1 macrophages were treated with RPMI-1640 alone (control) or with 3 μg pronase/ml at 37° C. for 40 minutes prior to the binding studies at 4° C. These conditions have been shown to have no effect on cell growth, but to alter cell surface receptors (Burger, 1970; Goldstein & Brown, 1974). The cell and ligand conditions used precluded potential ambiguities introduced by alternate lipoprotein pathways. Pronase pretreatment of cells significantly reduced the binding of $^{125}$I-tryp-very low density lipoprotein by 50–65% compared to controls (viability>95%). Recovery of the binding of triglyceride-rich lipoprotein to cells (>80%) occurred within 2 to 4 hours after the pronase-treated cells were washed and further incubated at 37° C. in complete medium prior to assessment of binding at 4° C. Ligand blots demonstrated that THP-1 monocytes treated with 3 μg pronase/ml for 40 minutes at 37° C. lost approximately 50–60% of their MBP200 and MBP235 activities, as compared to control cells. After the 4 hour recovery period in complete media, total MBP activities in control and pronase-treated cells were equal and somewhat greater than seen immediately after treatment, in parallel with the kinetics of recovery of triglyceride-rich lipoprotein binding to cells. Thus, proteolysis experiments establish the cell surface location of both MBPs. The parallel pronase-induced loss and subsequent recovery of MBP binding activity and cellular binding of triglyceride-rich lipoprotein strongly support their role as triglyceride-rich lipoprotein receptors.

Protease susceptibility did not rule out the possibility that the activities were proteoglycans. Moreover, others have reported that proteoglycans, specifically heparan sulfate proteoglycan, augmented and/or facilitated lipoprotein binding to the low density lipoprotein receptor (Mulder 1992), to low density lipoprotein receptor-related protein (Nykjaer, 1993), and to the very low density lipoprotein receptor (Takahashi, 1994). Heparinase treatment of THP-1 extracts had no effect on either MBP activity in ligand blots, indicating these MBPs are not themselves heparan sulfate proteoglycans. Likewise, there was no decrease in the total, nonspecific, or specific binding of hypertriglyceridemic-very low density lipoprotein or tryp-very low density lipoprotein to THP-1 macrophages pretreated with active heparinase prior to 4° C. binding studies. The heparinase experiments demonstrated that neither MBP200 and MBP235 nor the equivalent cellular triglyceride-rich lipoprotein binding site were heparan sulfate proteoglycan.

EXAMPLE 12
Effects of Reduction on MBP200 and MBP235

The LDL receptor, LDL receptor-related protein and the VLDL receptor have multiple cysteine-rich domains which comprise their complex ligand binding domains and specificities. The low density lipoprotein receptor loses activity upon reduction (Daniel, 1983) and the other lipoprotein receptors would be expected to lose binding activity upon reduction. For example, the scavenger receptor's trimeric structure (MW~260 kDa) could be selectively reduced with thiols to active monomers, but upon exhaustive reduction, all ligand binding activity was lost (Via, 1992). In contrast, reduction of MBP200 and MBP235 generated a new active species, MBP200R, which retained full activity even under exhaustive reduction conditions (boiling in 100 mM DTT or 5% 2-mercaptoethanol (2-ME)). In addition, although disulfides were present in both MBPs (both mobilities changed upon reduction), these disulfides were not essential for ligand binding activities.

Figure 1B:
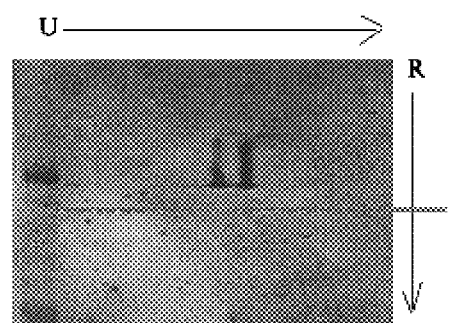

To demonstrate that MBP200R arose from both MBP200 and MBP235, two-dimensional (2-D) SDS-PAGE was used to separate the MBPs on the basis of size, both before and after reduction with 2-ME. In three independent experiments, both MBP200 and MBP235, in the absence of reduction in the second dimension, retained their original, distinct mobilities and activities (FIG. 1A, seen on the diagonal). In contrast, upon reduction in the second dimension, both MBP200 and MBP235 mobilities were altered relative to the ~200 kDa standard, and migrated with identical mobilities (seen off the diagonal), intermediate between MBP200 and MBP235, (FIG. 1, panel B) (Ramprasad et al., 1995). This demonstrates unequivocally that MBP200R arises from both MBP200 and MBP235. These changes in electrophoretic mobility reflect reduction of intramolecular disulfide bonds and, in the case of MBP235 where its electrophoretic mobility increased upon reduction, the possible loss of a small subunit(s) not involved in ligand binding. These conclusions were confirmed with receptor-specific antibodies.

EXAMPLE 13
Ligand Binding Affinities of MBP200, MBP235 and MBP200R

Figure 2A:
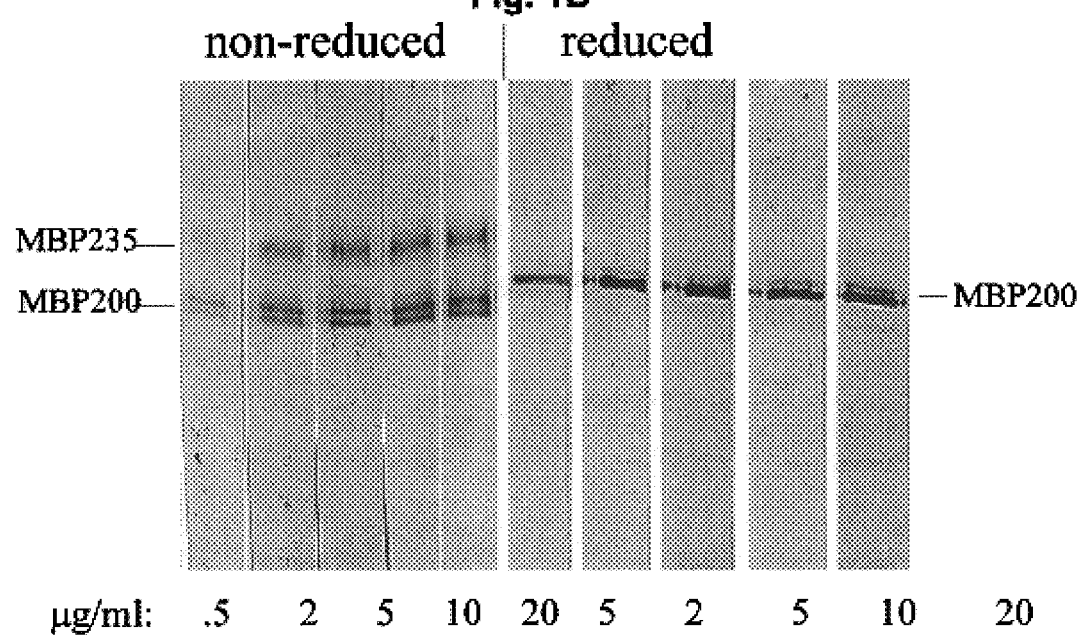
FIG. 2 shows (2A) ligand binding of MBPs by ligand blot analysis. Concentrations of the hypertriglyceridemic-very low density lipoproteins are given below each lane before (non-reduced) and after (reduced) treatment with 2-mercaptoethanol. Very low density lipoprotein binding was detected by apoB antibodies followed by IgG-specific enzyme-linked antibody and colorimetric substrate. Densitometry and quantification of the images utilized ImageQuant software.
FIG. 2B shows the saturation binding of hypertriglyceridemic-very low density lipoprotein to MBP235, MBP200 and MBP200R. The amount of very low density lipoprotein bound to MBP200, MBP235 and MBP200R activities in FIG. 2A was determined by densitometry of each MBP region in the ligand blots using a calibration curve generated from known amounts of the same very low density lipoprotein applied to nitrocellulose and quantified with a purified anti-apoB antibody. The amount of ligand bound to each MBP region, expressed as ng very low density lipoprotein bound, was plotted as a function of the amount of very low density lipoprotein to which the nitrocellulose was exposed. The broken line represents the calculated sum of binding of the very low density lipoprotein to MBP200 and MBP235 at each level of very low density lipoprotein.
FIG. 2C shows the data from FIG. 2B after transformation plotted by the method of Scatchard to determine the $K_d$ for each of the MBPs, expressed as µg/ml.

The 2-D experiments proved that both MBP235 and MBP200 are converted into MBP200R upon reduction. The ligand binding properties of each MBP was measured before and after reduction by quantitative ligand blotting analyses detected with anti-apoB antibodies and quantified by scanning densitometry (Ramprasad et al., 1995). MBP200 and MBP235 exhibited similar, high affinity saturable binding, with saturation occurring between 5 and 10 μg apo very low density lipoprotein/ml (FIGS. 2A&B). Scatchard analyses of the data indicate that MBP200 and MBP235 have similar $K_d$s of 1.6 and 2.2 μg apo very low density lipoprotein/ml and $B_{max}$ of 96 and 66 ng apo very low density lipoprotein/ mg cell protein, respectively (FIG. 2C).

Figure 2B:
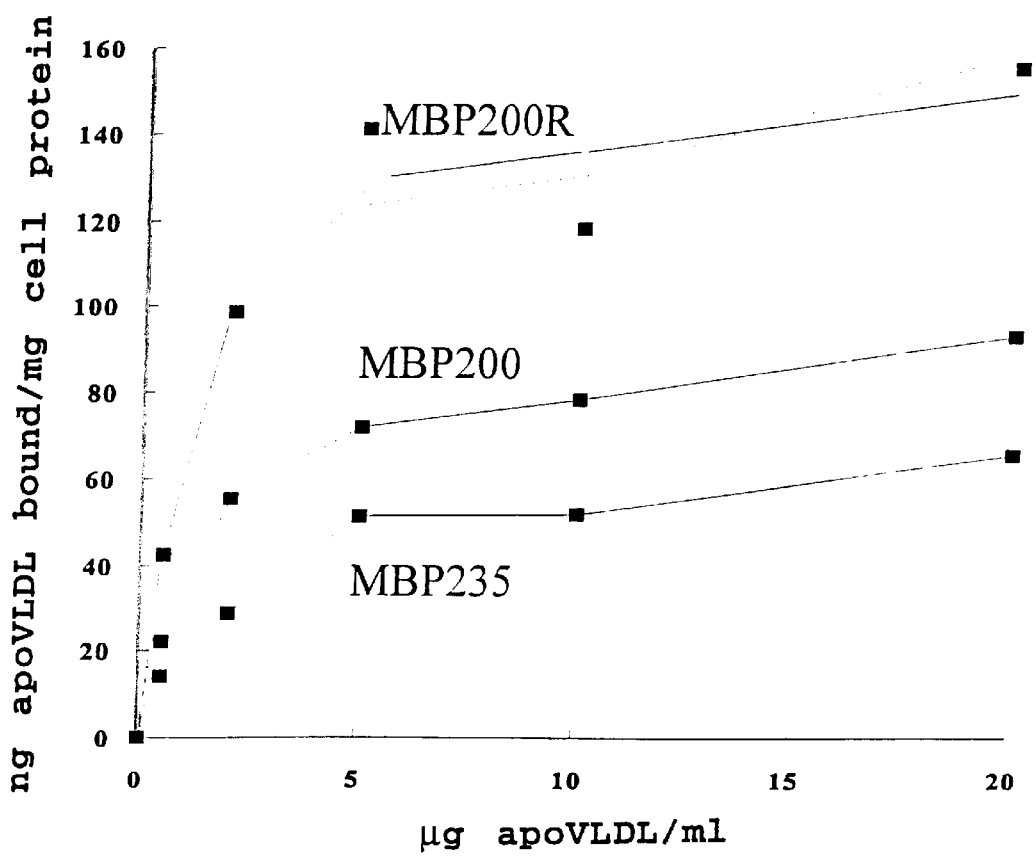
Figure 2C:
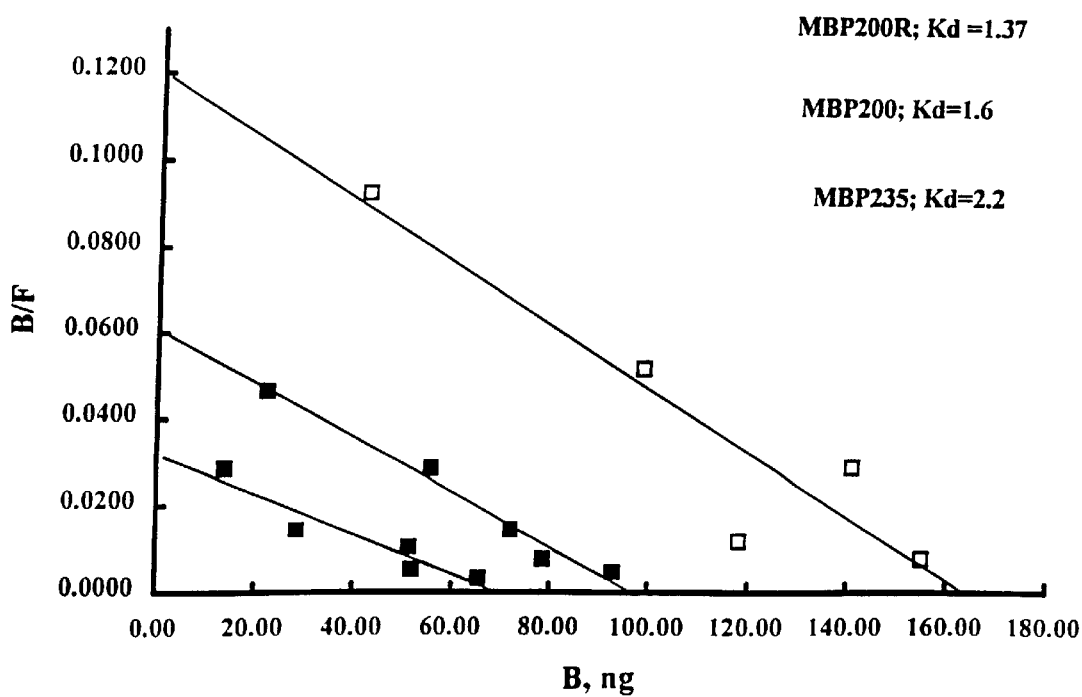

The binding of hypertriglyceridemic-very low density lipoprotein to MBP200R exhibits similar, high affinity, saturable binding with a $K_d$ of 1.4 μg/ml and a $B_{max}$ of 160, approximately equal to the sum of the maximal binding activities of its precursors, MBP200 and MBP235 (FIG. 2C). Indeed, the theoretical curve (dashed line) obtained by adding the amount of very low density lipoprotein bound to MBP200 and MBP235 at each level of lipoprotein is nearly superimposable on the measured binding curve for MBP200R (FIG. 2B). The binding affinities of hypertriglyceridemic-very low density lipoprotein and tryp-very low density lipoprotein for the MBPs were similar to their binding affinities for intact human blood-borne and THP-1 monocytes and macrophages, where $K_d$ of 2–4 μg apo very low density lipoproteinlml were determined (Gianturco, 1994). This striking similarity in ligand affinities provides additional supporting evidence that these MBPs are responsible for the apoE independent, high affinity and saturable binding of triglyceride-rich lipoproteins to monocytes and macrophages.

EXAMPLE 14
Thermal Conversion of MBP235 into MBP200 Binding Activity

The reduction data indicated that MBP200 and MBP235 share a common protein component of approximately 200 kDa, which retains all the ligand binding activity. Since the mobility of MBP235 increased upon reduction, this suggested that one or more small subunits may be present in MBP235 and lost, either due to reduction of an intermolecular disulfide bridge(s) or by an allosteric process caused by the disruption of the intramolecular disulfides during reduction of the 200 kDa protein. At 65° C., MBP235 was converted into MBP200 without loss of total binding activity, suggesting heat dissociates a small subunit(s) not required for ligand binding from a common large protein subunit that binds triglyceride-rich lipoproteins. Thus, MBP235 can be converted into MBP200 with full retention of ligand binding activity. Moreover, these data suggest that MBP235 has (a) noncovalent subunit(s) of approximately 35 kDa total mass that is/are lost upon heating or disruption of the intramolecular cystines of the parent backbone shared by MBP235 and MBP200. Additionally, the subunit(s) is/are not involved directly in triglyceride-rich lipoprotein binding.

Figure 3:
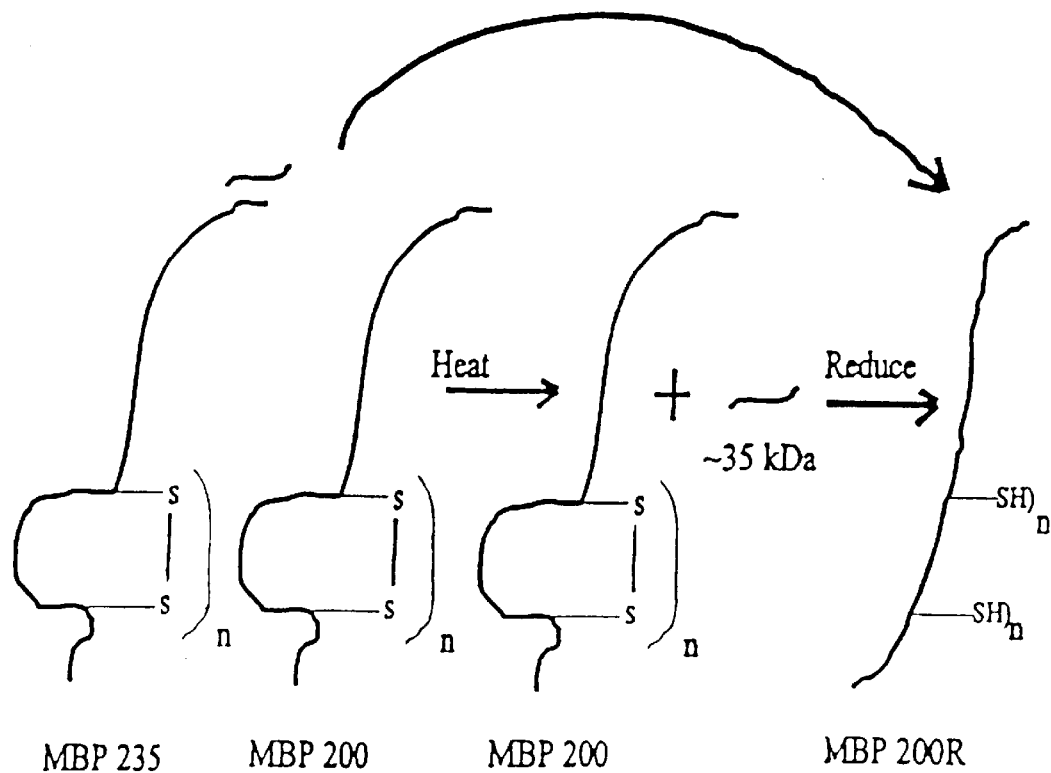
FIG. 3 shows a model of the relationship between MBP235 and MBP200 and how MBP200R is generated from MBP200 and MBP235 by treatment with reducing agents such as 2-mercaptoethanol.

In a working model (FIG. 3), MBP235 is comprised of two subunits, MBP200 and a ~35 kDa subunit, consistent with its apparent molecular weight on SDS-PAGE. The MBP235 complex dissociates upon heating into the active MBP200 subunit and an inactive smaller subunit(s). Upon reduction, the MBP235 complex also dissociates, losing its smaller subunit, and its active MBP200 component is extended by the reduction of intramolecular cystines, yielding an active binding protein (MBP200R) with a slightly slower migration, intermediate between MBP235 and MBP200 mobilities. MBP200 lacks the associated subunit (s), has saturation binding characteristics like those of MBP235, and upon reduction, is extended due to loss of its intramolecular disulfide bonds, yielding a product with identical electrophoretic mobility as that produced by reduction of the MBP235 complex. The model thus emphasizes the conclusion that a large and similar, if not identical, protein backbone is common to both MBP200 and MBP235 and contains the ligand binding domain(s). This suggests that the ligand binding domain(s) are not located either in domain(s) involved in the structural changes that occur upon reduction, or in domains that bind to the putative 35 kDa subunit. The conclusions reached from the reduction and heat-dissociation studies based on ligand blotting analyses have been confirmed using the antipeptide antibodies derived from MBP200.

EXAMPLE 15
Expression of MBP200 Confers Receptor Activity on Receptor-negative Cells The reconstruction and sequence characterization of the MBP200 cDNA has been completed to determine the primary structure of this unique protein and to express the protein in receptor-negative cells (CHO, fibroblasts, COS). This process examines (1) if MBP200 is sufficient for receptor function; (2) if MBP200 possesses functional ligand binding domains; and (3) whether the effects of receptor expression on the cellular binding and uptake of triglyceride-rich lipoproteins is independent of macrophage-associated apoE and/or lipoprotein lipase. Eight cDNA clones were identified in the THP-1 library and four in the placenta library. The MBP cDNA was reconstructed from overlapping cDNAs by the direct ligation of appropriate restriction fragments. Isolation of the full-length cDNA was verified by comparing its size (3773 bases) to the size of the mRNA (about 3.8 kb), and verified by the complete sequencing of the cDNA.

The complete characterization of the cDNA provides information necessary for expressing the protein in vitro and for the characterization of the corresponding gene. Characterization of the cDNA also provides information on the primary structure of the protein, the potential functional binding domain of the protein and possibly the relationship of the 35 kd subunit(s) to MBP200, as it is possible that the subunit is derived by post-translational proteolysis as has been shown for the low density lipoprotein receptor-related protein (~600 kDa=520+85 kDa).

Obtaining a full-length MBP200 cDNA allows the functions of the protein in vitro in receptor-negative cells to be shown in detail. The MBP200 cDNA was cloned into a pCDNA vector downstream of the cytomegalovirus promoter and transfected with a selectable marker gene (neomycin) into receptor-negative cells (CHO). Stable and transient transformants are then selected with G-418, and mass cultures and specific clonal lines examined for receptor activity by incubation with DiI-labeled tryp-very low density lipoprotein. Uptake of the fluorescent label by cells transfected with pCDNA plus receptor cDNA, but not by cells transfected with the pCDNA vector alone, demonstrates that the cDNA is sufficient to confer full receptor activity, and hence, the plasma membrane targeting of the receptor. The number of gene copies incorporated into stable transformants can be determined and MBP expression evaluated. Using both cDNA and antibody probes, the expression of both the mRNA and proteins, as well as the membrane targeting of MBP200, is determined. By comparing the size of MBP expressed in vivo to the protein synthesized by cell translation in vitro, one can obtain information on the intracellular processing of MBP200 and determine if the 35 kD protein is proteolytically derived from MBP200. For the latter analysis, messenger RNA corresponding to MBP200 is synthesized by run-off transcription using either T7 or T3 RNA polymerase in the presence of pGppG.

As receptor function is evident from expression of the DNA encoding MBP200, characterization of the protein domains involved in ligand binding can also be determined. 5'-deletion and site-directed mutants are constructed and expressed in stably transformed receptor-negative cells. By examining plasma membrane targeting and stability of the protein using the antibodies against MBP200, one can identify domains of the proteins important for ligand binding.

In addition, as receptor function is mediated by MBP200 alone, increased expression of MBP200 should increase triglyceride-rich lipoprotein uptake and downregulation should diminish uptake. MBP200 is placed under tetracycline (tet) regulation using a minimal CMV promoter fused to tet operator (O) sequences (tetO-CMV) in cells expressing a hybrid, tet-controlled transactivator (tetTA, the tet repressor DNA binding domain fused to the transactivation domain of VP16 from HSV that is essential for transcription). TetTA stimulates tetO-CMV promoters in the absence of tet (Gossen and Bujard, 1992). Tet binds to tetTA with high affinity and prevents its binding to the tetO-CMV promoter, thereby silencing the promoter. Varying the concentration of tet allows down-regulation of gene expression by up to 5 orders of magnitude. Thus, using such a system, one can examine the effect of expression of MBP on triglyceride-rich lipoprotein uptake and determine if there is a direct dose-dependent effect on uptake. To obtain receptor-negative cell lines expressing the tetTA, stable transformants containing plasmids encoding tetTA and the hygromycin-resistance gene are isolated, and lines expressing tetTA and capable of regulating a transfected reporter gene driven by tetO-CMV selected. These are also now commercially available. The receptor-negative, tetTA-expressing cell lines are then transfected with MBP200 driven by the tetO-MV promoter with a neomycin resistance gene, and neomycin-, hygromycin-resistant cells selected. Transformants are examined for the expression of MBP200, ligand binding and triglyceride-rich lipoprotein uptake in the absence (full expression) and presence of varying tet concentrations to control the degree of downregulation. Alternatively, other regulatable promoters (e.g. metallothionein) can be used.

EXAMPLE 16
The Smaller MBP200-associated Subunit(s)

The ~35 kD protein(s) associated with MBP200 does not appear to be the receptor-associated protein described (Strickland, 1990). Three lines of evidence for this conclusion include: (1) rabbit anti-human receptor-associated protein antibodies did not exhibit cross-reactivity with MBP235 in immunoblots, while readily detecting purified human receptor-associated protein and free receptor-associated protein in extracts of human skin fibroblasts and THP-1s; (2) receptor-associated protein did not associate with MBPs following ligand blotting under conditions where receptor-associated protein binds to members of the low density lipoprotein receptor gene family; and (3) receptor-associated protein did not compete for hypertriglyceridemic-very low density lipoprotein binding to MBP200 or MBP235, even when in 1000-fold molar excess, but readily competed for the binding of this ligand to the low density lipoprotein receptor. It is highly likely, therefore, that the 35 kD protein (s) corresponds to a unique MBP-associated protein.

EXAMPLE 17

Ligand Identification

Figure 5:
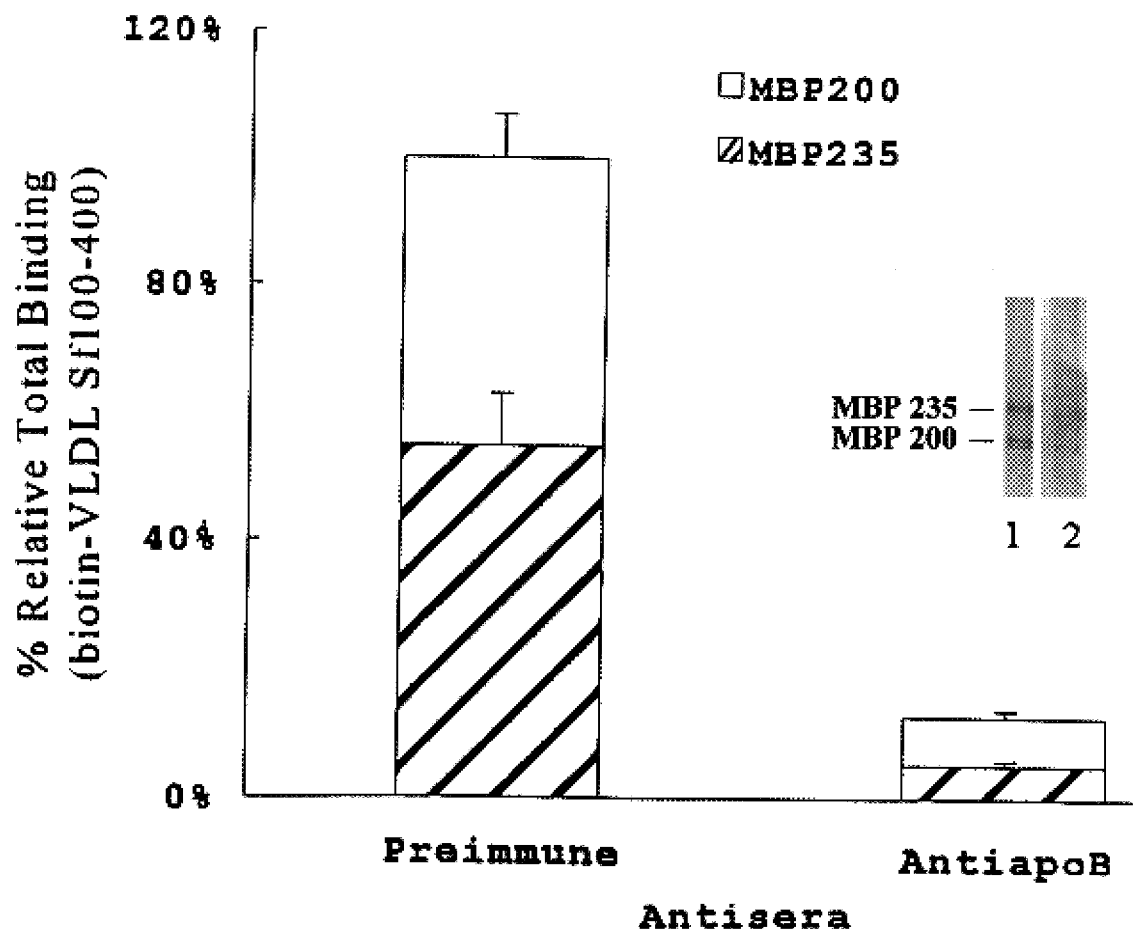
FIG. 5 shows that anti-apoB antibodies block binding of triglyceride-rich lipoproteins to MBP200 and MBP235. Biotinylated very low density lipoproteins were incubated for 0.5 hour with anti-apoB antibodies, lane 2, or with preimmune serum, lane 1, prior to ligand blotting for 1.5 hours. Biotinylated very low density lipoprotein binding was detected with streptavidin-alkaline phosphatase. The blots were imaged, then quantitated with ImageQuant. The relative total binding to the MBPs with the specific apoB antisera and the preimmune sera are as indicated. The insert contains the imaged lanes from the ligand blot.
Figure 17A:
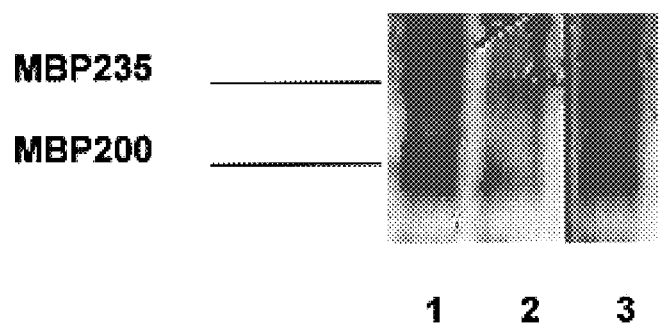
FIG. 17 shows that anti-apoB antibodies specifically block the binding of chylomicrons $S_f$1100–3200 (CM II) that contain apoB-48 as the only apoB species to MBP200 and MBP235. THP-1 aqueous phase extracts were electrophoresed and transferred to nitrocellulose. Prior to incubation with the nitrocellulose strips for 3 hours at 4° C., biotinylated CM II were preincubated at 4° C. for 30 minutes with buffer (lane 1), with anti-apoB (rabbit 1325) (lane 2), or with an equivalent level of nonimmune IgG (lane 3). Chylomicron binding was visualized after incubation with streptavidin-linked alkaline phosphatase, digitized (FIG. 17A) and quantified (FIG. 17B) by scanning densitometry.
Figure 17B:
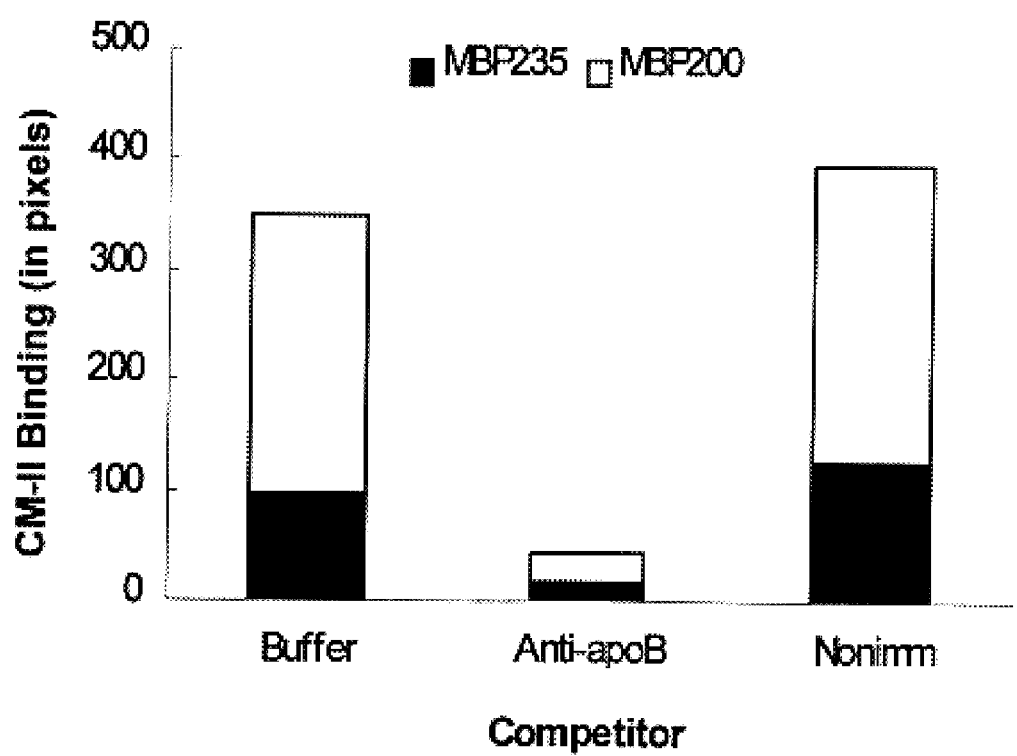

Neither ApoE nor lipoprotein lipase is required for binding of triglyceride-rich lipoprotein to monocytes and macrophages or to MBP200 and MBP235 on ligand blots (Gianturco, 1994). Anti-apoB antibodies inhibit binding of hypertriglyceridemic-very low density lipoprotein and tryp-very low density lipoprotein, devoid of apoE, to both THP-1 cells (FIG. 12) and MBP200 and MBP235 on ligand blots (FIGS. 5, 10 and 11). Control, nonimmune IgG tested at the same level had no effect on binding of triglyceride-rich lipoprotein to either cells (FIG. 12) or MBP200 or MBP235 on ligand blots (FIGS. 5, 10 and 11). The region of apoB that binds to the receptor is in the apoB-48 region (the N-terminal 48% of apoB-100), since chylomicrons containing apoB48, but not apoB-100, bind with high affinity (Gianturco, 1995) (FIG. 16), and this binding is inhibited specifically by antibodies against apoB (FIG. 17).

Competitive 4° C. cell binding and ligand blotting studies demonstrated that pretreatment and/or coincubation of cells (Table 1) and blots (FIG. 13) with heparin (up to 10 mg/ml) or lactoferrin (up to 500 μg/ml) had no effect on the apoE-independent binding of triglyceride-rich lipoprotein to cells or to MBP200 and MBP235, or on the triglyceride accumulation induced by triglyceride-rich lipoprotein in THP-1 cells. Since heparin pretreatment removes surface-bound lipoprotein lipase, and coincubation causes release of surface-bound lipoprotein lipase thereby enhancing triglyceride accumulation induced by triglyceride-rich lipoprotein when lipoprotein lipase is on the cell surface, these studies demonstrate that lipoprotein lipase is not necessary for the observed interactions. In contrast to studies with low density lipoprotein receptor family members, lipoprotein lipase at 1–2 mg/ml showed partial inhibition (~25% of specific binding) during co-incubations (FIG. 14; Table 1), and had no effect when blots were pretreated with lipoprotein lipase and then incubated with triglyceride-rich lipoprotein. Thus, lipoprotein lipase does not interact with the MBPs directly, but the partial inhibition during coincubation suggests that the binding domain for the MBPs in apoB is near the lipoprotein lipase binding site(s) of apoB, which has been shown to be in the N-terminal region. Thus, the receptor binding domains are in the N-terminal apoB region at or near the lipoprotein lipase binding site and not in a heparin binding domain, which is consistent with the observed binding of apoB48-containing chylomicrons to cells and to MBP200 and MBP235.

Thus, the binding determinant(s) appear to be in apoB. All native triglyceride-rich lipoproteins were isolated in the presence of antioxidants and show no evidence of oxidation, such as thiobarbituric acid reacting species (TBARs) or apoB fragmentation that oxidation produces. Thus, oxidation of triglyceride-rich lipoproteins is not required for their binding to this receptor. Although oxidized low density lipoprotein can compete for binding to the cellular site, it binds to numerous monocyte and macrophage proteins, and the competition appears to be non-specific.

EXAMPLE 18

Anti-apoB Antibodies Inhibit the Binding of HTG-VLDL $S_f$100–400 to MBP200 and MBP235

Previous experiments in human blood-borne and THP-1 monocytes and macrophages (Gianturco et al., 1994; Ramprasad et al., 1995) with the surrogate ligand, trypsinized-VLDL, which retained essentially all apoB immunoreactivity (in fragments of ≤100 kDa) but was devoid of immunochemically detectable apoE (Gianturco et al., 1983, 1986; Bradley et al., 1984) and apoCIII and failed to bind to the LDL receptor in cells (Gianturco et al., 1983) and in ligand blots (Gianturco et al., 1988), suggested that apoB may be the ligand for this monocyte-macrophage cell site and corresponding MBPs. Thus competitive ligand blotting experiments were done with several polyclonal anti-apoB specific antibodies to determine if these were capable of specifically blocking binding of HTG-VLDL to the putative TGRLP receptor proteins MBP200 and MBP235.

Figure 10A:
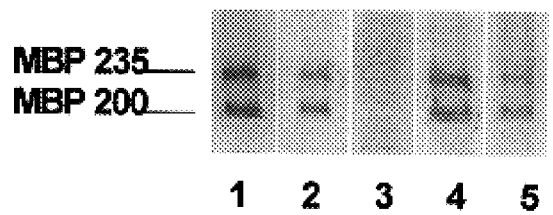
FIG. 10 shows that monospecific rabbit anti-human apoB IgGs specifically inhibit the binding of HTG-VLDL to the monocyte TGRLP receptor (MBP200 or MBP235). THP-1 monocyte aqueous phase extracts were electrophoresed and transferred to nitrocellulose (~100 μg/lane). Biotinylated HTG-VLDL $S_f$100–400 (0.5 μg/mL) was preincubated with buffer (lane 1) or with 2 levels of anti-apoB (rabbit 1325) 40 μg/mL lane 2; 400 μg/mL lane 3; or two levels of preimmune (rabbit 1325) IgG 90 μg/mL, lane 4 and 400 μg/mL, lane 5. Lipoproteins and IgGs were preincubated for 30 minutes and then incubated with the nitrocellulose strips for 3 hours at 4° C. After extensive washing, bound lipoprotein was detected with streptavidin linked to alkaline phosphatase followed by colorimetric substrates (the digitized image is shown in (FIG. 10A) and quantified by scanning densitometry (FIG. 10B) using two-dimension area integration and illustrated as VLDL binding in densitometric units (pixels).
Figure 10B:
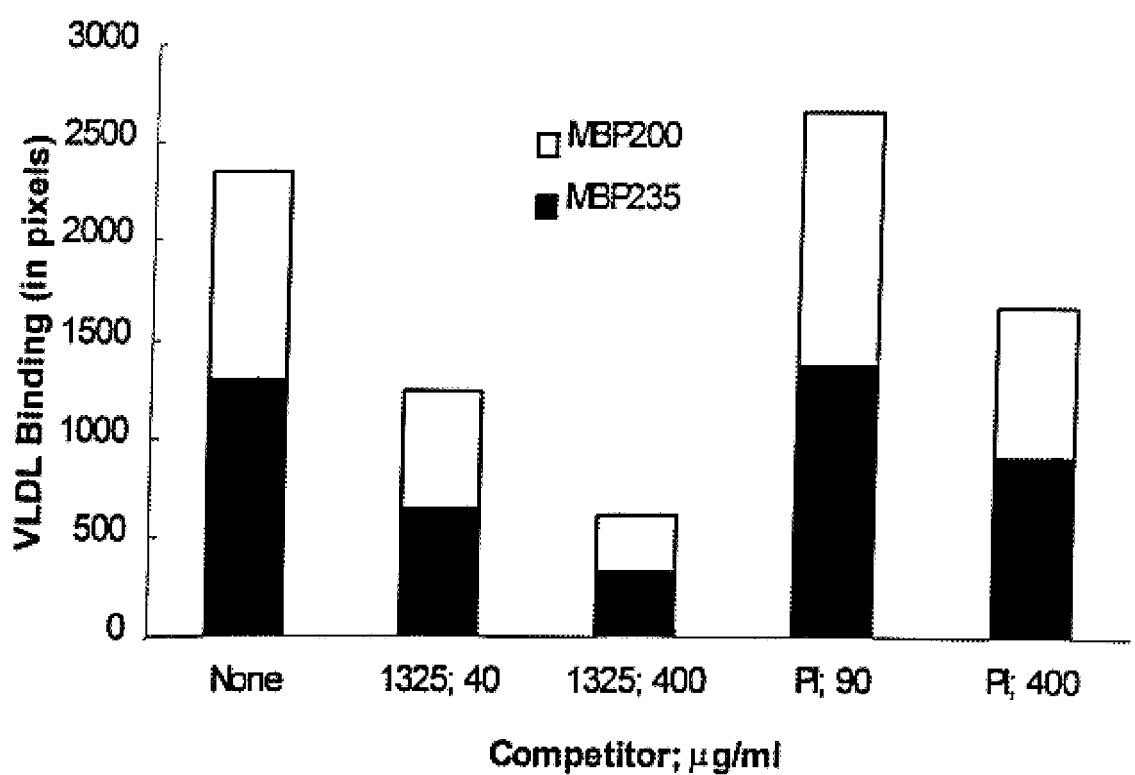

In the representative experiment shown in FIG. 10, THP-1 monocyte extracts were electrophoresed and transferred to nitrocellulose, blocked, and incubated with biotinylated VLDL in the absence (lane 1) and the presence of a monospecific rabbit (1325) anti-apoB IgG (40 μg/mL, lane 2; 400 μg/mL, lane 3), or the corresponding preimmune IgG (rabbit 1325) (90 μg/mL, lane 4; 400 μg/mL, lane 5). Binding of biotinylated HTG-VLDL $S_f$100–400 was visualized with streptavidin-linked alkaline phosphatase and the image digitized (FIG. 10A) and quantified by scanning densitometry (FIG. 10B). The lower level of anti-apoB IgG (40 μg/mL, lane 2) blocked ~50% of binding, and the higher level (400 μg/mL, lane 3) blocked all visibly detectable HTG-VLDL binding to MBP200 and MBP235 (~80% by densitometry). In contrast, the preimmune IgG at 90 μg/mL blocked none of the binding (lane 4), and at 400 μg/mL, blocked ~25% (lane 5). In a separate ligand blotting experiment, this apoB antibody did not inhibit the binding of the same biotinylated VLDL to the bovine LDL receptor. FIG. 10 is representative of 12 separate experiments with four different anti-apoB antibodies; in all cases, anti-apoB antibodies specifically inhibited binding of HTG-VLDL, chylomicrons, or tryp-VLDL to MBP200 and MBP235. Thus, apoB is involved in the binding of HTG-VLDL to the MBPs. These results are consistent with studies demonstrating specific, high affinity binding of tryp-VLDL and implicate apoB in the binding of TGRLP to MBP200 and MBP235. Alternatively, the anti-apoB antibodies could sterically hinder another component of the ligand for MBP200 or MBP235.

EXAMPLE 19

Antibodies Against other Apoproteins of HTG-VLDL Fail to Inhibit its Binding to MBP200 or MBP235

ApoB is only approximately 30% of the total protein mass in HTG-VLDL $S_f$100–400; apoE is 6–8%, and apoCs are ~63% (Gianturco et al., 1980, 1983). On a molar basis, HTG-VLDL $S_f$100–400 contains 1 mole of apoB, approximately 3–6 moles of apoE, and ≥150 moles apoCs (primarily apoCIII) per mole VLDL. To directly determine if any of these other apoproteins are the ligand sterically hindered by the anti-apoB antibodies in the experiments represented by FIG. 10, or if these apoproteins contribute to the binding of HTG-VLDL to MBP200 and MBP235, a series of competitive ligand blotting experiments with polyclonal antibodies against the other major apoproteins of HTG-VLDL were performed. All antibodies recognized their antigens in native VLDL and the anti-apoCIII antibody was used to isolate apoCIII-rich VLDLs.

Figure 11A:
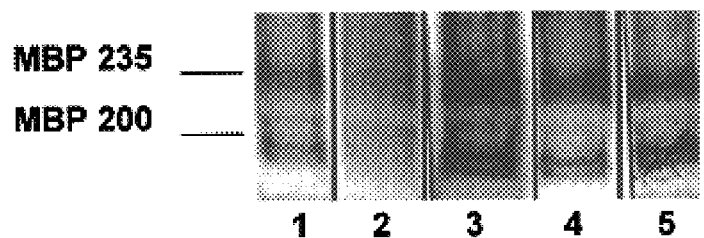
FIG. 11 shows that anti-apoB, but not anti-apoE, anti-apoCIII, or nonimmune IgG, inhibits the binding of HTG-VLDL $S_f$100–400 to MBP200 or MBP235. THP-1 monocyte aqueous phase extracts were electrophoresed and transferred to nitrocellulose, blocked, and incubated with biotinylated HTG-VLDL and the indicated antibodies at 4° C. Lane 1, buffer; lane 2, 3 mg/mL anti-apoB (1325); lane 3, 2.4 mg/mL nonimmune IgG; lane 4, 2.3 mg/mL anti-apoE; lane 5, 2 mg/mL anti-apoCIII. The IgGs were preincubated with biotinylated HTG-VLDL (2.5 μg/mL) for 30 minutes at 4° C. and then were incubated with the nitrocellulose strips for 3 hours at 4° C. Lipoprotein binding was visualized (FIG. 11A) and quantified (FIG. 11B) by densitometry as described in FIG. 10.
Figure 11B:
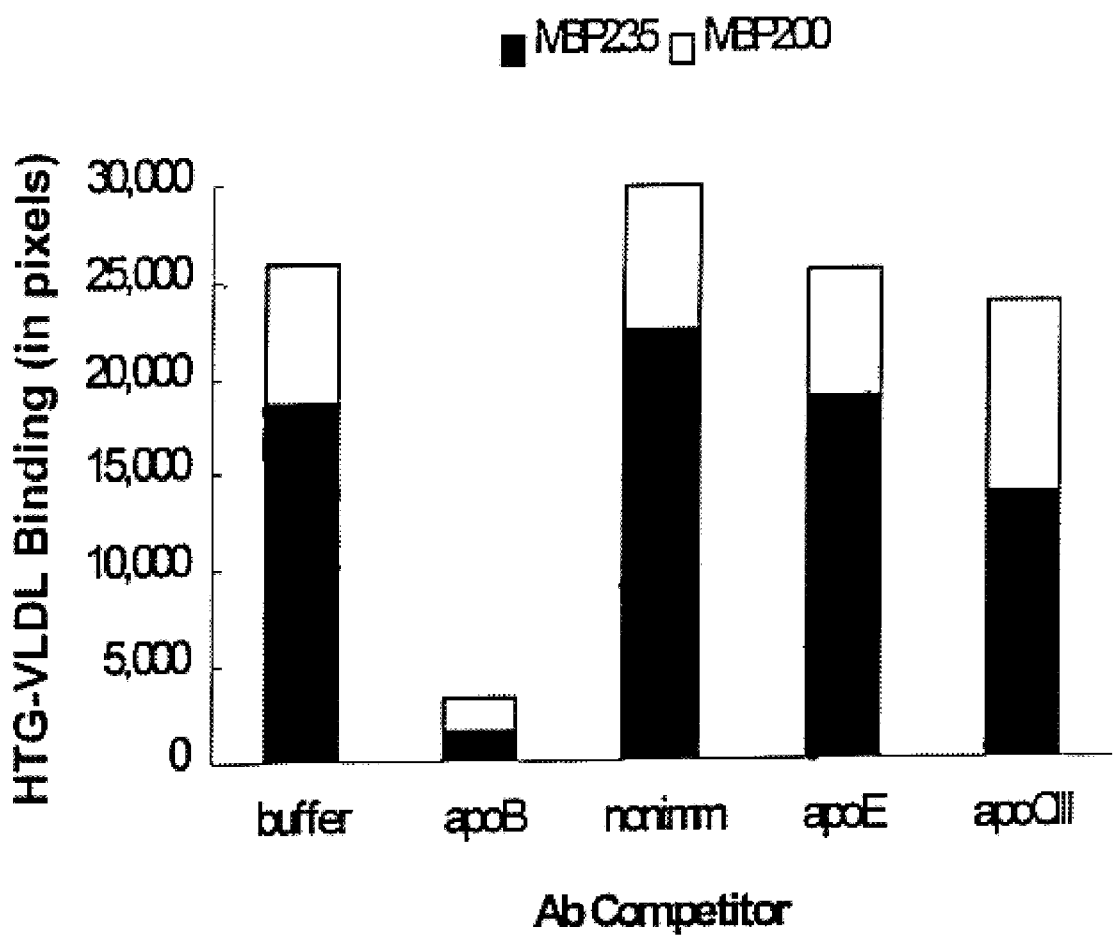

In FIG. 11, MBP200 and MBP235 activities (either or both) appear as a complex of two or more bands due to the existence of several permissible oxidation states and/or disulfide isomers, as previously published (Ramprasad et al., 1995). In the experiment shown in FIG. 11A, biotinylated HTG-VLDL $S_f$100–400 incubated with buffer (lane 1) or with nonimmune IgG (lane 3) binds to MBP200 and MBP235 to a similar extent. Neither anti-apoE (lane 4) nor anti-apoCIII (lane 5) diminishes the binding of HTG-VLDL to MBP200 or MBP235, but anti-apoB again effectively blocks >90% of the binding of HTG-VLDL (lane 2 and FIG. 11B). That anti-CIII antibody failed to block binding of HTG-VLDL to MBP200 or MBP235, even though the total apoCIII mass is approximately two times the mass of apoB in HTG-VLDL $S_f$100–400, argues against the alternative explanation offered above that the anti-apoB antibodies block by sterically hindering another apoprotein's interaction with the MBPs. In other ligand blotting experiments, the concentration of anti-apoE IgG used in these experiments blocked all binding of HTG-VLDL to the LDL receptor. Competitive ligand blotting studies with anti-apoCII IgGs demonstrated that these antibodies do not inhibit binding. Taken together, the competitive ligand blotting studies strongly suggest that apoB, but not apoE, apoCIII, or apoCII, mediates the binding of HTG-VLDL to MBP200 and MBP235.

Figure 12A:
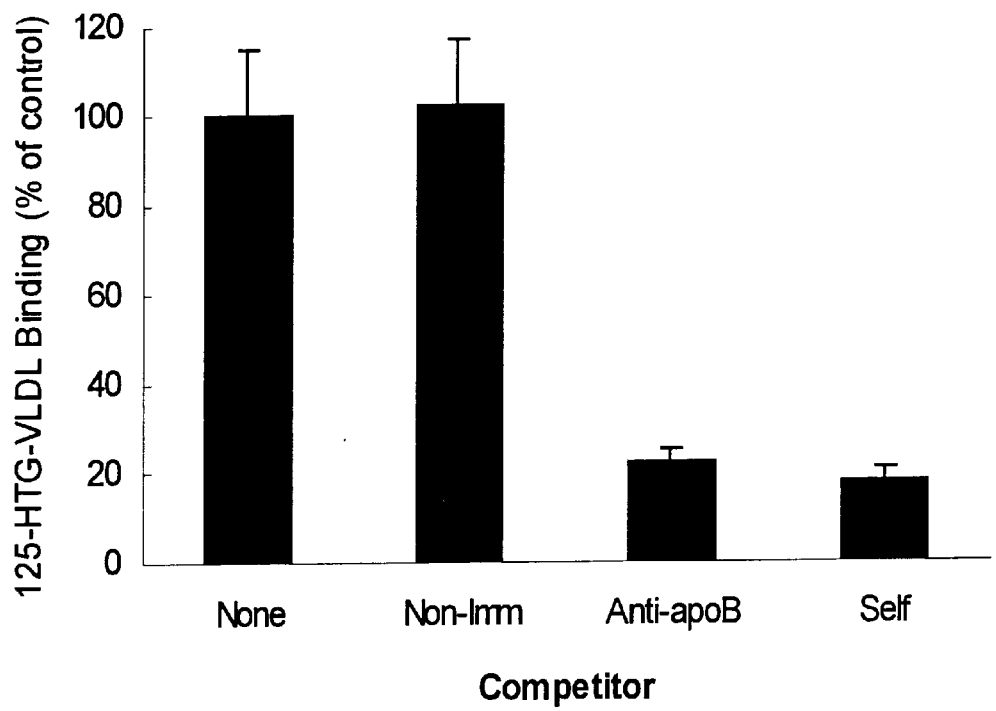
FIG. 12 shows that anti-apoB IgG, but not nonimmune IgGs, inhibit the binding of $^{125}$I-HTG-VLDL to THP-1 macrophages (top panel) but not to human fibroblasts with upregulated LDL receptors. (bottom panel) THP-1 monocyte-macrophages one day after adherence were grown as described. Duplicate dishes of cells and no cells for controls were incubated with $^{125}$I-HTG-VLDL $S_f$100–400, 5 μg/mL, alone (none) or in the presence of a 30-fold excess of unlabeled HTG-VLDL (self), in the presence of affinity-purified sheep anti-apoB IgG (anti-apoB), or the equivalent level of sheep nonimmune IgG (Non-Imm) at 4° C. for 16 hours and then incubated with precooled, washed cells for 1.5 hours at 4° C. After extensive washing, the cells were dissolved in 0.1 NaOH for determination of bound $^{125}$I-HTG-VLDL as described. Values represent the average of duplicate dishes corrected for background by subtracting the averages of the no-cell controls and are expressed in terms of percent of control, that is percent of the uninhibited activity (100%). Specific binding activity for $^{125}$I-TG-VLDL, 5 μg/mL was 24 ng/mg THP-1 cell protein which represented 100% uninhibited activity. (top panel) Human skin fibroblasts were grown to 75% confluency and preincubated with DME containing 5% lipoprotein-deficient serum for 36 h to induce the IDL receptor. The binding and competition protocol were identical to those for the THP-1 cells as described above. Specific binding activity for $^{125}$I-HTG-VLDL, 5 μg/mL was 237 ng/mg fibroblast cell protein which represented 100% uninhibited activity.
Figure 12B:
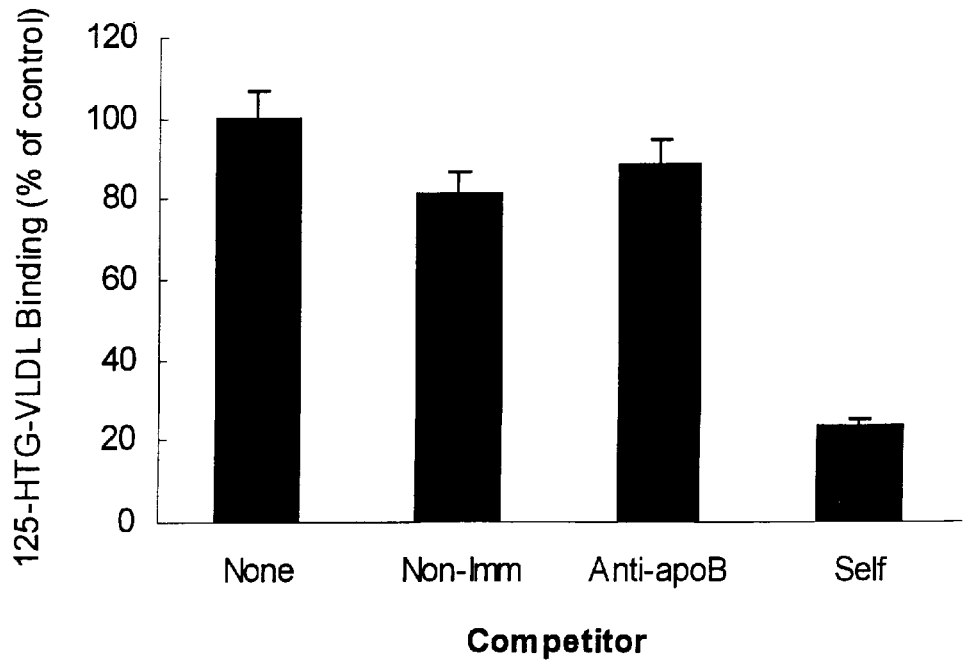

EXAMPLE 20
Anti-apoB Antibodies Inhibit the Binding of TGRLP to the TGRLP Receptor of THP-1 Monocytes but not to the LDL Receptor of Fibroblasts To confirm that apoB mediates the binding of TGRLP to the lipoprotein lipase- and apoE-independent TGRLP cellular receptor, competitive cell binding studies with THP-1 monocyte-macrophages were conducted under experimental conditions which minimize the expression of the LDL receptor, the LDL receptor-related protein/$\alpha_2$ macroglobulin receptor (LRP), lipoprotein lipase, and apoE (one day after adherence was induced by PMA) as described (Gianturco et al., 1994). As a control, competitive binding studies were also done simultaneously with cultured human skin fibroblasts with upregulated LDL receptors, since HTG-VLDL $S_f$100–400 binds to the LDL receptor via apoE and not via apoB (Gianturco et al., 1983; Bradley et al., 1984). Consistent with the ligand blotting studies (FIG. 10), the high affinity, specific binding of $^{125}$I-HTG-VLDL to THP-1s was inhibited by antibodies to apoB but not by the equivalent level of nonimmune IgGs (FIG. 12A). In contrast, and indicating the specificity of the blocking experiments in THP-1s, the same anti-apoB antibody did not inhibit the LDL receptor specific binding of $^{125}$I-HTG-VLDL to the fibroblasts (FIG. 12B), consistent with previous studies. This representative experiment shows that the inhibition of $^{125}$I-HTG-VLDL binding to THP-1s by anti-apoB antibodies was not significantly different from the inhibition by homologous, unlabeled HTG-VLDL. This indicates that apoB is the component of TGRLP responsible for their high affinity, specific binding to THP-1 cells when the LDL receptor, LRP, lipoprotein lipase, and apoE are suppressed.

Figure 13A:
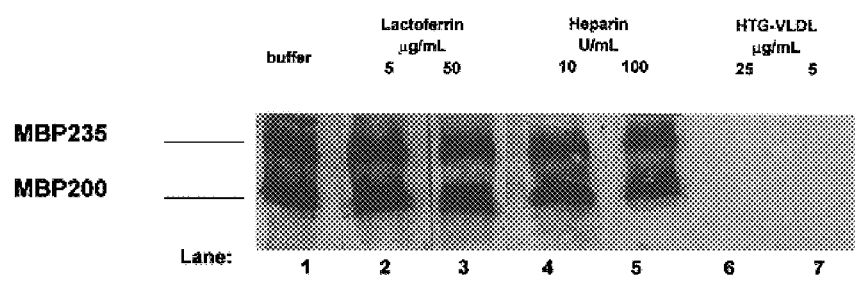
FIG. 13 shows the effects of lactoferrin and heparin on binding of HTG-VLDL to MBP200 and MBP235. THP-1 monocyte aqueous phase extracts were electrophoresed and transferred to nitrocellulose. The nitrocellulose strips were incubated for 4 hours at 4° C. with 0.5 μg biotinylated HTG-VLDL/mL in the absence (lane 1) or in the presence of lactoferrin at 50 μg protein/mL (lane 2) or 500 μg protein/mL (lane 3); heparin at 10 U/mL (lane 4) and 100 U/mL (lane 5); or unlabeled HTG-VLDL at 25 μg/mL (lane 6) or 5 μg/mL (lane 7). Biotinylated HTG-VLDL binding was detected with streptavidin linked alkaline phosphatase (digitized image, (FIG. 13 A) and quantified by densitometry (FIG. 13 B).
Figure 13B:
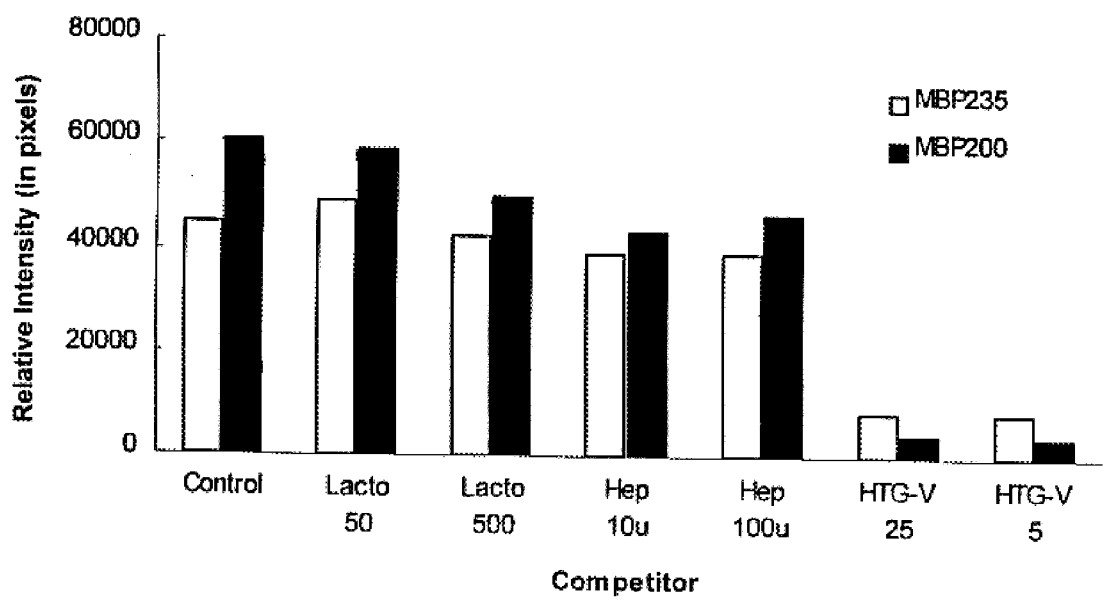
Figure 14A:
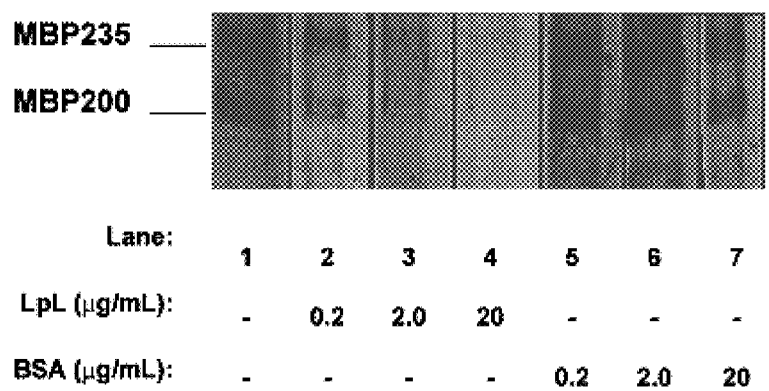
FIG. 14 shows that lipoprotein lipase inhibits the binding of HTG-VLDL to MBP200 and MBP235. THP-1 monocyte aqueous phase extracts were electrophoresed and transferred to nitrocellulose, blocked, and incubated at 4° C. with biotinylated HTG-VLDL $S_f$100–400 (3 μg of protein/mL) in the absence (lane 1) or in the presence of lipoprotein lipase (0.2 μg/mL, lane 2; 2.0 μg/mL, lane 3; 20 μg/mL, lane 4) or in the presence of bovine serum albumin (0.2 μg/mL, lane 5; 2.0 μg/mL, lane 6; 20 μg/mL, lane 7). Binding was detected by incubation with streptavidin-alkaline phosphatase and the image digitized (FIG. 14A) and quantified (FIG. 14B) by densitometry.

EXAMPLE 21
Effects of Lactoferrin, Heparin, and Lipoprotein Lipase on Binding of HTG-VLDL $S_f$100–400 to MBP200 and MBP235 and to THP-1 Monocyte-macrophages A series of competitive ligand blotting studies were carried out to further distinguish MBP200 and MBP235 from receptors of the LDL receptor family and to further delineate the binding domains in apoB for this distinct receptor. As shown in FIG. 13, neither lactoferrin nor heparin are effective inhibitors of the binding of HTG-VLDL to MBP200 and MPB235. In this representative experiment, nitrocellulose strips containing MBP200 or MBP235 were incubated with 0.5 $\mu$g of biotinylated HTG-VLDL/mL in the absence (lane 1) or in the presence of lactoferrin at 50 $\mu$g protein/mL (lane 2) or 500 $\mu$g protein/mL (lane 3); heparin at 10 U/mL (lane 4) and 100 U/mL (lane 5); or HTG-VLDL at 25 $\mu$g/mL (lane 6) or 5 $\mu$g/mL (lane 7). Binding of biotinylated VLDL was visualized with streptavidin-linked alkaline phosphatase (FIG. 13A) and quantified by scanning densitometry (FIG. 13B). Only unlabeled HTG-VLDL effectively competed with biotinylated HTG-VLDL for binding to MBP200 and MBP235. Lack of inhibition of TGRLP binding to MBP200 and MBP235 by heparin at levels that are known to displace lipoprotein lipase from cells indicates that binding is not mediated by lipoprotein lipase potentially bound to the VLDL. It also suggests that the apoB domain involved in binding to MBP200 and MBP235 is different from the apoB domain involved in the binding of LDL to the LDL receptor, since the apoB-LDL receptor interaction is disrupted by heparin (Goldstein et al., 1974). Further, it suggests that the domain in apoB that binds to MBP200 and MBP235 is not in a heparin-binding domain. Lack of inhibition of binding by lactoferrin indicates that MBP200 and MBP235 are distinct from the putative hepatic remnant receptors (van Berkel et al., 1995).

Figure 14B:
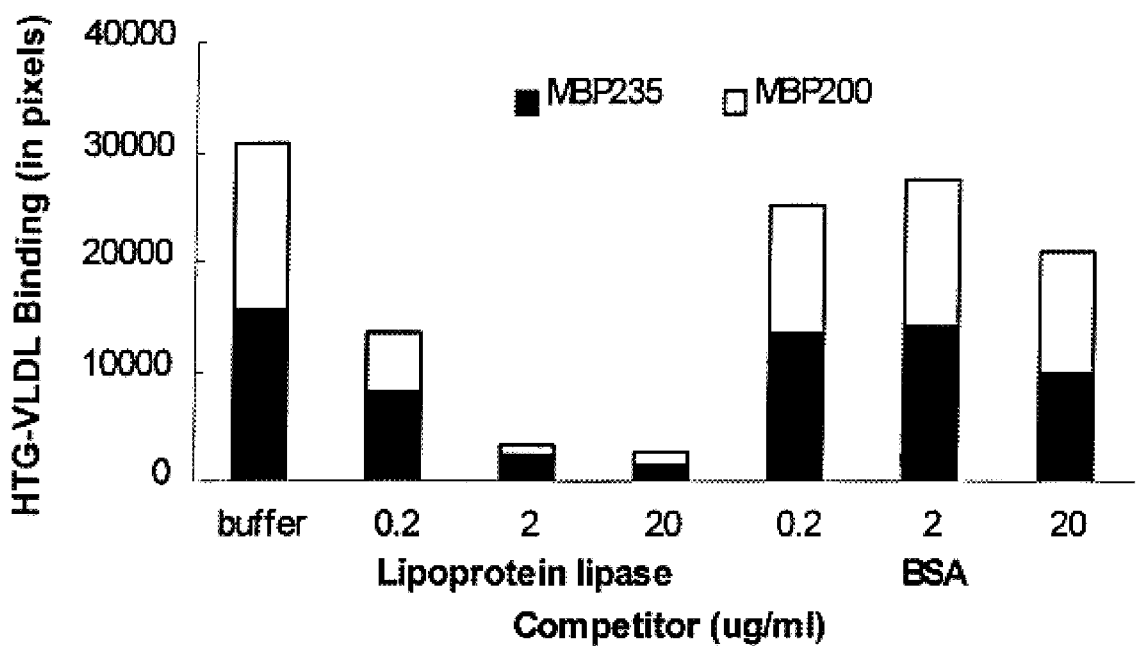

To further characterize the receptor binding domain in apoB of HTG-VLDL, and distinguish its binding to the monocyte TGRLP receptor from binding to the LDL receptor or related receptors, competitive ligand binding studies were carried out with levels of lipoprotein lipase reported to enhance binding of lipoproteins to LDL receptor family members or to heparan sulfate proteoglycans (HSPG) on cells. In the representative experiment shown in FIG. 14, THP-1 monocyte extracts were electrophoresed and transferred to nitrocellulose. Biotinylated HTG-VLDL (3 $\mu$g/mL) was preincubated for 30 min at 4° C. (to inhibit potential lipolysis by lipoprotein lipase) and then with the nitrocellulose strips for 3 h at 4° C. with buffer (lane 1) or with lipoprotein lipase (at 0.2, 2.0, 20 $\mu$g/mL; lanes 2–4) or with the same levels of bovine serum albumin as controls (lanes 5–7). Surprisingly, lipoprotein lipase, at levels which enhance binding to LRP, blocks the binding of HTG-VLDL to MBP200 and MBP235 in a concentration-dependent manner (FIG. 14B). In contrast, albumin has minimal effects on HTG-VLDL binding. Thus, lipoprotein lipase does not mediate the interaction of VLDL with this monocyte-macrophage receptor, rather, it inhibits binding. Inhibition of binding by LpL is likely due to its binding to the N-terminal domain of apoB (Choi et al., 1995), since preincubation of the receptors on nitrocellulose strips with lipoprotein lipase failed to inhibit the subsequent binding of TGRLP.

Competitive cell binding studies also demonstrated that lactoferrin fails to significantly inhibit the binding of tryp-VLDL or HTG-VLDL to monocyte-macrophages (<5%), and high levels of heparin (10 mg/mL) have only a small effect ($\leq$18%) (Table 1). Other studies with heparin at lower levels (1 mg/mL) show little to no inhibition of TGRLP binding. These binding studies also indicate that lipoprotein lipase, at levels shown by others to enhance binding of lipoproteins to cellular HSPG (Eisenberg et al., 1992; Rumsey et al., 1992), to LRP (Beisiegel et al., 1991; Chappel et al., 1993) and to the LDL receptor (Mulder et al., 1993) (1–2 μg/mL), do not enhance uptake of tryp-VLDL, rather they partially inhibit binding (to 26% at 1.6 μg lipoprotein lipase/mL). That the inhibition of binding of TGRLP to cells by lipoprotein lipase is less than the inhibition of TGRLP binding to MBP200 or MBP235 is likely due to the competing enhancement of lipoprotein binding to cellular HSPGs by lipoprotein lipase, which is not a confounder in ligand blots. Thus, the results of cell binding studies are similar to the results of ligand blotting studies, with inhibition of binding by anti-apoB and by lipoprotein lipase, but not by pre- or non-immune IgG, lactoferrin, or heparin.

TABLE 1

Competition of specific TGRLP binding to THP-1 monocytemacrophages

| | Percent Inhibition | | |
|---|---|---|---|
| Additions | Experiment 1 $^{125}$I-tryp-VLDL$_1$ | Experiment 2 $^{125}$I-HTG-VLDL$_1$ | Experiment 3 $^{125}$I-tryp-VLDL$_2$ |
| Buffer (control) | 0 | 0 | 0 |
| Lactoferrin | 4* | 5* | ND |
| LpL | 26† | ND | 17† |
| Heparin (10 mg/mL) | 14 | 18 | ND |
| Unlabeled VLDL (20x) | 100 | 100 | 100 |

THP-1 macrophages, 1 day after phorbol ester-induced adherence, were incubated with $^{125}$I-tryp-VLDL, 4 μg protein/mL (Exp. 1 and 3), or $^{125}$I-HTG-VLDL, 3 μg protein/mL, in RPMI 1640, HEPES (pH 7.4) and 2 mg BSA/mL with the additions for 1.5 hrs at 4° C. prior to washing and determination of bound lipoprotein. Values are averages from duplicate dishes of cells (which differed by ≦10% and were corrected for no-cell background) expressed as percent inhibition, with unlabeledVLDL inhibition as 100%. The specific binding (0% inhibition) ranged from ~140 to ~20 fmol/mg cell protein reflecting the particles differing affinities (tryp-VLDL$_1$ > HTG-VLDL$_1$ > tryp-VLDL$_2$).
*Lactoferrin at 100 μg/mL (experiment 1) and 500 μg/mL (experiment 2);
†LpL at 1.6 μg/mL (experiment 1) and 1.0 μg/mL (experiment 3).
ND = not determined.

EXAMPLE 22

Chylomicrons S$_f$>1100 Containing apoB-48 but not apoB-100 Bind to MBP200 and MBP235

The specific inhibition of HTG-VLDL and tryp-VLDL binding to cells and MBP200 and MBP235 on ligand blots by antibodies to apoB indicate that this apoprotein is necessary for the binding of HTG-VLDL to this receptor. The inhibition by LpL in cells and in ligand blots implicate the N-terminal domain of apoB. Previous studies showed that HTG-VLDL, but not normal VLDL S$_f$>60, bind with high affinity to cells, cause lipid accumulation, and bind to MBP200 and MBP235. HTG-VLDL subfractions from subjects with elevated plasma triglyceride (>150 mg/dL) contain more apoB-48 than VLDL subfractions from subjects with normal plasma triglycerides (<150 mg/dL) after purification by cumulative flotation because of delayed chylomicron remnant clearance (Bradley et al., 1984). Taken together, these results suggest that apoB-48 may be a preferred ligand, or at least contain a preferred conformational domain of apoB that enhances binding to this receptor. Thus, chylomicron subfractions isolated 4 h after a standardized fat load were studied (Weintraub et al., 1987). Chylomicrons, that is the TGRLP of S$_f$>400, were purified further by cumulative flotation into more homogeneous subfractions of S$_f$>3200 (CM I), S$_f$1100–3200 (CM II), and S$_f$400–1100 (CM III) (Lingren et al., 1972). The largest two chylomicron fractions (CM I and II) contained apoB-48 as the only detectable apoB species (FIG. 15, lanes 1–4) whereas the smallest fraction (CM III) (lanes 5, 6) contained both apoB-48 and apoB-100. Immunochemical blotting (FIG. 15), allowed estimation that <0.1%, or <1 in 1,000 particles, contain apoB-100 in the S$_f$>1100 subtractions. Lane 7 contains a typical fasting HTG-VLDL S$_f$100–400, with apoB-48 as well as apoB-100 and apoE. All chylomicron subfractions contained immunochemically detectable apoE (FIG. 15) and apoCs.

The three chylomicron subfractions were then tested for binding to MBP200 and MBP235 and to the partially purified bovine LDL receptor by ligand blotting analysis; a representative experiment is shown in FIG. 16. All of the chylomicron subfractions, added at equivalent concentrations, bound with high affinity to MBP200 and MBP235 (lanes 1, 3, 5) as well as to the LDL receptor (lanes 2, 4, 6).

Since apoB-48 is the only apoB species immunochemically detectable in the largest two chylomicron subfractions (CM I and CM II) (FIG. 15), this strongly implicates apoB-48, or an apoB-48 domain, as the primary apoprotein binding determinant for the distinct human apoE- and lipoprotein lipase-independent monocyte-macrophage receptor for TGRLP and its candidate receptor proteins, MBP200 and MBP235. Indeed, the binding of CM II to MBP200 and MBP235 was ~90% inhibited by anti-apoB IgGs, but not by nonimmune IgG (FIG. 17).

SUMMARY

The present invention discloses the ligand for a novel receptor and identification of the minimal requirements for receptor binding. Therefore, this invention describes means by which agents can be delivered to specific cells expressing the receptor or means by which the entry of ligands may be regulated for therapeutic use. Triglyceride-rich lipoprotein ligands of this receptor, in addition to causing lipid accumulation in monocytes and macrophages, cause increased monocyte adhesion to endothelial cells in vitro—a potentially atherogenic effect—by inducing the expression of adhesion molecules on both endothelial cells and on monocytes; cause phenotypic conversion of endothelial cells into multinucleated giant cells, like those found over human coronary atherosclerotic lesions; impair endothelial cell-mediated fibrinolysis; and induce enhanced expression of tissue factor mRNA and antigen in endothelial cells and monocytes, a prothrombotic effect.

Lipoproteins bind to this receptor via an apoB domain within the amino-terminal region. Competitive cell and ligand blotting studies demonstrate that anti-apoB, but not anti-apoE, anti-CIII or nonimmune IgG, inhibit binding of triglyceride-rich lipoproteins both to THP-1s and to the receptor proteins. Lactoferrin (100 μg/ml), heparin (10 mg/ml), and the human receptor associated protein do not inhibit triglyceride-rich lipoprotein binding. In contrast, lipoprotein lipase, which is known to bind to an N-terminal domain of apoB (Choi et al., 1995), partially inhibits binding of triglyceride-rich lipoproteins in both cell and ligand blotting studies via its interaction with apoB. Plasma chylomicrons S$_f$1100–3200 (4 h postprandial) that contain apoB-48 as the only apoB species bind specifically to the receptor proteins, and this can be inhibited by anti-apoB antibodies. Lipolysis of these S$_f$>1,100 apoB-48 diminishes binding to the receptor proteins (MBP200 and MBP235), while enhancing binding to the low density lipoprotein receptor. Smaller apoB-100 containing lipoprotein (intermediate density lipoprotein and low density lipoprotein) and normal very low density lipoprotein binding to the receptor on ligand blots can be detected. Competitive binding studies in monocyte-macrophages and in ligand blots, however, indicate the binding is of lower affinity than that of hypertriglyceridemic triglyceride-rich lipoproteins of $S_f$>60 and chylomicrons and their remnants, since twenty- to forty-fold excess of these lipoptoteins do not inhibit binding of the primary lipoprotein ligands (Gianturco, 1994). However, binding to MBP200 and MBP235 of low density lipoprotein that contains apoB-100 as the only detectable apo protein indicates that apoB is sufficient to mediate binding. These data strongly support that the monocyte-macrophage triglyceride-rich lipoprotein receptor-binding domain is within the N-terminal half of apoB corresponding to apoB-48 at or near the lipoprotein lipase binding domain and not in a heparin binding domain. These data also suggest that these receptors could account for the observed rapid peripheral macrophage uptake of plasma chylomicrons and represent a new apoB and monocyte-macrophage (and related cell type)-specific apoB receptor that is important in the nutrition of receptor-expressing cells, including circulating monocytes, accessible macrophages and placenta, especially in the postprandial state.

Knowledge of the receptor-binding determinants in the natural ligands (and knowledge of the domain(s) in the receptor that bind the ligands, i.e., the ligand-binding domains) provides an individual having ordinary skill in this art with the knowledge to design agents for the cell-specific delivery of drugs, vitamins, genes, enzymes, hormones, cytokines, growth factors, or inhibitors to cells expressing the receptor, including monocytes, macrophages, endothelial cells, placental cells, astrocytes, and the tissues which contain these cells, including bone marrow, blood vessels, spleen, lymph nodes, tonsils, appendix, thymus, liver, placenta, brain. For example, determination of the minimal peptide sequence sufficient to bind to the receptor and determination of the domain in the receptor which binds the ligand can be used to design synthetic peptides for incorporation in liposomes containing the desired chemical, enzyme, or gene. Alternatively, the agent could be directly linked to the peptide or to antibodies against the receptor. Such strategies could be useful for: (1) the treatment of monocytic leukemia; (2) the treatment of tuberculosis and other diseases, such as leprosy, caused by pathogenic mycobacteria, which require uptake by macrophages for pathogenesis (Schorey et al., 1997); (3) the treatment of AIDS, since HIV is harbored in macrophages after eradication from lymphocytes; (4) the inhibition or enhancement of angiogenesis (to inhibit angiogenesis in tumors or to promote angiogenesis in wound healing or after infarcts); (5) the inhibition or enhancement of fibrinolysis to promote clot formation or dissolution; (6) enhancement or inhibition of tissue factor production; and (7) the delivery of agents to the developing embryo. Conversely, synthetic agents which bind to the receptor and block or inhibit lipoprotein or other ligand binding to the receptor may also be useful in preventing excess uptake of lipoproteins/ligands via this route, thereby inhibiting foam cell formation and increased monocyte adhesion to endothelial cells, and decreasing inhibition of fibrinolysis by VLDL and inhibition of uptake of lipoprotein-soluble agents that are pathogenic for a specific cell or tissue, etc. Receptor mutations may be associated with specific dyslipidemias or abnormal postprandial triglyceride metabolism, which in turn are linked to increased risk of cardiovascular disease. Tests for receptor structure/function could be used to identify subjects at increased risk due to receptor defects. Abnormalities in the ligands of the receptor could also lead to defective or enhanced binding and uptake via this receptor and may also be predictive of increased disease risk. Receptor abnormalities may be involved in placental pathologies.

The following references were cited herein:

Assmann G, et al., *Am J Card*, 1992; 70:733–737.
Austin M., *Arteriosclerosis and Thrombosis*, 1991; 11:2–14.
Ausubel. *Current Protocols in Molecular Biol.* N.Y.: Wiley & Sons, 1987.
Bartlett G R., *J Biol Chem*, 1959; 234:466–468.
Basu S K, et al., *J Cell Biol*, 1977; 74:119–135.
Beisiegel U, et al., *Nature*, 1989; 341:162–164.
Beisiegel U, et al., *Proc Nat Acad Sci USA*, 1991; 88:8342–8346.
Bergeron N, et al., Simultaneous Quantification of apoB-100, apoB-48, and apoE separated by SDS-PAGE. In: Gianturco S H, et al., eds., *Methods in Enzymology*. Orlando, Fla.: Academic Press, 1995.
Bersot T P, et al., *J Clin Invest*, 1986; 77:622–630.
Bilheimer D W, et al., *Biochim Biophys Acta*, 1972; 250:212–221.
Bordier C. *J Biol Chem.*, 1985; 256:1604–1607.
Boyum A., *Scand J Clin Lab Invest*, 1968; 21:77–89.
Bradford M M. *Analytical Biochem.*, 1976; 72:248–254.
Bradley W A, et al., *J Biol Chem*, 1984; 259:14728–14735.
Bradley W A, et al., *J Lipid Research*, 1986; 27:40–48.
Bradley W A, et al., Triglyceride Rich Lipoproteins and Endothelial Cell Fibrinolysis. O Stein, et al. (eds.) In: *Atherosclerosis IX: Proceedings of the Ninth International Symposium on Atherosclerosis*. Tel Aviv, Israel, R & L Creative Commun. Ltd., 527–530, 1992.
Bradley W A, et al., Triglyceride Rich Lipoprotein Structure, Function, and Metabolism: Role in Coronary Heart Disease. R A Kreisberg, J P Segrest (eds.) In: *Plasma Lipoproteins and CoronaryArtery Disease* Cambridge, Mass., Blackwell Scientific Publications, Inc., 151–173, 1992.
Bradley W A, et al., *Atherosclerosis*, 108:S31–S39, 1994.
Bradley W A, et al., *J. Internal Med,.* 236:33–39, 1994.
Bradley W A, et al., AHA (Submitted), 1996
Brown M S, et al., *Ann Rev Biochem*, 1983; 52:223–261.
Brown S A, et al., *Biochem Biophys Res Comm*, 1986; 139:333–340.
Brunzell J D, et al., *Metabolism*, 1976; 25(3):313–320.
Bryne C D, et al., *Arteriosclerosis and Thrombosis, and Vascular Biology*, 1995; 15:65–70.
Burger, Monocytes and macrophages., *Nature*, 1970; 227:170–171.
Carlson L A, et al., *Lancet*, 1972; 1:865–868.
Catapano A L, et al., *J Biol Chem*, 1979; 254:1007–1009.
Chappel D A, et al., *J Biol Chem.*, 1993; 268:14168–14175.
Cheung M C, et al., *J Biol Chem*, 1984; 259:12201–12209.
Choi S Y, et al., *J Biol Chem.*, 1995; 270:8081–8086.
Cribbs L L, et al., *J Biol Chem*, 1989; 264:10672–10678.
D'Andrea A D, et al., *Cell*, 1989; 57(2):277–285.
Daniel O D, et al., *J Biol Chem*, 1983; 258:4606–4611.
Eisenberg S, et al., *Arteriosclerosis*, 1988; 8:480–487.
Eisenberg S, et al., *J Clin Invest*, 1992; 90:2013–2021.
Faggiotto A, et al., *Arteriosclerosis*, 1984; 4:341–356.
Fickett J W., *Nucleic Acids Res*, 1982; 10:5303–5318.
Fielding C J, et al., *J Biol Chem*, 1979; 254:8861–8868.
Fredrickson D S, et al., The familial hyperlipoproteinemias. In: Stanbury J G, Wyngaarden M F, Fredrickson D S, eds. *The metabolicbasis of inherited diseases*. N.Y.: McGraw-Hill, 1978:604–655.
Freedman A S, et al., *Science*, 1990; 249:1030–1033.
Gerrity R G., *Am J Path*, 1981; 103:181–190.
Gianturco S H, et al., *J Clin Invest*, 1978; 61:320–328.

Gianturco S H, et al., *Lipids*, 1980; 15:456–463.
Gianturco S H, et al., *J Lipid Res*, 1982a; 23:984–993.
Gianturco S H, et al., *J Clin Invest*, 1982b; 70:168–178.
Gianturco S H, et al., *J Biol Chem*, 1983; 258:4526–4533.
Gianturco S H, et al., *J Lipid Res*, 1986a; 27:412–420.
Gianturco S H, et al., The role of apolipoprotein processing in receptor recognition. In: Segrest J P, Albers J J, eds. *Methods in enzymology*. N.Y.: Academic Press, Inc., 1986b:319–344.
Gianturco S H, et al., *J Clin Invest*, 1988; 82(5):1633–1643.
Gianturco S H, et al., *Current Opinion in Lipidology*, 1991; 2:324–328.
Gianturco S H, et al., *J Lipid Res*, 1994; 35:1674–1687.
Gianturco S H, et al., A Cellular Basis for the Atherogenicity of Triglyceride-Rich Lipoproteins in *Atherosclerosis Reviews* Raven Press, Ltd. A. Gotto Jr. (ed) 22:9–14, 1991.
Gianturco S H, et al., *Arterioscl. and Thromb.*, 13(4):472–481, 1993.
Gianturco S H, et al., Atherogenicity of Triglyceride-Rich Lipoproteins: Cellular Aspects. Catapano, et al. (eds.) In *Drugs Affecting Lipid Metabolism*, The Netherlands, Kluwer Acad. Pub., 447–451., 1993.
Gianturco S H, et al., *Cur Opin in Lipidology*, 5(5):313–315, 1994.
Gianturco S H, et al., Interactions of Triglyceride-rich Lipoprotein Particles with the Arterial Wall, In: *Excerpta Medica: Proceedings of the Xth International Symposium on Atherosclerosis*, Elsevier Science, The Netherlands.
Gianturco S H, and Bradley W A, Section Co-Editors, Current Opinion Lipidology, *Atherosclerosis: Cell biology and lipoproteins*, 1995.
Gianturco S H, et al., AHA (Submitted), 1996
Ginsburg G S, et al., *J Biol Chem*, 1984; 259:6667–6673.
Gladson C L, et al., *Amer J Path*, 1995;
Goldstein J L, et al., *J Biol Chem*, 1974; 249:5153–5162.
Goldstein J L, et al., *Ann Rev Biochem*, 1977; 46:897–930.
Goldstein J L, et al., *Proc Natl Acad Sci USA*, 1979; 76:333–337.
Goldstein J L, et al., *J Biol Chem*, 1980; 255:1839–1848.
Goldstein J L, et al., Familial hypercholesterolemia. In: Stanbury J B, Wyngaarden J B, Fredrickson D S, eds. *The metabolic basis of inherited disease*. N.Y.: McGraw-Hill, 1983:672–712.
Gossen M, et al., *Proc Nat Acad Sci USA*, 1992; 89:5547–5551.
Grundy S M, et al., *Seminars in Thrombosis and Hemostasis*, 1988; 14(2):149–164.
Habeeb A F., *Analytical Biochemistry*, 1966; 14:328–336.
Hara H, et al., *Biochem Biophys Res Comm*, 1987; 146(2):802–808.
Helenius A, et al., *Biochemistry.*, 1971; 10:2542–2547.
Henikoff S., *Gene*, 1984; 28(3):351–359.
Henikoff S., *Methods in Enzymology*, 1987; 155:156–165.
Hui D Y, et al., *J Biol Chem*, 1984; 259:15060–15068.
Hussain M., et al., *J Biol Chem*, 1989; 264:9571–9582.
Hussain M., et al., *J Biol Chem*, 1989; 264:17931–17938.
Karlin J B, et al., Immunological heterogeneity of human apolipoprotein E as measured by radioimmunoassay. In: Lippel K, ed. *Proceedings of the workshop on apolipoprotein quantification*. Washington, D.C.: NIH, 1983:212–221.
Kates M. *Techniques of lipidology*. N.Y.: Holland/American Elsevier, 1972.
Khoo J C, et al., *J Biol Chem*, 1981; 256:7105–7108.
Kleinman Y, et al., *J Lipid Res*, 1988; 29:729–743.
Kodama T, et al., *Proc Nat Acad Sci USA*, 1988; 85:9238–9242.
Kodama T, et al., *Nature*, 1990; 343:531–535.
Kowal R C, et al., *J Biol Chem*, 1990; 265:10771–10779.
Kowal R C, et al., *Proc Natl Acad Sci USA*, 1989; 86:5810–5814.
Krauss R M., *Cur Opin in Lipidology*, 1994; 5:339–349.
Krul E S, et al., *J Clin Invest*, 1985; 75:361–369.
Laemmli U K. *Nature.*, 1970; 227:680–685.
Lang I, et al., *Circulation*, 1994; 89:2715–2721.
Lang I, et al., *Circulation*, 1994; 90(2):706–712.
Lindgren F T, et al., The isolation and quantitative analysis of lipoproteins in blood lipids and lipoproteins. In: Nelson G J, ed. *Blood lipids and lipoproteins*. New York: Wiley interscience, 1972:181–274.
Lindqvist P, et al., *J Biol Chem*, 1983; 258:9086–9092.
Lowry O H, et al., *J Biol Chem.*, 1951; 193:265–275.
Maurice receptor, et al., *J Lipid Res*, 1989; 30:587–596.
Maxam A M, et al., *Methods in Enzymology*, 1980; 65(1):499–560.
Means G E, et al., *Chemical modification of proteins*. Holden Day, Inc., 1971.
Miller K W, et al., *Biochemistry*, 1983; 22:443–451.
Milne R W, et al., *J Clin Invest*, 1984; 73:816–823.
Milne receptor, et al., *J Biol Chem*, 1989; 264:19754–19760.
Moestrup S K, et al., *Exp Cell Res*, 1990; 190:195–203.
Morrisett J D, et al., *American Oil Chemists Society Monograph#4*. Champaign, Ill.: A.O.C.S. Pub., 1977:139–161.
Mulder M, et al., *Biochem Biophys Res Com*, 1992; 185:582–587.
Mulder M, et al., *J Biol Chem.*, 1993; 268:9369–9375.
Nagata Y, et al., *J Lipid Res*, 1987; 28:684–692.
Nakashima et al., *Arteriosclerosis and Thrombosis*, 1994; 14:133–140.
Nordestgaard B G, et al., *Cur Opin Lipidology*, 1994; 5:252–257.
Novitsky T. Choosing a method. In: Novitsky T, ed. *LAL update* 1. 1983:1–3.
Nykjaer A, et al., *J Biol Chem*, 1993; 268:15048–15055.
O'Hara O, et al., *Proc Natl Acad Sci USA*, 1989; 86(15):5673–5677.
O'Shannessy D J, et al., *Immunology Letters.*, 1984; 8:273–277.
Ostlund-Lindqvist A M, et al., *Arteriosclerosis*, 1983; 3:433–440.
Parker F, et al., *J Clin Invest*, 1970; 49:2172–2187.
Phillips N R, et al., *Circulation*, 1993; 88:2762–2770.
Plump A S, et al., *Cell*, 1992; 71:343–353.
Ramprasad M P et al., *Biochem.*, 1995; 34:9126–9135.
Ramprasad et al., *Biochem. Biophys. Res. Comm.*, 1995; 210:491–497.
Rapp J H, et al., *Arteriosclerosis and Thrombosis*, 1994; 14:1767–1774.
Reddick R L, et al., *Arteriosclerosis and Thrombosis*, 1994; 14:141–147.
Ross C A, et al., *J Lipid Res*, 1977; 18:169–181.
Rumsey S C, et al., *J Clin Invest.*, 1992; 90:1504–1512.
Sacks F M, et al., *Arteriosclerosis*, 1987; 7:35–46.
Sambrook J, et al., *Molecular cloning: A laboratory manual*. Cold Spring Harbor, N.Y.: Cold Spring Harbor Laboratory Press, 1989.
Sanger F, et al., *Proc Natl Acad Sci USA*, 1977; 74:5463–5467.
Schaefer E J, et al., *Sem Thromb Hem*, 1988; 14:143–148.
Schneider W J, et al., *J Biol Chem*, 1982; 257:2664–2673.
Schonfeld G, et al., *J Clin Invest*, 1979; 64:1288–1297.
Schorey J S et al., *Science*, 1997, 277:1091–3.
Sehayek E, et al., *Cur Opin Lipidology*, 1994; 5:350–353.
Shen B W, et al., *Proc Nati Acad Sci USA*, 1977; 74:837–841.

Sparrow C P, et al., *J Lipid Res*, 1988; 29:745–753.
Strickland D K, et al., *J Biol Chem*, 1990; 265:17401–17404.
Takahashi S, et al., *Proc Natl Acad Sci USA*, 1992; 89:9252–9256.
Takahashi S, et al., *Circulation*, 1994; 90:I-2.
Terce F, et al., *Arteriosclerosis*, 1985; 5:201–211.
van Berkel T J C, et al., *Cur Opin Lipidology*, 1994; 5:331–338.
van Berkel T J C, et al., *Biochem J.*, 1995; 310:359–360.
Via D P, et al., *Proc Natl Acad Sci USA*, 1992; 89:6780–6784.
Via D P, et al., *J Lipid Res*, 1989; 30:1515–1524.
Via D P, et al., *J Biol Chem*, 1985; 260:7379–7386.
Wang-Iverson P, et al., *Bioc. Biophys Res Comm*, 1985; 126:578–586.
Weintraub M S, et al., *J Clin Invest* 1987; 79:1110–1119.
Williams K J, et al., *J Biol Chem*, 1992; 267:13284–13292.
Yang C, et al., *Nature*, 1986; 323:738–742.
Yokoyama C, et al., *Cell*, 1993;75:187–197.
Zhang S H, et al., *Science*, 1992; 258:468–471.
Gianturco S H, et al., *Ann. Nutr. Metab.* 36:349–350, 1992.
Ramprasad M P, et al., *Circulation*, 86(4):2434, 1992.
Varma V K, et al., *Circulation*, 86(4):2192, 1992.
Parks J M, et al., *Circulation*, 88(4–2):1227A, 1993.
Tarpey Monocytes and macrophages, Am. Lung Association, 1993.
Gianturco S H, et al., *Atherosclerosis*X,109:260, 1994.
Ramprasad M P, et al., *Circulation*, 90(4):I-2, 1994.
Bradley W A et al., *Circulation*, 92(8):I-691, 1995.
Gianturco S H et al., *Circulation*, 92(8):I-690, 1995.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA molecule encoding a monocyte-macrophage cell-surface receptor protein, said DNA molecule selected from the group consisting of:

a) a DNA molecule comprising SEQ ID NO: 1 encoding said monocyte-macrophage cell-surface receptor protein or a fragment of said potein, wherein said fragment specifically binds apolioprotein B; and b) a DNA molecule differing from the DNA molecule of (a) in codon sequence due to the degeneracy of the genetic code, and which encodes said monocyte-macrophage cell-surface receptor protein as set forth in SEQ ID NO: 2 or a fragment of said protein, wherein said fragment specifically binds apolipoprotein B.

2. A vector containing the DNA molecule of claim 1 and regulatory elements necessary for expression of said DNA in a cell, said vector adapted for expression in a recombinant cell.

3. A host cell containing the vector of claim 2.

4. An isolated DNA molecule encoding a portion of the monocyte-macrophage cell-surface receptor protein, said DNA molecule selected from the group consisting of SEQ ID No. 3, SEQ ID No. 7, SEQ ID No. 8 and SEQ ID No. 9.

5. A vector containing the isolated DNA molecule of claim 4 and regulatory elements necessary for expression of said DNA in a cell, said vector adapted for expression in a recombinant cell.

6. A host cell containing the vector of claim 5.

* * * * *

SEQUENCE LISTING

<160> NUMBER OF SEQ ID NOS: 10

<210> SEQ ID NO 1
<211> LENGTH: 3773
<212> TYPE: DNA
<213> ORGANISM: Homo sapien

<400> SEQUENCE: 1

```
gcggccgcgt ctaccgcggc cgcgtctacg acagacagga tggacttcct ccggctatac      60
ctccctgggc tgcaccaggc cttgaggggg gcactggatt ccctcggcac ctttgtctcc     120
tacctcctgg gagatgcagt ccccactgta gagcgggagg cgcaggcggc tgaggaactg     180
ggggtggtgg cggtgggaaa gacagggaag attgtagagg aggaagccca ggaggacctg     240
gagggcctta gaggcagcca aaacgagggg gctggaaggc tgagagggcc tggagatgac     300
agaagacatg aagtggggag ctcagctgta gaacagacct ggggctgggg agatggcagc     360
tcccatgggt cccaagcaga gaggcaggac agtgggggctg gggagacagc caaggctgcc     420
aggtgccagg agccaagcgc ccacttggag gccagaaaga aatccaaggc agggtctggg     480
gcttgccaag acaggagcgg ccaagcccag gagaggcagg agtcccatga gcaggaagtg     540
aacagagagg agaggctgag aagctgggaa caggaggagg aggaggaaga ggtcagggca     600
agggagccag ggatggccag aggggcggag tcagagtgga cctggcatgg ggagacggag     660
gggaaggctg gtgctgttgg gccaaaggcg gcagggggaca accgggagat ggagcagggg     720
gtcagggagg cagatgcagg ggaaactgag gagcctgggg ccgaaggggc tgggaaagga     780
gaagaggtgg tagtggtgga gaaggcctgt gaaagcacta gggcatgggg gacgtggggc     840
ccaggggcag agcctgagga ctggggaatc ttaggcagag aggaggccag gacaacccca     900
ggtagggaag aggccagggc aatttttagat ggggaggaag ccaggacaat ctcaggcggg     960
gaggaggctg agacagcctc aggcggggag gaggctgaaa cagcctcagg cggggaggag   1020
gccgggacag cctcgggagg ggaggaggcc gggatatcct caggcgggga ggctgggaca   1080
```

-continued

| | | | | |
|---|---|---|---|---|
| gcctcaggag | gggaggaggc | cgggacagcc | tctggagggg | acgaggcctg gacaacctca | 1140 |
| ggcaaagagg | aggctgacct | gctgggagtc | agacagactc | aatatggagc agttccagga | 1200 |
| gaaaggctcc | tagaggctac | tggaaaagtc | tgggtcctag | aggaggaggg ggatgaggag | 1260 |
| agagaggctg | aggtgagccc | tttccccaaa | caggcccagg | tcctgggcac tgaaagaaca | 1320 |
| gaagaggctg | ctgagagcca | gaccgcaggg | agggaagctg | tggaggcca ggaggcaggg | 1380 |
| gagagctttg | agggccaggt | agacctgcgt | ggtaaggagg | ctgagatgag gcaggacttg | 1440 |
| gggatcaggg | ccgaccgggc | caagatgaaa | gagctggtac | aggcagagga ggcccaggag | 1500 |
| gagagaggga | gcagcaggga | tccagtggct | gagctgccct | cagatggaga ggctgaaggc | 1560 |
| actgccgact | tggaggcaac | tccagaggcc | aggcctgagg | aggagctcac aggggaggag | 1620 |
| agtgaggcgg | cccagactag | ctgtggccta | ctgggcgtgg | aatgggtgg cctcacacac | 1680 |
| agcgtcacca | aaggccaggg | acctgagctg | atggggggtg | cccagacccc aactaagcaa | 1740 |
| cccgaggaaa | gggaggcagg | ggaggtggag | ctcatgggag | ttctggccct gagcaaagag | 1800 |
| gagcaggaga | ggagcctgga | ggcaggtccc | aggcacgcgg | ggtctgtaaa gcctgaggcc | 1860 |
| tccgaggcct | tcccaggagc | ctgggaaaac | cgcacgagaa | aggacatgga gagaggaaat | 1920 |
| actcaggagg | atgcggccga | tggcgagcag | cgggaggagg | aggagactgc gggaggccag | 1980 |
| accctggcgg | ctgaggctga | aggagaccga | gagtctgaac | tatcagaagt cccagaggca | 2040 |
| ggcgggagg | ggctgacaac | ccaggacgcg | ggatgtggaa | ctgaggaggg agaggcatct | 2100 |
| gtctcagaga | accaggagct | ggacggaagc | acaggggcag | acgcagggcc ttgcccgtca | 2160 |
| ctgggagagg | cctatgccag | agaaactgag | gatgaggagg | cggaggctga cagaacatcc | 2220 |
| agaagaggct | ggaggctgca | agcggtggct | gtgggcctcc | cggaccgtga ggatgcacag | 2280 |
| actggctctg | tggctgctgg | gattatgggg | ggtgatgtgg | tcccacacat cagcgctgct | 2340 |
| ggcgctggtg | aagctttgga | aggggcgctt | gggcaaggct | gggactcgaa agaaaaggaa | 2400 |
| gaggcagcag | caggagagca | tgcaggtggg | caagaatttg | gtctggaggg ctcagcagag | 2460 |
| gaagaggtga | ctgcagagg | cagccaagta | gaggcttttg | agtccaggga gggaggacct | 2520 |
| tggggagggc | gggtagaggc | cgaggaatct | gcaggcgcag | aggacagctg tgggctggat | 2580 |
| cccgcgggct | cccagacagc | gagggcagag | gggatgggag | ccatggtgga ggctgggggg | 2640 |
| cttctagaaa | agtggacgct | gttggaagaa | gaggctgttg | gatggcagga gagagaacag | 2700 |
| agggaagaca | gtgaggggcg | gtgtggggac | taccaccctg | agggagaggc accaaggctc | 2760 |
| cttgatgcag | agggtctcat | ggtgaccggg | ggccggaggg | cagaggccaa ggagactgag | 2820 |
| ccagaaagcc | tggaacatgt | caggggccag | gaggagcagc | caacacacca ggcccctgca | 2880 |
| gaagctgcgc | cggagtcagt | cggggaagcc | gagacggctg | aggccatggg cagtgccaga | 2940 |
| ggaggtgctg | ccaacagctg | gagcgaggcc | ccgctccccg | ggtccctcct agacgtctct | 3000 |
| gtcccaagga | gtcgcgtgca | cctctcgaga | agctcctcac | agcgtcgctc ccggccctct | 3060 |
| tttcgtcgga | ctccggcctg | ggagcagcag | gaggagcccc | cagcccccaa ccctcctgag | 3120 |
| gaggagctgt | cagctcctga | gcagagaccc | ctccagctgg | aggaacccct ggagccaagc | 3180 |
| cctctgaggc | atgatgggac | cccggtgcca | gccaggagaa | ggcccctggg acacgggttt | 3240 |
| ggcctcgcgc | acctggcat | gatgcaggag | ctgcaagccc | gtctgggccg gcctaagccc | 3300 |
| cagtgactga | gacccggtgc | tctgggagcc | aggccctgag | tgggtgccag aaggcttgct | 3360 |
| ccaatgccac | tgagccctgc | tccctctgcc | actgtggaca | catcctctcc accctctggg | 3420 |
| cctcagtgtc | ttgatgtatc | attcatggag | caggcaaaac | cagacgtctg ggaataccgt | 3480 |

-continued

```
gaacttaagg agtctgattc tccgacacag gctggtggac cacctacccc actgagacca    3540
cctctcaggg tgcctgccct ggttcctccc cagcctgagt cagctgtctg gactgcaagg    3600
aggctgggca cggggctca  cgcctgtcac cccagagctt tgggaggcca aggtgggagg    3660
atcgcttgag accaggagtt cgagaccagc ctgggcagca tagcaagatc cccatctttt    3720
aaaaacaaaa taaaacaata aagactgcaa ggaaaaaaaa aaaaaaaaaa aaa           3773
```

<210> SEQ ID NO 2
<211> LENGTH: 1088
<212> TYPE: PRT
<213> ORGANISM: Homo sapien

<400> SEQUENCE: 2

```
Met Asp Phe Leu Arg Leu Tyr Leu Pro Gly Leu His Gln Ala Leu
 1               5                  10                  15

Arg Gly Ala Leu Asp Ser Leu Gly Thr Phe Val Ser Tyr Leu Leu
                20                  25                  30

Gly Asp Ala Val Pro Thr Val Glu Arg Glu Ala Gln Ala Ala Glu
            35                  40                  45

Glu Leu Gly Val Val Ala Val Gly Lys Thr Gly Lys Ile Val Glu
        50                  55                  60

Glu Glu Ala Gln Glu Asp Leu Glu Gly Leu Arg Gly Ser Gln Asn
    65                  70                  75

Glu Gly Ala Gly Arg Leu Arg Gly Pro Gly Asp Asp Arg Arg His
80                  85                  90

Glu Val Gly Ser Ser Ala Val Glu Gln Thr Trp Gly Trp Gly Asp
            95                  100                 105

Gly Ser Ser His Gly Ser Gln Ala Glu Arg Gln Asp Ser Gly Ala
        110                 115                 120

Gly Glu Thr Ala Lys Ala Ala Arg Cys Gln Glu Pro Ser Ala His
    125                 130                 135

Leu Glu Ala Arg Lys Lys Ser Lys Ala Gly Ser Gly Ala Cys Gln
140                 145                 150

Asp Arg Ser Gly Gln Ala Gln Glu Arg Gln Glu Ser His Glu Gln
        155                 160                 165

Glu Val Asn Arg Glu Glu Arg Leu Arg Ser Trp Glu Gln Glu Glu
    170                 175                 180

Glu Glu Glu Glu Val Arg Ala Arg Glu Pro Gly Met Ala Arg Gly
185                 190                 195

Ala Glu Ser Glu Trp Thr Trp His Gly Glu Thr Glu Gly Lys Ala
        200                 205                 210

Gly Ala Val Gly Pro Lys Ala Ala Gly Asp Asn Arg Glu Met Glu
    215                 220                 225

Gln Gly Val Arg Glu Ala Asp Ala Gly Glu Thr Glu Pro Gly
230                 235                 240

Ala Glu Gly Ala Gly Lys Gly Glu Glu Val Val Val Glu Lys
        245                 250                 255

Ala Cys Glu Ser Thr Arg Ala Trp Gly Thr Trp Gly Pro Gly Ala
    260                 265                 270

Glu Pro Glu Asp Trp Gly Ile Leu Gly Arg Glu Glu Ala Arg Thr
275                 280                 285

Thr Pro Gly Arg Glu Glu Ala Arg Ala Ile Leu Asp Gly Glu Glu
        290                 295                 300
```

-continued

```
Ala Arg Thr Ile Ser Gly Gly Glu Glu Thr Ala Ser Gly
            305                 310                 315
Gly Glu Glu Ala Glu Thr Ala Ser Gly Gly Glu Glu Ala Gly Thr
            320                 325                 330
Ala Ser Gly Gly Glu Glu Ala Gly Ile Ser Ser Gly Gly Glu Ala
            335                 340                 345
Gly Thr Ala Ser Gly Gly Glu Glu Ala Gly Thr Ala Ser Gly Gly
            350                 355                 360
Asp Glu Ala Trp Thr Thr Ser Gly Lys Glu Glu Ala Asp Leu Leu
            365                 370                 375
Gly Val Arg Gln Thr Gln Tyr Gly Ala Val Pro Gly Glu Arg Leu
            380                 385                 390
Leu Glu Ala Thr Gly Lys Val Trp Val Leu Glu Glu Glu Gly Asp
            395                 400                 405
Glu Glu Arg Glu Ala Glu Val Ser Pro Phe Pro Lys Gln Ala Gln
            410                 415                 420
Val Leu Gly Thr Glu Arg Thr Glu Glu Ala Ala Glu Ser Gln Thr
            425                 430                 435
Ala Gly Arg Glu Ala Val Gly Gly Gln Glu Ala Gly Glu Ser Phe
            440                 445                 450
Glu Gly Gln Val Asp Leu Arg Gly Lys Glu Ala Glu Met Arg Gln
            455                 460                 465
Asp Leu Gly Ile Arg Ala Asp Arg Ala Lys Met Glu Glu Leu Val
            470                 475                 480
Gln Ala Glu Glu Ala Gln Glu Glu Arg Gly Ser Ser Arg Asp Pro
            485                 490                 495
Val Ala Glu Leu Pro Ser Asp Gly Glu Ala Glu Gly Thr Ala Asp
            500                 505                 510
Leu Glu Ala Thr Pro Glu Ala Arg Pro Glu Glu Leu Thr Gly
            515                 520                 525
Glu Glu Ser Glu Ala Ala Gln Thr Ser Cys Gly Leu Leu Gly Val
            530                 535                 540
Glu Trp Gly Gly Leu Thr His Ser Val Thr Lys Gly Gln Gly Pro
            545                 550                 555
Glu Leu Met Gly Gly Ala Gln Thr Pro Thr Lys Gln Pro Glu Glu
            560                 565                 570
Arg Glu Ala Gly Glu Val Glu Leu Met Gly Val Leu Ala Leu Ser
            575                 580                 585
Lys Glu Glu Gln Glu Arg Ser Leu Glu Ala Gly Pro Arg His Ala
            590                 595                 600
Gly Ser Val Lys Pro Glu Ala Ser Glu Ala Phe Pro Gly Ala Trp
            605                 610                 615
Glu Asn Arg Thr Arg Lys Asp Met Glu Arg Gly Asn Thr Gln Glu
            620                 625                 630
Asp Ala Ala Asp Gly Glu Gln Arg Glu Glu Glu Thr Ala Gly
            635                 640                 645
Gly Gln Thr Leu Ala Ala Glu Ala Glu Gly Asp Arg Glu Ser Glu
            650                 655                 660
Leu Ser Glu Val Pro Glu Ala Gly Gly Glu Gly Leu Thr Thr Gln
            665                 670                 675
Asp Ala Gly Cys Gly Thr Glu Glu Gly Glu Ala Ser Val Ser Glu
            680                 685                 690
Asn Gln Glu Leu Asp Gly Ser Thr Gly Ala Asp Ala Gly Pro Cys
```

```
                    695                 700                 705
Pro Ser Leu Gly Glu Ala Tyr Ala Arg Glu Thr Glu Asp Glu Glu
                710                 715                 720
Ala Glu Ala Asp Arg Thr Ser Arg Arg Gly Trp Arg Leu Gln Ala
                725                 730                 735
Val Ala Val Gly Leu Pro Asp Arg Glu Asp Ala Gln Thr Gly Ser
                740                 745                 750
Val Ala Ala Gly Ile Met Gly Asp Val Val Pro His Ile Ser
                755                 760                 765
Ala Ala Gly Ala Gly Glu Ala Leu Glu Gly Ala Leu Gly Gln Gly
                770                 775                 780
Trp Asp Ser Lys Glu Lys Glu Glu Ala Ala Gly Glu His Ala
                785                 790                 795
Gly Gly Gln Glu Phe Gly Leu Glu Gly Ser Ala Glu Glu Val
                800                 805                 810
Thr Gly Arg Gly Ser Gln Val Glu Ala Phe Glu Ser Arg Glu Gly
                815                 820                 825
Gly Pro Trp Gly Gly Arg Val Glu Ala Glu Ser Ala Gly Ala
                830                 835                 840
Glu Asp Ser Cys Gly Leu Asp Pro Ala Gly Ser Gln Thr Ala Arg
                845                 850                 855
Ala Glu Gly Met Gly Ala Met Val Glu Ala Gly Gly Leu Leu Glu
                860                 865                 870
Lys Trp Thr Leu Leu Glu Glu Ala Val Gly Trp Gln Glu Arg
                875                 880                 885
Glu Gln Arg Glu Asp Ser Glu Gly Arg Cys Gly Asp Tyr His Pro
                890                 895                 900
Glu Gly Glu Ala Pro Arg Leu Leu Asp Ala Glu Gly Leu Met Val
                905                 910                 915
Thr Gly Gly Arg Arg Ala Glu Ala Lys Glu Thr Glu Pro Glu Ser
                920                 925                 930
Leu Glu His Val Arg Gly Gln Glu Glu Gln Pro Thr His Gln Ala
                935                 940                 945
Pro Ala Glu Ala Ala Pro Glu Ser Val Gly Glu Ala Glu Thr Ala
                950                 955                 960
Glu Ala Met Gly Ser Ala Arg Gly Gly Ala Ala Asn Ser Trp Ser
                965                 970                 975
Glu Ala Pro Leu Pro Gly Ser Leu Leu Asp Val Ser Val Pro Arg
                980                 985                 990
Ser Arg Val His Leu Ser Arg Ser Ser Gln Arg Ser Arg
                995                 1000                1005
Pro Ser Phe Arg Arg Thr Pro Ala Trp Glu Gln Gln Glu Glu Pro
                1010                1015                1020
Pro Ala Pro Asn Pro Pro Glu Glu Leu Ser Ala Pro Glu Gln
                1025                1030                1035
Arg Pro Leu Gln Leu Glu Glu Pro Leu Glu Pro Ser Pro Leu Arg
                1040                1045                1050
His Asp Gly Thr Pro Val Pro Ala Arg Arg Pro Leu Gly His
                1055                1060                1065
Gly Phe Gly Leu Ala His Pro Gly Met Met Gln Glu Leu Gln Ala
                1070                1075                1080
Arg Leu Gly Arg Pro Lys Pro Gln
                1085
```

<210> SEQ ID NO 3
<211> LENGTH: 631
<212> TYPE: DNA
<213> ORGANISM: Homo sapien

<400> SEQUENCE: 3

```
aagctgttgt atgggtcaga gaaactgagg atgaggaggc ggaggctgac agaacatcca      60
gaagaggctg gaggctgcaa gcggtggctg tgggcctccc ggaccgtgag gatgcacaga     120
ctggctctgt ggctgctggg attatggggg gtgatgtggt cccacacatc agcgctgctg     180
gccgtggtga agctttggaa ggggcgcttg gcaaggctg ggactcgaaa gaaaggaag      240
aggcagcagc aggagagcat gcaggtgggc aagaatttgg tctggagggc tcagcagagg     300
aagaggtgac tggcagaggc agccaagtag aggcttttga gtccagggag ggaggacctt     360
ggggagggcg ggtagaggcc gaggaatctg caggcgcaga ggacagctgt gggctggatc     420
ccgcgggctc ccagacagcg agggcagagg ggatgggagc catggtggag ctggggggc     480
ttctagaaaa gtggacgctg ttggaagaag aggctgttgg atggcaggag agagaacaga    540
gggaagacag tgaggggcgg tgtggggact accaccctga gggagaggca ccaaggctcc    600
ttgatgcaga gggactcatg gtgacggggg g                                   631
```

<210> SEQ ID NO 4
<211> LENGTH: 209
<212> TYPE: PRT
<213> ORGANISM: Homo sapien

<400> SEQUENCE: 4

```
Ala Val Val Trp Val Arg Glu Thr Glu Asp Glu Glu Ala Glu Ala
                 5                  10                  15
Asp Arg Thr Ser Arg Arg Gly Trp Arg Leu Gln Ala Val Ala Val
             20                  25                  30
Gly Leu Pro Asp Arg Glu Asp Ala Gln Thr Gly Ser Val Ala Ala
         35                  40                  45
Gly Ile Met Gly Gly Asp Val Val Pro His Ile Ser Ala Ala Gly
     50                  55                  60
Arg Gly Glu Ala Leu Glu Gly Ala Leu Gly Gln Gly Trp Asp Ser
 65                  70                  75
Lys Glu Lys Glu Glu Ala Ala Gly Glu His Ala Gly Gly Gln
             80                  85                  90
Glu Phe Gly Leu Glu Gly Ser Ala Glu Glu Val Thr Gly Arg
             95                 100                 105
Gly Ser Gln Val Glu Ala Phe Glu Ser Arg Glu Gly Gly Pro Trp
            110                 115                 120
Gly Gly Arg Val Glu Ala Glu Glu Ser Ala Gly Ala Glu Asp Ser
            125                 130                 135
Cys Gly Leu Asp Pro Ala Gly Ser Gln Thr Ala Arg Ala Glu Gly
            140                 145                 150
Met Gly Ala Met Val Glu Ala Gly Gly Leu Leu Glu Lys Trp Thr
            155                 160                 165
Leu Leu Glu Glu Glu Ala Val Gly Trp Gln Glu Arg Glu Gln
            170                 175                 180
Glu Asp Ser Glu Gly Arg Cys Gly Asp Tyr His Pro Glu Gly Glu
            185                 190                 195
Ala Pro Arg Leu Leu Asp Ala Glu Gly Leu Met Val Thr Gly
```

```
<210> SEQ ID NO 5
<211> LENGTH: 13
<212> TYPE: PRT
<213> ORGANISM: artificial sequence
<220> FEATURE:
<221> NAME/KEY: UNSURE
<222> LOCATION: 1..3
<223> OTHER INFORMATION: Glu, Leu or Ala; Ala or Leu; Gln, Val or Glu

<400> SEQUENCE: 5

Xaa Xaa Xaa Ala Glu Gly Leu Met Val Thr Gly Gly Arg
              5                   10

<210> SEQ ID NO 6
<211> LENGTH: 7
<212> TYPE: PRT
<213> ORGANISM: artificial sequence
<220> FEATURE:
<221> NAME/KEY: UNSURE
<222> LOCATION: 1..2
<223> OTHER INFORMATION: Val or Glu; Ala or Le

<400> SEQUENCE: 6

Xaa Xaa Val Met Gly Gln Met
              5

<210> SEQ ID NO 7
<211> LENGTH: 751
<212> TYPE: DNA
<213> ORGANISM: Homo sapien

<400> SEQUENCE: 7
gcggccgcgt ctaccgcggc cgcgtctacg acagacagga tggacttcct ccggctatac      60
ctccctgggc tgcaccaggc cttgaggggg gcactggatt ccctcggcac ctttgtctcc     120
tacctcctgg gagatgcagt ccccactgta gagcgggagg cgcaggcggc tgaggaactg     180
ggggtggtgg cggtgggaaa gacagggaag attgtagagg aggaagccca ggaggacctg     240
gagggcctta gaggcagcca aaacgagggg gctggaaggc tgagagggcc tggagatgac     300
agaagacatg aagtggggag ctcagctgta gaacagacct ggggctgggg agatggcagc     360
tcccatgggt cccaagcaga gaggcaggac agtgggctg gggagacagc caaggctgcc      420
aggtgccagg agccaagcgc ccacttggag gccagaaaga aatccaaggc agggtctggg     480
gcttgccaag acaggagcgg ccaagcccag gagaggcagg agtcccatga gcaggaagtg     540
aacagagagg agaggctgag aagctgggaa caggaggagg aggaggaaga ggtcagggca     600
agggagccag ggatggccag aggggcggag tcagagtgga cctggcatgg ggagacggag     660
gggaaggctg gtgctgttgg gccaaaggcg cagggggaca accgggagat ggagcagggg     720
gtcagggagg cagatgcagg ggaaactgag g                                   751

<210> SEQ ID NO 8
<211> LENGTH: 1466
<212> TYPE: DNA
<213> ORGANISM: Homo sapien

<400> SEQUENCE: 8
cgggagatgg agcagggggt cagggaggca gatgcagggg aaactgagga gcctggggcc      60 gaagggctg ggaaaggaga agaggtggta gtggtggaga aggcctgtga aagcactagg     120
gcatggggga cgtggggccc aggggcagag cctgaggact ggggaatctt aggcagagag     180
```

-continued

```
gaggccagga caaccccagg tagggaagag gccagggcaa ttttagatgg ggaggaagcc      240
aggacaatct caggcgggga ggaggctgag acagcctcag gcggggagga ggctgaaaca      300
gcctcaggcg gggaggaggc cgggacagcc tcggagggg aggaggccgg gatatcctca       360
ggcggggagg ctgggacagc ctcaggaggg gaggaggccg gacagcctc tggaggggac       420 gaggcctgga caacctcagg caaagaggag gctgacctgc tgggagtcag acagactcaa      480
tatggagcag ttccaggaga aaggctccta gaggctactg gaaaagtctg ggtcctagag      540 gaggagggggg atgaggagag agaggctgag gtgagccctt tccccaaaca ggcccaggtc    600
ctgggcactg aaagaacaga gaggctgct gagagccaga ccgcagggag gaagctgtg        660 ggaggccagg aggcagggga gagctttgag ggccaggtag acctgcgtgg taaggaggct     720
gagatgaggc aggacttggg gatcagggcc gaccgggcca agatggaaga gctggtacag     780
gcagaggagg cccaggagga gagagggagc agcagggatc cagtggctga gctgccctca     840
gatggagagg ctgaaggcac tgccgacttg gaggcaactc cagaggccag gcctgaggag    900
gagctcacag gggaggagag tgaggcggcc cagactagct gtggcctact gggcgtggaa    960
tggggtggcc tcacacacag cgtcaccaaa ggccagggac ctgagctgat gggggggtgcc  1020 cagaccccaa ctaagcaacc cgaggaaagg gaggcagggg aggtggagct catgggagtt   1080
ctggccctga gcaaagagga gcaggagagg agcctggagg caggtcccag gcacgcgggg  1140
tctgtaaagc ctgaggcctc cgaggccttc ccaggagcct gggaaaaccg cacgagaaag    1200
gacatggaga gaggaaatac tcaggaggat gcggccgatg gcgagcagcg ggaggaggag   1260
gagactgcgg gaggccagac cctggcggct gaggctgaag gagaccgaga gtctgaacta    1320
tcagaagtcc cagaggcagg cggggagggg ctgacaaccc aggacgcggg atgtggaact    1380
gaggagggag aggcatctgt ctcagagaac caggagctgg acggaagcac agggggcagac   1440 gcagggcctt gcccgtcact gggaga                                          1466
```

<210> SEQ ID NO 9
<211> LENGTH: 1851
<212> TYPE: DNA
<213> ORGANISM: Homo sapien

<400> SEQUENCE: 9

```
tcaggaggat gcggccgatg gcgagcagcg ggaggaggag gagactgcgg gaggccagac      60
cctggcggct gaggctgaag gagaccgaga gtctgaacta tcagaagtcc cagaggcagg    120
cggggagggg ctgacaaccc aggacgcggg atgtggaact gaggagggag aggcatctgt    180
ctcagagaac caggagctgg acggaagcac agggggcagac gcagggcctt gcccgtcact   240
gggagaggcc tatgccagag aaactgagga tgaggaggcg gaggctgaca gaacatccag    300
aagaggctgg aggctgcaag cggtggctgt gggcctcccg gaccgtgagg atgcacagac   360
tggctctgtg gctgctggga ttatggggg tgatgtggtc ccacacatca gcgctgctgg    420
cgctggtgaa gctttggaag gggcgcttgg gcaaggctgg gactcgaaag aaaaggaaga   480
ggcagcagca ggagagcatg caggtgggca agaatttggt ctggagggct cagcagagga   540
agaggtgact ggcagaggca gccaagtaga ggcttttgag tccagggagg gaggaccttg   600 ggggagggcgg gtagaggccg aggaatctgc aggcgcagag gacagctgtg gctggatcc   660 cgcgggctcc cagacagcga gggcagaggg gatgggagcc atggtggagg ctgggggggct  720 tctagaaaag tggacgctgt tggaagaaga ggctgttgga tggcaggaga gagaacagag   780
```

-continued

```
ggaagacagt gaggggcggt gtggggacta ccaccctgag ggagaggcac caaggctcct    840
tgatgcagag ggtctcatgg tgaccggggg ccggagggca gaggccaagg agactgagcc    900
agaaagcctg gaacatgtca ggggccagga ggagcagcca acacaccagg cccctgcaga    960
agctgcgccg gagtcagtcg gggaagccga gacggctgag gccatgggca gtgccagagg   1020
aggtgctgcc aacagctgga gcgaggcccc gctccccggg tccctcctag acgtctctgt   1080
cccaaggagt cgcgtgcacc tctcgagaag ctcctcacag cgtcgctccc ggccctcttt   1140
tcgtcggact ccggcctggg agcagcagga ggagccccca gcccccaacc ctcctgagga   1200
ggagctgtca gctcctgagc agagacccct ccagctggag gaacccctgg agccaagccc   1260
tctgaggcat gatgggaccc cggtgccagc caggagaagg cccctgggac acgggtttgg   1320
cctcgcgcac cctggcatga tgcaggagct gcaagcccgt ctgggccggc ctaagcccca   1380
gtgactgaga cccggtgctc tgggagccag gccctgagtg ggtgccagaa ggcttgctcc   1440
aatgccactg agccctgctc cctctgccac tgtggacaca tcctctccac cctctgggcc   1500
tcagtgtctt gatgtatcat tcatggagca ggcaaaacca gacgtctggg aataccgtga   1560
acttaaggag tctgattctc cgacacaggc tggtggacca cctaccccac tgagaccacc   1620
tctcagggtg cctgccctgg ttcctcccca gcctgagtca gctgtctgga ctgcaaggag   1680
gctgggcacg gggctcacg cctgtcaccc cagagctttg ggaggccaag gtgggaggat    1740
cgcttgagac caggagttcg agaccagcct gggcagcata gcaagatccc catcttttaa   1800
aaacaaaata aaacaataaa gactgcaagg aaaaaaaaaa aaaaaaaaaa a            1851

<210> SEQ ID NO 10
<211> LENGTH: 11
<212> TYPE: PRT
<213> ORGANISM: artificial sequence
<220> FEATURE:
<221> NAME/KEY: MOD_RES/AMIDATION
<222> LOCATION: 11
<223> OTHER INFORMATION: C-terminal arginine was amidated

<400> SEQUENCE: 10

Cys Ala Glu Gly Leu Met Val Thr Gly Gly Arg
                5                   10
```